(12) United States Patent
Lipowsky et al.

(10) Patent No.: US 11,848,074 B2
(45) Date of Patent: Dec. 19, 2023

(54) CODON OPTIMIZATION

(71) Applicant: GOTTFRIED WILHELM LEIBNIZ UNIVERSITÄT HANNOVER, Hannover (DE)

(72) Inventors: Reinhard Lipowsky, Kleinmachnow (DE); Sophia Rudorf, Potsdam (DE); Holger Lossner, Langen (DE); Jan-Hendrik Trosemeier, Langen (DE); Ina Koch, Berlin (DE); Christel Kamp, Langen (DE)

(73) Assignee: GOTTFRIED WILHELM LEIBNIZ UNIVERSITÄT HANNOVER, Hannover (DE)

( * ) Notice: Subject to any disclaimer, the term of this patent is extended or adjusted under 35 U.S.C. 154(b) by 1077 days.

(21) Appl. No.: 16/467,528

(22) PCT Filed: Dec. 6, 2017

(86) PCT No.: PCT/EP2017/081685
§ 371 (c)(1),
(2) Date: Jun. 7, 2019

(87) PCT Pub. No.: WO2018/104385
PCT Pub. Date: Jun. 14, 2018

(65) Prior Publication Data
US 2019/0325989 A1 Oct. 24, 2019

(30) Foreign Application Priority Data
Dec. 7, 2016 (EP) ..................................... 16202752

(51) Int. Cl.
*G16B 30/00* (2019.01)
*G16B 35/00* (2019.01)
(Continued)

(52) U.S. Cl.
CPC ........... *G16B 30/00* (2019.02); *C12Q 1/6869* (2013.01); *G16B 35/00* (2019.02); *G16B 40/00* (2019.02); *G16B 40/20* (2019.02); *G16B 50/50* (2019.02)

(58) Field of Classification Search
CPC ........ G16B 30/00; G16B 40/20; G16B 35/00; G14B 40/00; C12Q 1/6869
(Continued)

(56) References Cited

U.S. PATENT DOCUMENTS

| 2011/0171737 A1* | 7/2011 | Hellinga | ................ G16B 20/20 |
| | | | 536/23.7 |
| 2013/0149699 A1 | 6/2013 | Barral et al. | |
| 2017/0016008 A1 | 1/2017 | Sharma et al. | |

FOREIGN PATENT DOCUMENTS

| EP | 2 545 176 | 5/2016 |
| WO | WO 2011/111034 | 9/2011 |
| WO | WO 2016/112142 | 7/2016 |

OTHER PUBLICATIONS

Jackson, J.H., Schmidt, T.M. & Herring, P.A. A systems approach to model natural variation in reactive properties of bacterial ribosomes. BMC Syst Biol 2, 62 (2008). (Year: 2008).*

(Continued)

*Primary Examiner* — Larry D Riggs, II
*Assistant Examiner* — Guozhen Liu
(74) *Attorney, Agent, or Firm* — SALIWANCHIK, LLOYD & EISENSCHENK

(57) ABSTRACT

A method for determining an optimized nucleotide sequence encoding a predetermined amino acid sequence, wherein the nucleotide sequence is optimized for expression in a host cell, and wherein the method comprises the steps of: (a) generating a plurality of candidate nucleotide sequences encoding the predetermined amino acid sequence; (b) obtaining a sequence score based on a scoring function based on a plurality of sequence features that influence protein expression in the host cell using a statistical machine learning algorithm, wherein the plurality of sequence features comprises one or more sequence features selected from the group consisting of protein per time, average elongation rate and accuracy for each of the plurality of candidate (Continued)

nucleotide sequences of step (a); and (c) determining the candidate nucleotide sequence with optimized protein expression in the host cell as the optimized nucleotide sequence.

16 Claims, 17 Drawing Sheets

Specification includes a Sequence Listing.

(51) Int. Cl.
    *G16B 40/00* (2019.01)
    *G16B 40/20* (2019.01)
    *C12Q 1/6869* (2018.01)
    *G16B 50/50* (2019.01)
    *G16B 25/20* (2019.01)

(58) Field of Classification Search
    USPC .......................................................... 702/19
    See application file for complete search history.

(56) References Cited

OTHER PUBLICATIONS

Hofner, B., Mayr, A., Robinzonov, N. et al. Model-based boosting in R: a hands-on tutorial using the R package mboost . Comput Stat 29, 3-35 (2014) (Year: 2014).*

Tamir Tuller, Asaf Carmi, et al: ("An Evolutionarily Conserved Mechanism for Controlling the Efficiency of Protein Translation", vol. 141, Issue 2, Apr. 16, 2010, pp. 344-354) (Year: 2010).*

Caniparoli, L. et al. "Modeling the effect of codon translation rates on co-translational protein folding mechanisms of arbitrary complexity" *The Journal of Chemical Physics*, 2015, pp. 145102-1-145102-9, vol. 142, No. 14.

Fernandes, A. et al. "Improving Protein Expression Prediction Using Extra Features and Ensemble Averaging" *PLOS One*, Mar. 2, 2016, pp. 1-15, vol. 11, No. 3.

Lanza, A. M. et al. "A condition-specific codon optimization approach for improved heterologous gene expression in *Saccharomyces cerevisiae*" *BMC Systems Biology*, 2014, pp. 1-10, vol. 8, No. 33.

Nissley, D. A. et al. "Timing Is Everything: Unifying Codon Translation Rates and Nascent Proteome Behavior" *Journal of the American Chemical Society*, 2014, pp. 17892-17898, vol. 136, No. 52.

Plotkin, J. B. et al. "Synonymous but not the same: the causes and consequences of codon bias" *Nature Reviews Genetics*, Jan. 2011, pp. 32-42, vol. 12, No. 1.

Rudorf, S. et al. "Protein Synthesis in *E. coli*: Dependence of Codon-Specific Elongation on tRNA Concentration and Codon Usage" *PLOS One*, Aug. 13, 2015, pp. 1-22, vol. 10, No. 8.

Written Opinion in International Application No. PCT/EP2017/081685, dated Mar. 16, 2018, pp. 1-11.

* cited by examiner

SEQUENCE LISTING

```
<160> NUMBER OF SEQ ID NOS: 38

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide oHL20

<400> SEQUENCE: 1
gcctgcttgc cgaatatc                                                 18

<210> SEQ ID NO 2
<211> LENGTH: 61
<212> TYPE: DNA
<213> ORGANISM: Artificial Sequence
<220> FEATURE:
<223> OTHER INFORMATION: Oligonucleotide oJT1

<400> SEQUENCE: 2
atgcaaaaac tcattaactc agtgcaaaac tatgcctggg tgtgtaggct ggagctgctt    60
c                                                                   61

<210> SEQ ID NO 3
<211> LENGTH: 66
<212> TYPE: DNA
<213> ORGANISM: Artificial Sequence
```

```
<220> FEATURE:
<223> OTHER INFORMATION: Oligonucleotide oJT2

<400> SEQUENCE: 3
ctacagcttg ttataaacac gcgctaaacg gcccgtgccg ctggcgcata tgaatatcct        60
ccttag                                                                   66

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide oJT4

<400> SEQUENCE: 4
gaaaccaggc ggattaaacc                                                    20

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide oJT7

<400> SEQUENCE: 5
ggatatcata tgcaaaaact cattaactca g                                       31

<210> SEQ ID NO 6
<211> LENGTH: 34
<212> TYPE: DNA
<213> ORGANISM: Artificial Sequence
<220> FEATURE:
<223> OTHER INFORMATION: Oligonucleotide oJT8

<400> SEQUENCE: 6
ggatatcact agtctacagc ttgttataaa cacg                                    34

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide oJT11

<400> SEQUENCE: 7
tccggccttt attcacattc                                                    20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide oJT12

<400> SEQUENCE: 8
cgtttcagtt tgctcatgga                                                    20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide oJT13
```

-continued

```
<400> SEQUENCE: 9
cctcccattg atctccacat                                                 20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide oJT14

<400> SEQUENCE: 10
ggtcagtgcg gttttgctac                                                 20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide oJT16

<400> SEQUENCE: 11
gattggcgat gccataaagt                                                 20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide oJT17

<400> SEQUENCE: 12
attggcgatg ccataaagtt                                                 20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide oJT21

<400> SEQUENCE: 13
gttttagagc cccatgcgta                                                 20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide oJT23

<400> SEQUENCE: 14
gtttgcgatg ccgtacagtt                                                 20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide oJT24

<400> SEQUENCE: 15
gggttggcta taccgtacaa                                                 20
```

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide oJT27

<400> SEQUENCE: 16
ccatacagtt cggtcagtgc                                          20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide oJT28

<400> SEQUENCE: 17
tggttgttgt tgtggattgg                                          20

<210> SEQ ID NO 18
<211> LENGTH: 1176
<212> TYPE: DNA
<213> ORGANISM: Artificial Sequence
<220> FEATURE:
<223> OTHER INFORMATION: Coding sequence for manAwt

<400> SEQUENCE: 18
atgcaaaaac tcattaactc agtgcaaaac tatgcctggg gaagtaaaac tgcgttaacg      60
gaactttatg gcatcgccaa tccgcagcag cagccaatgg ctgaactctg gatgggcgcg     120
catcccaaaa gcagctcgcg aatcaccacc gccaacggcg aaaccgtctc cctgcgtgac     180
gccatcgaaa agaataaaac cgccatgctg ggcgaagcgg tagccaaccg tttcggcgaa     240
ctgccgtttc tgtttaaagt actgtgcgcc gcacaaccgc tctctattca ggtgcacccg     300
aataaacgca actccgaaat cggtttcgcg aaagaaaatg cggcgggtat ccccatggat     360
gccgcagagc ggaactataa agatcctaac cataaaccag agctggtttt tgccctgacg     420
cctttcctgg cgatgaacgc gttccgcgaa ttttctgaca ttgtctcttt actgcaacct     480
gtcgccggcg cgcattccgc tatcgcccac ttttttgcagg tgccgaatgc tgaacgtctg     540
agccagcttt cgccagcct gttgaatatg caaggcgaag aaaaatcccg cgcgttagcc     600
gtactcaaag cggcgcttaa cagccagcaa ggcgaaccgt ggcaaacgat ccgcgtgatt     660
tcagagtatt atcctgacga cagcgggctt ttctctcctt gttgctgaa tgtggtcaaa     720
ctgaatcccg gcgaggcgat gttcctgttt gctgaaacgc ctcatgctta tctgcagggc     780
gttgcgctgg aagtcatggc gaactccgat aacgttctgc gcgctggcct tacgccaaaa     840
tatatcgaca tccctgagct ggtcgcgaac gtgaagttcg aacctaagcc tgccggcgag     900
ttgctgactg ccccggtgaa aagcggcgcg gagctggact tcccaattcc ggttgacgat     960
tttgcttttt cactgcacga cctggcgctt caggagacga gcatcggcca acacagcgcc    1020
gcgattctgt tctgcgttga gggtgaggcg gtgttacgta agatgaaca gcgtctggta    1080
ctgaagccgg gtgaatctgc ctttatcggc gcggatgagt ctccggttaa cgccagcggc    1140
acgggccgtt tagcgcgtgt ttataacaag ctgtag                             1176

<210> SEQ ID NO 19
<211> LENGTH: 1176
<212> TYPE: DNA
<213> ORGANISM: Artificial Sequence
<220> FEATURE:
<223> OTHER INFORMATION: Coding sequence for manA1

<400> SEQUENCE: 19

| | | |
|---|---|---|
| atgcagaaac tgattaatag cgtgcagaat tatgcatggg gatcgaaaac cgcactgacc | 60 |
| gaactgtatg gtattgcaaa tccgcagcag cagccaatgg cagaactgtg gatgggtgca | 120 |
| catccgaaaa gcagctcccg aattaccacc gcaaatggtg aaaccgttag cctgcgtgat | 180 |
| gcaatcgaaa aaaacaaaac cgccatgctg ggtgaagcag ttgcaaatcg ttttggtgaa | 240 |
| ctgccgtttc tgtttaaagt tctgtgtgca gcacagccgc tgagcattca ggttcatccg | 300 |
| aataaacgta atagcgaaat tggctttgcc aaagaaaatg cagcaggtat tcccatggat | 360 |
| gcagcagaac gtaactataa agatccgaat cataaaccag aactggtttt tgcactgacc | 420 |
| ccgtttctgg caatgaatgc atttcgtgaa tttagcgata ttgtgagcct gctgcagccg | 480 |
| gttgccggtg cccatagcgc aattgcacat tttctgcagg ttccgaatgc cgaacgtctg | 540 |
| agccagctgt ttgcaagcct gctgaatatg cagggtgaag aaaaaagccg tgcactggca | 600 |
| gttctgaaag cagcactgaa tagccagcag ggcgaaccgt ggcagaccat tcgtgttatt | 660 |
| agcgaatatt atccggatga tagcggtctt tttagccctc tgctgctgaa tgttgttaaa | 720 |
| ctgaatccgg gtgaagccat gtttctgttc gcagaaacac cgcatgctta tctgcagggt | 780 |
| gttgcactgg aagttatggc aaatagcgat aatgttctgc gtgcaggtct gaccccgaaa | 840 |
| tacattgata ttccagaact ggttgccaac gtgaaatttg aaccgaaacc ggcaggcgaa | 900 |
| ctgctgaccg caccggttaa aagcggtgca gaactggatt ttccgattcc ggtggatgat | 960 |
| tttgcattta gtttgcatga tctggcactg caagaaacca gcattggtca gcatagcgca | 1020 |
| gcaattctgt tttgtgttga aggtgaagcc gttctgcgta agatgaaca cgtctggtt | 1080 |
| ctgaaacctg gtgaaagcgc atttattggt gcagatgaaa gtccggttaa tgcaagcggc | 1140 |
| accggtcgtc tggcacgtgt ttataacaaa ctgtaa | 1176 |

<210> SEQ ID NO 20
<211> LENGTH: 1176
<212> TYPE: DNA
<213> ORGANISM: Artificial Sequence
<220> FEATURE:
<223> OTHER INFORMATION: Coding sequence for manA2

<400> SEQUENCE: 20

| | | |
|---|---|---|
| atgcagaaac tgattaatag cgtgcagaat tatgcatggg gtagcaaaac cgcactgacc | 60 |
| gaactgtatg gtattgcaaa tccgcagcag cagccgatgg cagaactgtg gatgggtgca | 120 |
| catccgaaaa gcagcagtcg tattaccacc gcaaatggtg aaaccgttag cctgcgtgat | 180 |
| gcaatcgaaa aaaacaaaac cgccatgctg ggtgaagcag ttgcaaatcg ttttggtgaa | 240 |
| ctgccgtttc tgtttaaagt tctgtgtgca gcacagccgc tgagcattca ggttcatccg | 300 |
| aataaacgta atagcgaaat tggctttgcc aaagaaaatg cagcaggtat tccgatggat | 360 |
| gcagcagaac gtaactataa agatccgaat cataaaccgg aactggtttt tgcactgacc | 420 |
| ccgtttctgg caatgaatgc atttcgtgaa tttagcgata ttgtgagcct gctgcagccg | 480 |
| gttgccggtg cacatagcgc aattgcacat tttctgcagg ttccgaatgc agaacgtctg | 540 |
| agccagctgt ttgcaagcct gctgaatatg cagggtgaag aaaaaagccg tgcactggca | 600 |
| gttctgaaag cagcactgaa tagccagcag ggcgaaccgt ggcagaccat tcgtgttatt | 660 |
| agcgaatatt atccggatga tagcggtctg tttagccctc tgctgctgaa tgttgttaaa | 720 |

| | |
|---|---|
| ctgaatccgg gtgaagccat gtttctgttc gcagaaacac cgcatgcata tctgcagggt | 780 |
| gttgcactgg aagttatggc aaatagcgat aatgttctgc gtgcaggtct gaccccgaaa | 840 |
| tacattgata ttccagaact ggttgccaac gtgaaatttg aaccgaaacc ggcaggcgaa | 900 |
| ctgctgaccg caccggttaa aagcggtgca gaactggatt ttccgattcc ggtggatgat | 960 |
| tttgcattta gtctgcatga tctggcactg caagaaacca gcattggtca gcatagcgca | 1020 |
| gcaattctgt tttgtgttga aggtgaagcc gttctgcgta aagatgaaca gcgtctggtt | 1080 |
| ctgaaacctg gtgaaagcgc atttattggt gcagatgaaa gtccggttaa tgcaagcggc | 1140 |
| accggtcgtc tggcacgtgt ttataacaaa ctgtaa | 1176 |

<210> SEQ ID NO 21
<211> LENGTH: 1176
<212> TYPE: DNA
<213> ORGANISM: Artificial Sequence
<220> FEATURE:
<223> OTHER INFORMATION: Coding sequence for manA3

<400> SEQUENCE: 21

| | |
|---|---|
| atgcaaaaac tcattaactc agtgcaaaac tatgcctggg aagtaaaaac tgcgttaacg | 60 |
| gaactttatg gcatcgccaa tcctcagcag cagccaatgg ctgaactctg gatgggcgcg | 120 |
| catcccaaaa gctcatcgcg aatcacgacc gcgaatggtg aaaccgttag cctgcgtgat | 180 |
| gcaatcgaaa aaacaaaac cgccatgctg ggtgaagcag ttgcaaatcg ttttggtgaa | 240 |
| ctgccgtttc tgtttaaagt tctgtgtgca gcacagccgc tgagcattca ggttcatccg | 300 |
| aataaacgta tagcgaaat ggctttgcc aaagaaaatg cagcaggtat tccgatggat | 360 |
| gcagcagaac gtaactataa agatccgaat cataaaccag aactggtttt tgcactgacc | 420 |
| ccgtttctgg caatgaatgc atttcgtgaa tttagcgata ttgtgagcct gctgcagccg | 480 |
| gttgccggtg cccatagcgc aattgcacat tttctgcagg ttccgaatgc cgaacgtctg | 540 |
| agccagctgt tgcaagcct gctgaatatg cagggtgaag aaaaaagccg tgcactggca | 600 |
| gttctgaaag cagcactgaa tagccagcag ggcgaaccgt ggcagaccat tcgtgttatt | 660 |
| agcgaatatt atccggatga tagcggtctt tttagccctc tgctgctgaa tgttgttaaa | 720 |
| ctgaatccgg gtgaagccat gtttctgttc gcagaaacac cgcatgctta tctgcagggt | 780 |
| gttgcactgg aagttatggc aaatagcgat aatgttctgc gtgcaggtct gaccccgaaa | 840 |
| tacattgata ttccagaact ggttgccaac gtgaaatttg aaccgaaacc ggcaggcgaa | 900 |
| ctgctgaccg caccggttaa aagcggtgca gaactggatt ttccgattcc ggtggatgat | 960 |
| tttgcattta gtttgcatga tctggcactg caagaaacca gcattggtca gcatagcgca | 1020 |
| gcaattctgt tttgtgttga aggtgaagcc gttctgcgta aagatgaaca gcgtctggtt | 1080 |
| ctgaaacctg gtgaaagcgc atttattggt gcagatgaaa gtccggttaa tgcaagcggc | 1140 |
| accggtcgtc tggcacgtgt ttataacaaa ctgtaa | 1176 |

<210> SEQ ID NO 22
<211> LENGTH: 1176
<212> TYPE: DNA
<213> ORGANISM: Artificial Sequence
<220> FEATURE:
<223> OTHER INFORMATION: Coding sequence for manA4a

<400> SEQUENCE: 22

| | |
|---|---|
| atgcaaaagc taataaattc cgtccaaaat tatgcctggg atccaagac cgccctaacc | 60 |
| gagctatatg gaatagccaa tccacaacaa caaccaatgg ccgagctatg gatgggagcc | 120 |

| | |
|---|---|
| catccaaagt cctcctcccg ataaccacc gccaatggag agaccgtctc cctacgggat | 180 |
| gccatagaga agaataagac cgccatgcta ggagaggccg tcgccaatcg gtttggagag | 240 |
| ctaccatttc tatttaaggt cctatgtgcc gcccaaccac tatccataca agtccatcca | 300 |
| aataagcgga attccgagat aggatttgcc aaggagaatg ccgccggaat accaatggat | 360 |
| gccgccgagc ggaattataa ggatccaaat cataagccag agctagtctt tgccctaacc | 420 |
| ccatttctag ccatgaatgc ctttcgggag ttttccgata tagtctccct actacaacca | 480 |
| gtcgccggag cccattccgc catagcccat tttctacaag tcccaaatgc cgagcggcta | 540 |
| tcccaactat ttgcctccct actaaatatg caaggagagg agaagtcccg ggccctagcc | 600 |
| gtcctaaagg ccgccctaaa ttcccaacaa ggagagccat ggcaaaccat acgggtcata | 660 |
| tccgagtatt atccagatga ttccggacta ttttccccac tactactaaa tgtcgtcaag | 720 |
| ctaaatccag agaggccat gtttctattt gccgagaccc cacatgccta tctacaagga | 780 |
| gtcgccctag aggtcatggc caattccgat aatgtcctac gggccggact aaccccaaag | 840 |
| tatatagata taccagagct agtcgccaat gtcaagtttg agcaaagcc agccggagag | 900 |
| ctactaaccg ccccagtcaa gtccggagcc gagctagatt ttccaatacc agtcgatgat | 960 |
| tttgcctttt cctacatga tctagcccta caagagacct ccataggaca acattccgcc | 1020 |
| gccatactat tttgtgtcga gggagaggcc gtcctacgga aggatgagca acggctagtc | 1080 |
| ctaaagccag agagtccgc ctttatagga gccgatgagt ccccagtcaa tgcctccgga | 1140 |
| accggacggc tagcccgggt ctataataag ctatag | 1176 |

<210> SEQ ID NO 23
<211> LENGTH: 1176
<212> TYPE: DNA
<213> ORGANISM: Artificial Sequence
<220> FEATURE:
<223> OTHER INFORMATION: Coding sequence for manA5

<400> SEQUENCE: 23

| | |
|---|---|
| atgcagaaac tgatcaactc agttcagaac tacgcatggg gctcaaaaac ggcactgacg | 60 |
| gaactgtacg gcatcgcaaa ccccagcag cagcccatgg cagaactgtg gatgggcgca | 120 |
| caccccaaat catcatcacg aatcacgacg gcaaacggcg aaacggtttc actgcgagac | 180 |
| gcaatcgaaa aaacaaaac ggcaatgctg ggcgaagcga ttgcaaaccg attcggcgaa | 240 |
| ctgcccttcc tgttcaaagt tctgtgcgca gcacagcccc tgtcaatcca ggttcacccc | 300 |
| aacaaacgaa actcagaaat cggcttcgca aaagaaaacg cagcaggcat ccccatggac | 360 |
| gcagcagaac gaaactacaa agaccccaac cacaaacccg aactggtttt cgcactgacg | 420 |
| cccttcctgg caatgaacgc attccgaaa ttctcagaca tcgtttcact gctgcagccc | 480 |
| gttgcaggcg cacactcagc aatcgcacac ttcctgcagg ttcccaacgc agaacgactg | 540 |
| tcacagctgt tcgcatcact gctgaacatg cagggcgaag aaaaatcacg agcactggca | 600 |
| gttctgaaag cagcactgaa ctcacagcag ggcgaaccct ggcagacgat ccgagttatc | 660 |
| tcagaatact accccgacga ctcaggcctg ttctcacccc tgctgctgaa cgttgttaaa | 720 |
| ctgaaccccg gcgaagcaat gttcctgttc gcagaaacgc ccacgcata cctgcagggc | 780 |
| gttgcactgg aagttatggc aaactcagac aacgttctgc gagcaggcct gacgcccaaa | 840 |
| tacatcgaca tccccgaact ggttgcaaac gttaaattcg aacccaaacc gcaggcgaa | 900 |
| ctgctgacgg caccgttaa atcaggcgca gaactggact cccccatccc cgttgacgac | 960 |
| ttcgcattct cactgcacga cctggcactg caggaaacgt caatcggcca gcactcagca | 1020 |

```
gcaatcctgt tctgcgttga aggcgaagca gttctgcgaa aagacgaaca gcgactggtt   1080
ctgaaacccg gcgaatcagc attcatcggc gcagacgaat cacccgttaa cgcatcaggc   1140
acgggccgac tggcacgagt ttacaacaaa ctgtag                             1176
```

<210> SEQ ID NO 24
<211> LENGTH: 1176
<212> TYPE: DNA
<213> ORGANISM: Artificial Sequence
<220> FEATURE:
<223> OTHER INFORMATION: Coding sequence for manA6

<400> SEQUENCE: 24

```
atgcaaaagc tcataaactc tgtgcaaaat tatgcatggg gtagcaagac tgctctaaca    60
gaattgtacg gtatagccaa cccgcaacag caacctatgg ccgaactatg gatgggtgct   120
cacccaaagt cgagctcccg gataactacc gccaacggag agaccgtctc acttagagat   180
gcgattgaga agaataaaac cgccatgctt ggggaggcgg ttgccaatcg gtttggtgag   240
ttaccatttc tctttaaagt attatgtgcc gcccagccac tctcgataca ggtgcatccg   300
aataaaagaa atagtgagat aggatttgcc aaagaaaacg cagcagggat accaatggac   360
gccgcagagc ggaattataa agacccaaat cacaagcccg agttagtgtt cgccttaacc   420
ccatttctag ccatgaacgc attcagagag ttcagtgata tagtcagcct actacagcca   480
gtcgctggag cccatagcgc tatcgcccac tttcttcagg tgccaaacgc cgaacggctc   540
agccaacttt tgcgagtct attaaatatg cagggtgagg aaaagtcgag ggcacttgcc   600
gtgctaaagg cagccctaaa ttcccagcaa ggagagccat ggcaaactat acgcgtcata   660
tcggaatact atcctgacga ctccgggctg tttagtccgc tactacttaa cgtcgttaaa   720
ctaaatccgg gcgaagcgat gttttttattt gctgaaaccc ctcacgccta tcttcagggt   780
gtcgccctcg aagtgatggc taattcagat aatgtcttac gggccggtct cacaccaaag   840
tatatagaca tcccagaatt agtcgccaac gtgaagttcg aaccaaagcc ggccggcgag   900
ctcttgaccg ccccagtcaa gagcggtgct gaactagatt ttccaatacc agtcgacgac   960
ttcgcctttt ccctccatga ccttgccctt caggagacct ccataggaca gcatagcgcc  1020
gcaatactat tctgcgtcga aggagaagcc gtgctccgga aggatgagca acggcttgtg  1080
ttgaagccag agagagcgc attcatagga gccgatgaga gtccggttaa tgcttccggt  1140
accggtagac tagccagggt gtataacaaa ctgtag                             1176
```

<210> SEQ ID NO 25
<211> LENGTH: 1176
<212> TYPE: DNA
<213> ORGANISM: Artificial Sequence
<220> FEATURE:
<223> OTHER INFORMATION: Coding sequence for manA7

<400> SEQUENCE: 25

```
atgcagaaac tgatcaactc tgttcagaac tacgcatggg gctctaaaac ggcactgacg    60
gaactgtacg gcatcgcaaa ccctcagcag cagcctatgg cagaactgtg gatgggcgca   120 cacccctaaat cttcttctcg aatcacgacg gcaaacggcg aaacggtttc tctgcgagac   180
gcaatcgaaa aaacaaaac ggcaatgctg ggcgaagcag ttgcaaaccg attcggcgaa   240
ctgccttttc cgttcaaagt tctgtgcgca gcacagcctc tgtctatcca ggttcaccct   300
aacaaacgaa actctgaaat cggcttcgca aagaaaaacg cagcaggcat ccctatggac   360
gcagcagaac gaaactacaa agaccctaac cacaaacctg aactggtttt cgcactgacg   420
```

```
cctttcctgg caatgaacgc attccgagaa ttctctgaca tcgtttctct gctgcagcct    480
gttgcaggcg cacactctgc aatcgcacac ttcctgcagg ttcctaacgc agaacgactg    540
tctcagctgt tcgcatctct gctgaacatg cagggcgaag aaaaatctcg agcactggca    600
gttctgaaag cagcactgaa ctctcagcag ggcgaacctt ggcagacgat ccgagttatc    660
tctgaatact accctgacga ctctggcctg ttctctcctc tgctgctgaa cgttgttaaa    720
ctgaaccctg gcgaagcaat gttcctgttc gcagaaacgc ctcacgcata cctgcagggc    780
gttgcactgg aagttatggc aaactctgac aacgttctgc gagcaggcct gacgcctaaa    840
tacatcgaca tccctgaact ggttgcaaac gttaaattcg aacctaaacc tgcaggcgaa    900
ctgctgacgg cacctgttaa atctggcgca gaactggact ccctatccc tgttgacgac    960
ttcgcattct ctctgcacga cctggcactg caggaaacgt ctatcggcca gcactctgca   1020
gcaatcctgt tctgcgttga aggcgaagca gttctgcgaa aagacgaaca gcgactggtt   1080
ctgaaacctg gcgaatctgc attcatcggc gcagacgaat ctcctgttaa cgcatctggc   1140
acgggccgac tggcacgagt ttacaacaaa ctgtaa                             1176

<210> SEQ ID NO 26
<211> LENGTH: 1176
<212> TYPE: DNA
<213> ORGANISM: Artificial Sequence
<220> FEATURE:
<223> OTHER INFORMATION: Coding sequence for manA8

<400> SEQUENCE: 26
atgcaaaaac tcattaactc agtgcaaaac tatgcctggg gaagtaaaac tgcgttaacg     60
gaactttatg gcatcgccaa tcctcagcag cagccaatgg ctgaactctg gatgggcgcg    120
catcccaaaa gctcatcgcg aatcacgacc gcaaacggcg aaacggtttc actgcgagac    180
gcaatcgaaa aaacaaaac ggcaatgctg ggcgaagcag ttgcaaaccg attcggcgaa    240
ctgcccttcc tgttcaaagt tctgtgcgca gcacagcccc tgtcaatcca ggttcacccc    300
aacaaacgaa actcagaaat cggcttcgca aaagaaaacg cagcaggcat ccccatggac    360
gcagcagaac gaaactacaa agaccccaac cacaaacccg aactggtttt cgcactgacg    420
cccttcctgg caatgaacgc attccgagaa ttctcagaca tcgtttcact gctgcagccc    480
gttgcaggcg cacactcagc aatcgcacac ttcctgcagg ttcccaacgc agaacgactg    540
tcacagctgt tcgcatcact gctgaacatg cagggcgaag aaaaatcacg agcactggca    600
gttctgaaag cagcactgaa ctcacagcag ggcgaaccct ggcagacgat ccgagttatc    660
tcagaatact accccgacga ctcaggcctg ttctcacccc tgctgctgaa cgttgttaaa    720
ctgaaccccg gcgaagcaat gttcctgttc gcagaaacgc ccacgcata cctgcagggc    780
gttgcactgg aagttatggc aaactcagac aacgttctgc gagcaggcct gacgcccaaa    840
tacatcgaca tccccgaact ggttgcaaac gttaaattcg aacccaaacc cgcaggcgaa    900
ctgctgacgg cacccgttaa atcaggcgca gaactggact ccccatccc cgttgacgac    960
ttcgcattct cactgcacga cctggcactg caggaaacgt caatcggcca gcactcagca   1020
gcaatcctgt tctgcgttga aggcgaagca gttctgcgaa aagacgaaca gcgactggtt   1080
ctgaaacccg gcgaatcagc attcatcggc gcagacgaat cacccgttaa cgcatcaggc   1140
acgggccgac tggcacgagt ttacaacaaa ctgtag                             1176
```

<210> SEQ ID NO 27
<211> LENGTH: 1176
<212> TYPE: DNA
<213> ORGANISM: Artificial Sequence
<220> FEATURE:
<223> OTHER INFORMATION: Coding sequence for manA9

<400> SEQUENCE: 27

| | | |
|---|---|---|
| atgcaaaaac tcattaactc agtgcaaaac tatgcctggg aagtaaaac tgcgttaacg | 60 |
| gaactttatg gcatcgccaa tcctcagcag cagccaatgg ctgaactctg gatgggcgcg | 120 |
| catcccaaaa gctcatcgcg aatcacgacc gccaacggag agaccgtctc acttagagat | 180 |
| gcgattgaga agaataaaac cgccatgctt ggggaggcgg ttgccaatcg gtttggtgag | 240 |
| ttaccatttc tctttaaagt attatgtgcc gcccagccac tctcgataca ggtgcatccg | 300 |
| aataaaagaa atagtgagat aggatttgcc aaagaaaacg cagcagggat accaatggac | 360 |
| gccgcagagc ggaattataa agacccaaat cacaagcccg agttagtgtt cgccttaacc | 420 |
| ccatttctag ccatgaacgc attcagagag ttcagtgata tagtcagcct actacagcca | 480 |
| gtcgctggag cccatagcgc tatcgcccac tttcttcagg tgccaaacgc cgaacggctc | 540 |
| agccaacttt ttgcgagtct attaaatatg cagggtgagg aaaagtcgag ggcacttgcc | 600 |
| gtgctaaagg cagccctaaa ttcccagcaa ggagagccat ggcaaactat acgcgtcata | 660 |
| tcggaatact atcctgacga ctccgggctg tttagtccgc tactacttaa cgtcgttaaa | 720 |
| ctaaatccgg gcgaagcgat gttttattt gctgaaaccc ctcacgccta tcttcagggt | 780 |
| gtcgccctcg aagtgatggc taattcagat aatgtcttac gggccggtct cacaccaaag | 840 |
| tatatagaca tcccagaatt agtcgccaac gtgaagttcg aaccaaagcc ggccggcgag | 900 |
| ctcttgaccg ccccagtcaa gagcggtgct gaactagatt ttccaatacc agtcgacgac | 960 |
| ttcgcctttt ccctccatga ccttgccctt caggagacct ccataggaca gcatagcgcc | 1020 |
| gcaatactat tctgcgtcga aggagaagcc gtgctccgga aggatgagca acggcttgtg | 1080 |
| ttgaagccag agagagcgc attcatagga gccgatgaga gtccggttaa tgcttccggt | 1140 |
| accggtagac tagccagggt gtataacaaa ctgtag | 1176 |

<210> SEQ ID NO 28
<211> LENGTH: 1176
<212> TYPE: DNA
<213> ORGANISM: Artificial Sequence
<220> FEATURE:
<223> OTHER INFORMATION: Coding sequence for manA10

<400> SEQUENCE: 28

| | | |
|---|---|---|
| atgcaaaaac tcattaactc agtgcaaaac tatgcctggg aagtaaaac tgcgttaacg | 60 |
| gaactttatg gcatcgccaa tcctcagcag cagccaatgg ctgaactctg gatgggcgcg | 120 |
| catcccaaaa gctcatcgcg aatcacgacc gcaaacggcg aaacggtttc tctgcgagac | 180 |
| gcaatcgaaa aaacaaaac ggcaatgctg ggcgaagcag ttgcaaaccg attcggcgaa | 240 |
| ctgcctttcc tgttcaaagt tctgtgcgca gcacagcctc tgtctatcca ggttcaccct | 300 |
| aacaaacgaa actctgaaat cggcttcgca aagaaaaacg cagcaggcat ccctatggac | 360 |
| gcagcagaac gaaactacaa agaccctaac cacaaacctg aactggtttt cgcactgacg | 420 |
| cctttcctgg caatgaacgc attccgagaa ttctctgaca tcgtttctct gctgcagcct | 480 |
| gttgcaggcg cacactctgc aatcgcacac ttcctgcagg ttcctaacgc agaacgactg | 540 |
| tctcagctgt tcgcatctct gctgaacatg cagggcgaag aaaaatctcg agcactggca | 600 |

| | |
|---|---|
| gttctgaaag cagcactgaa ctctcagcag ggcgaacctt ggcagacgat ccgagttatc | 660 |
| tctgaatact accctgacga ctctggcctg ttctctcctc tgctgctgaa cgttgttaaa | 720 |
| ctgaaccctg gcgaagcaat gttcctgttc gcagaaacgc ctcacgcata cctgcagggc | 780 |
| gttgcactgg aagttatggc aaactctgac aacgttctgc gagcaggcct gacgcctaaa | 840 |
| tacatcgaca tccctgaact ggttgcaaac gttaaattcg aacctaaacc tgcaggcgaa | 900 |
| ctgctgacgg cacctgttaa atctggcgca gaactggact ccctatccc tgttgacgac | 960 |
| ttcgcattct ctctgcacga cctggcactg caggaaacgt ctatcggcca gcactctgca | 1020 |
| gcaatcctgt tctgcgttga aggcgaagca gttctgcgaa agacgaaca gcgactggtt | 1080 |
| ctgaaacctg gcgaatctgc attcatcggc gcagacgaat ctcctgttaa cgcatctggc | 1140 |
| acgggccgac tggcacgagt ttacaacaaa ctgtaa | 1176 |

<210> SEQ ID NO 29
<211> LENGTH: 1176
<212> TYPE: DNA
<213> ORGANISM: Artificial Sequence
<220> FEATURE:
<223> OTHER INFORMATION: Coding sequence for manA4

<400> SEQUENCE: 29

| | |
|---|---|
| atgcaaaagc taataaattc cgtccaaaat tatgcctggg gatccaagac cgccctaacc | 60 |
| gagctatatg gaatagccaa tccacaacaa caaccaatgg ccgagctatg gatgggagcc | 120 |
| catccaaagt cctcctcccg gataaccacc gccaatggag agaccgtctc cctacgggat | 180 |
| gccatagaga agaataagac cgccatgcta ggagaggccg tcgccaatcg gtttggagag | 240 |
| ctaccatttc tatttaaggt cctatgtgcc gcccaaccac tatccataca agtccatcca | 300 |
| aataagcgga attccgagat aggatttgcc aaggagaatg ccgccggaat accaatggat | 360 |
| gccgccgagc ggaattataa ggatccaaat cataagccag agctagtctt tgccctaacc | 420 |
| ccatttctag ccatgaatgc ctttcgggag ttttccgata tagtctccct actacaacca | 480 |
| gtcgccggag cccattccgc catagcccat tttctacaag tcccaaatgc cgagcggcta | 540 |
| tcccaactat tgcctcccct actaaatatg caaggagagg agaagtcccg ggccctagcc | 600 |
| gtcctaaagg ccgccctaaa ttcccaacaa ggagagccat ggcaaaccat acgggtcata | 660 |
| tccgagtatt atccagatga ttccggacta ttttccccac tactactaaa tgtcgtcaag | 720 |
| ctaaatccag gagaggccat gtttctattt gccgagaccc cacatgccta tctacaagga | 780 |
| gtcgccctag aggtcatggc caattccgat aatgtcctac gggccggact aaccccaaag | 840 |
| tatatagata taccagagct agtcgccaat gtcaagtttg agccaaagcc agccggagag | 900 |
| ctactaaccg ccccagtcaa gtccggagcc gagctagatt ttccaatacc agtcgatgat | 960 |
| tttgcctttt ccctacatga tctagcccta agagacct ccataggaca acattccgcc | 1020 |
| gccatactat tttgtgtcga gggagaggcc gtcctacgga aggatgagca acggctagtc | 1080 |
| ctaaagccag gagagtccgc ctttataggg gccgatgagt ccccagtcaa tgcctccgga | 1140 |
| accggacggc tagcccgggt ctataataag ctatag | 1176 |

<210> SEQ ID NO 30
<211> LENGTH: 1176
<212> TYPE: DNA
<213> ORGANISM: Artificial Sequence
<220> FEATURE:
<223> OTHER INFORMATION: Coding sequence for manA4b

<400> SEQUENCE: 30

```
atgcaaaagc taataaattc cgtccaaaat tatgcctggg gatccaagac cgccctaacc      60
gagctatatg gaatagccaa tccacaacaa caaccaatgg ccgagctatg gatgggagcc     120
catccaaagt cctcctcccg gataaccacc gccaatggag agaccgtctc cctacgggat     180
gccatagaga agaataagac cgccatgcta ggagaggccg tcgccaatcg gtttggagag     240
ctaccatttc tatttaaggt cctatgtgcc gcccaaccac tatccataca agtccatcca     300
aataagcgga attccgagat aggatttgcc aaggagaatg ccgccggaat accaatggat     360
gccgccgagc ggaattataa ggatccaaat cataagccag agctagtctt tgccctaacc     420
ccatttctag ccatgaatgc ctttcgggag ttttccgata tagtctccct actacaacca     480
gtcgccggag cccattccgc catagcccat tttctacaag tcccaaatgc cgagcggcta     540
tcccaactat ttgcctccct actaaatatg caaggagagg agaagtcccg ggccctagcc     600
gtcctaaagg ccgccctaaa ttcccaacaa ggagagccat ggcaaaccat acgggtcata     660
tccgagtatt atccagatga ttccggacta ttttccccac tactactaaa tgtcgtcaag     720
ctaaatccag gagaggccat gtttctattt gccgagaccc cacatgccta tctacaagga     780
gtcgccctag aggtcatggc caattccgat aatgtcctac gggccggact aaccccaaag     840
tatatagata taccagagct agtcgccaat gtcaagtttg agccaaagcc agccggagag     900
ctactaaccg ccccagtcaa gtccggagcc gagctagatt ttccaatacc agtcgatgat     960
tttgcctttt ccctacatga tctagcccta caagagacct ccataggaca acattccgcc    1020
gccatactat tttgtgtcga gggagaggcc gtcctacgga aggatgagca acggctagtc    1080
ctaaagccag gagagtccgc ctttatagga gccgatgagt ccccagtcaa tgcctccgga    1140
accggacggc tagcccgggt ctataataag ctatag                              1176
```

<210> SEQ ID NO 31
<211> LENGTH: 1176
<212> TYPE: DNA
<213> ORGANISM: Artificial Sequence
<220> FEATURE:
<223> OTHER INFORMATION: Coding sequence for manA4c

<400> SEQUENCE: 31

```
atgcaaaagc taataaattc cgtccaaaat tatgcctggg gatccaagac cgccctaacc      60
gagctatatg gaatagccaa tccacaacaa caaccaatgg ccgagctatg gatgggagcc     120
catccaaagt cctcctcccg gataaccacc gccaatggag agaccgtctc cctacgggat     180
gccatagaga agaataagac cgccatgcta ggagaggccg tcgccaatcg gtttggagag     240
ctaccatttc tatttaaggt cctatgtgcc gcccaaccac tatccataca agtccatcca     300
aataagcgga attccgagat aggatttgcc aaggagaatg ccgccggaat accaatggat     360
gccgccgagc ggaattataa ggatccaaat cataagccag agctagtctt tgccctaacc     420
ccatttctag ccatgaatgc ctttcgggag ttttccgata tagtctccct actacaacca     480
gtcgccggag cccattccgc catagcccat tttctacaag tcccaaatgc cgagcggcta     540
tcccaactat ttgcctccct actaaatatg caaggagagg agaagtcccg ggccctagcc     600
gtcctaaagg ccgccctaaa ttcccaacaa ggagagccat ggcaaaccat acgggtcata     660
tccgagtatt atccagatga ttccggacta ttttccccac tactactaaa tgtcgtcaag     720
ctaaatccag gagaggccat gtttctattt gccgagaccc cacatgccta tctacaagga     780
gtcgccctag aggtcatggc caattccgat aatgtcctac gggccggact aaccccaaag     840
```

```
tatatagata taccagagct agtcgccaat gtcaagtttg agccaaagcc agccggagag      900
ctactaaccg ccccagtcaa gtccggagcc gagctagatt ttccaatacc agtcgatgat      960
tttgcctttt ccctacatga tctagcccta caagagacct ccataggaca acattccgcc     1020
gccatactat tttgtgtcga gggagaggcc gtcctacgga aggatgagca acggctagtc     1080
ctaaagccag gagagtccgc ctttatagga gccgatgagt ccccagtcaa tgcctccgga     1140
accggacggc tagcccgggt ctataataag ctatag                              1176
```

<210> SEQ ID NO 32
<211> LENGTH: 75
<212> TYPE: DNA
<213> ORGANISM: Artificial Sequence
<220> FEATURE:
<223> OTHER INFORMATION: 5' utr

<400> SEQUENCE: 32

```
aggttacttc atgcgggttt cttggtttaa tacctcccat tgatctccac attgaaacag       60
ggcttgatac atatg                                                       75
```

<210> SEQ ID NO 33
<211> LENGTH: 31
<212> TYPE: DNA
<213> ORGANISM: Artificial Sequence
<220> FEATURE:
<223> OTHER INFORMATION: 5' utr promoter

<400> SEQUENCE: 33

```
ctccacattg aaacagggct tgatacatat g                                     31
```

<210> SEQ ID NO 34
<211> LENGTH: 1158
<212> TYPE: DNA
<213> ORGANISM: Artificial Sequence
<220> FEATURE:
<223> OTHER INFORMATION: Coding sequence for ova_origOptAcc

<400> SEQUENCE: 34

```
atgggctcaa tcggcgcagc atcaatggaa ttctgcttcg acgttttcaa agaactgaaa       60
gttcaccacg caaacgaaaa catcttctac tgccccatcg caatcatgtc agcactggca      120
atggtttacc tgggcgcaaa agactcaacg cgaacgcaga tcaacaaagt tgttcgattc      180
gacaaactgc ccggcttcgg cgactcaatc gaagcacagt gcggcacgtc agttaacgtt      240
cactcatcac tgcgagacat cctgaaccag atcacgaaac ccaacgacgt ttactcattc      300
tcactggcat cacgactgta cgcagaagaa cgataccccca tcctgcccga atacctgcag      360
tgcgttaaag aactgtaccg aggcggcctg gaacccatca acttccagac ggcagcagac      420
caggcacgag aactgatcaa ctcatggggtt gaatcacaga cgaacggcat catccgaaac      480
gttctgcagc cctcatcagt tgactcacag acgcaatgg ttctggttaa cgcaatcgtt      540
ttcaaaggcc tgtgggaaaa aacgttcaaa gacgaagaca cgcaggcaat gcccttccga      600
gttacggaac aggaatcaaa acccgttcag atgatgtacc agatcggcct gttccgagtt      660
gcatcaatgg catcagaaaa aatgaaaatc ctggaactgc ccttcgcatc aggcacgatg      720
tcaatgctgg ttctgctgcc cgacgaagtt tcaggcctgg aacagctgga atcaatcatc      780
aacttcgaaa aactgacgga atggacgtca tcaaacgtta tggaagaacg aaaaatcaaa      840
gtttacctgc ccgaatgaa aatggaagaa aaatacaacc tgacgtcagt tctgatggca      900
atgggcatca cggacgtttt ctcatcatca gcaaacctgt caggcatctc atcagcagaa      960
```

```
tcactgaaaa tctcacaggc agttcacgca gcacacgcag aaatcaacga agcaggccga    1020
gaagttgttg gctcagcaga agcaggcgtt gacgcagcat cagtttcaga agaattccga    1080
gcagaccacc ccttcctgtt ctgcatcaaa cacatcgcaa cgaacgcagt tctgttcttc    1140
ggccgatgcg tttcaccc                                                  1158
```

<210> SEQ ID NO 35
<211> LENGTH: 1158
<212> TYPE: DNA
<213> ORGANISM: Artificial Sequence
<220> FEATURE:
<223> OTHER INFORMATION: Coding sequence for ovasyn

<400> SEQUENCE: 35

```
atgggcagca ttggagcagc ttccatggaa ttctgcttcg acgtgttcaa agagctgaaa      60
gtccaccacg ctaacgaaaa catcttctat tgtccgatcg ccattatgag cgccctggca    120
atggtttatc tgggtgccaa agattctacc cgtacacaga ttaacaaagt ggtccgcttc    180
gacaaactgc ctggttttgg tgatagcatc gaggcacagt gtggtacaag tgtgaacgtc    240
cattctagcc tgcgtgatat tctgaatcag attacgaaac cgaacgacgt gtattccttt    300
tcactggcca gtcgtctgta tgccgaagaa cgttatccta ttctgccgga gtatctgcaa    360
tgcgtgaaag aactgtatcg tggcggtctg gaaccaatca attttcaaac ggccgctgat    420
caagcacgtg aactgattaa cagttgggtg gaaagtcaga ccaatggcat tatccgtaat    480
gtgctgcagc ctagcagtgt tgattctcag acggcaatgg tcctggttaa cgctattgtg    540
tttaaaggcc tgtgggagaa acattcaaa gacgaggata cccaagcaat gcctttccgt    600
gttaccgagc aggaaagcaa acctgttcag atgatgtatc aaattgggct gttccgtgtg    660
gcaagcatgg catccgaaaa aatgaaaatc ctggagctgc cttttgctag tggtacaatg    720
agcatgctgg ttctgctgcc agatgaagtt tcaggtctgg agcaactgga aagcatcatc    780
aacttcgaga aactgaccga gtggacctct tctaacgtga tggaggagcg taaaatcaaa    840
gtctatctgc ctcgtatgaa aatggaagag aaatataacc tgacctccgt gctgatggct    900
atggggatta ctgacgtgtt tagcagtagc gccaatctga gtgggatttc aagcgctgag    960
tctctgaaaa tctctcaggc cgttcatgcc gctcatgccg aaatcaatga agccggtcgt   1020
gaagtcgtgg gaagtgctga agccggggtg gatgccgctt ctgttagcga agaatttcgt   1080
gccgatcacc cgtttctgtt ctgtatcaaa cacattgcta ccaacgccgt actgtttttt   1140
ggacgctgtg tgagcccg                                                 1158
```

<210> SEQ ID NO 36
<211> LENGTH: 1158
<212> TYPE: DNA
<213> ORGANISM: Artificial Sequence
<220> FEATURE:
<223> OTHER INFORMATION: Coding sequence for ova_orig5050

<400> SEQUENCE: 36

```
atgggctcaa tcggcgctgc ttccatggaa ttttgttttg acgtattcaa agaactgaaa      60
gttcaccatg ccaacgaaaa catcttctat tgtccaatcg ctatcatgtc cgccctggca    120
atggtatacc tgggcgccaa agactcaaca aggacgcaaa tcaataaggt ggttcgattt    180
gacaagctgc ccggcttcgg tgactcgatc gaggcgcagt gcgggacctc agttaatgtt    240
cactcatcac tgcgcgatat tctgaatcag attacgaaac ctaatgatgt gtactcgttc    300
tcattggcat ctcgactata cgcagaagag cgctatccga tcttacccga gtacttgcaa    360
```

```
tgcgtgaaag agctttaccg aggggggcctg gaaccgatca attttcagac tgctgccgac    420
caagctcgag agcttattaa ctcttgggtt gaatcacaaa caaacggaat catccgtaat    480
gtactgcagc cctcttcagt ggactcacaa actgccatgg tcttggtaaa tgcgatcgta    540
tttaaaggtt tgtgggagaa gactttcaaa gacgaagaca cacaagctat gccgttccga    600
gttacggaac aagagtcaaa gcctgttcaa atgatgtatc aaatcggctt attccgagta    660
gcatcgatgg caagcgaaaa aatgaagatc ctggagctgc ctttcgcatc agggacgatg    720
tcaatgttgg tattactccc tgatgaagtc tcaggtctgg aacagctgga gtctattatc    780
aacttcgaaa aactgaccga atggacttca tcgaatgtta tggaagaacg caaaatcaag    840
gtgtacttgc cccgaatgaa gatggaggaa aaatataatc tgactagtgt tctgatggcg    900
atggggatca cagacgtatt ttcatcgtct gctaatttga gtggaatctc atcggctgag    960
tcgctaaaga tctcacaagc tgtgcacgcg gcacatgctg agatcaacga ggcggggcga   1020
gaagtagttg gtagtgctga agcgggggtt gacgcagcct cagtatcgga ggaattccgt   1080
gccgatcacc ccttcttatt ttgcatcaag cacattgcaa caaacgccgt cttattcttt   1140
gggcgatgtg tttcccca                                                 1158

<210> SEQ ID NO 37
<211> LENGTH: 1158
<212> TYPE: DNA
<213> ORGANISM: Artificial Sequence
<220> FEATURE:
<223> OTHER INFORMATION: Coding sequence for ova_orig

<400> SEQUENCE: 37
atgggctcca tcggcgcagc aagcatggaa ttttgttttg atgtattcaa ggagctcaaa     60
gtccaccatg ccaatgagaa catcttctac tgccccattg ccatcatgtc agctctagcc    120
atggtatacc tgggtgcaaa agacagcacc aggacacaga taaataaggt tgttcgcttt    180
gataaacttc caggattcgg agacagtatt gaagctcagt gtggcacatc tgtaaacgtt    240
cactcttcac ttagagacat cctcaaccaa atcaccaaac caatgatgt ttattcgttc    300
agccttgcca gtagacttta tgctgaagag agatacccaa tcctgccaga atacttgcag    360
tgtgtgaagg aactgtatag aggaggcttg gaacctatca actttcaaac agctgcagat    420
caagccagag agctcatcaa ttcctgggta gaaagtcaga caaatggaat tatcagaaat    480
gtccttcagc caagctccgt ggattctcaa actgcaatgg ttctggttaa tgccattgtc    540
ttcaaaggac tgtgggagaa acatttaag gatgaagaca cacaagcaat gcctttcaga    600
gtgactgagc aagaaagcaa acctgtgcag atgatgtacc agattggttt atttagagtg    660
gcatcaatgg cttctgagaa aatgaagatc ctggagcttc catttgccag tgggacaatg    720
agcatgttgg tgctgttgcc tgatgaagtc tcaggccttg agcagcttga gagtataatc    780
aactttgaaa aactgactga atggaccagt tctaatgtta tggaagagag gaagatcaaa    840
gtgtacttac ctcgcatgaa gatggaggaa aaatacaacc tcacatctgt cttaatggct    900
atgggcatta ctgacgtgtt tagctcttca gccaatctgt ctggcatctc ctcagcagag    960
agcctgaaga tatctcaagc tgtccatgca gcacatgcag aaatcaatga agcaggcaga   1020
gaggtggtag ggtcagcaga ggctggagtg gatgctgcaa gcgtctctga agaatttagg   1080
gctgaccatc cattcctctt ctgtatcaag cacatcgcaa ccaacgccgt tctcttcttt   1140
ggcagatgtg tttcccct                                                 1158
```

<210> SEQ ID NO 38
<211> LENGTH: 1158
<212> TYPE: DNA
<213> ORGANISM: Artificial Sequence
<220> FEATURE:
<223> OTHER INFORMATION: Coding sequence for ova_origOptSpeed

<400> SEQUENCE: 38

```
atgggaagca taggcgcagc ttccatggaa ttttgcttcg acgtatttaa ggagctaaag      60
gtccatcatg ccaatgagaa tatattttat tgtccaatag ccataatgtc cgccctagcc     120
atggtctatc taggagccaa ggattccacc cggacccaaa taaataaggt cgtccggttt     180
gataagctac caggatttgg agattccata gaggcccaat gtggaacctc cgtcaatgtc     240
cattcctccc tacgggatat actaaatcaa ataaccaagc caaatgatgt ctattccttt     300
tccctagcct cccggctata tgccgaggag cggtatccaa tactaccaga gtatctacaa     360
tgtgtcaagg agctatatcg gggaggacta gagccaataa attttcaaac cgccgccgat     420
caagcccggg agctaataaa ttcctgggtc gagtcccaaa ccaatggaat aatacggaat     480
gtcctacaac catcctccgt cgattcccaa accgccatgg tcctagtcaa tgccatagtc     540
tttaagggac tatgggagaa gacctttaag gatgaggata cccaagccat gccatttcgg     600
gtcaccgagc aagagtccaa gccagtccaa atgatgtatc aaataggact atttcgggtc     660
gcctccatgg cctccgagaa gatgaagata ctagagctac catttgcctc cggaaccatg     720
tccatgctag tcctactacc agatgaggtc tccggactag agcaactaga gtccataata     780
aattttgaga agctaaccga gtggacctcc tccaatgtca tggaggagcg gaagataaag     840
gtctatctac cacggatgaa gatggaggag aagtataatc taacctccgt cctaatggcc     900
atgggaataa ccgatgtctt ttcctcctcc gccaatctat ccggaatatc ctccgccgag     960
tccctaaaga tatcccaagc cgtccatgcc gcccatgccg agataaatga ggccggacgg    1020
gaggtcgtcg gatccgccga ggccggagtc gatgccgcct ccgtctccga ggagtttcgg    1080
gccgatcatc catttctatt ttgtataaag catatagcca ccaatgccgt cctattttt     1140
ggacggtgtg tctcccca                                                  1158
```

CODON OPTIMIZATION

CROSS-REFERENCE TO RELATED APPLICATION

This application is the U.S. national stage application of International Patent Application No. PCT/EP2017/081685, filed Dec. 6, 2017.

The Sequence Listing for this application is labeled "Seq-List.txt" which was created on May 31, 2019 and is 35 KB. The entire content of the sequence listing is incorporated herein by reference in its entirety.

TECHNICAL FIELD OF THE INVENTION

The present invention relates to methods and systems for determining an optimized nucleotide sequence encoding a predetermined amino acid sequence. In particular, the present invention relates to methods and systems wherein a nucleotide sequence is optimized for expression of an encoded protein in a host cell.

BACKGROUND OF THE INVENTION

Optimizing protein translation for (synthetic) gene expression is a complex task. Conventionally, improvement of protein synthesis has been approached by replacing rarely used codons by the target organism's preferred codons. However, this strategy does not always yield the best results.

The genetic code is redundant with up to six synonymous codons encoding the same amino acid. Codon choice affects both cellular protein levels as well as the fitness of whole organisms as studied in bacteria, e.g. *Escherichia coli* or *Salmonella enterica* serovar Typhimurium, eukaryotic microorganisms such as *Saccharomyces cerevisiae* as well as in mammalian or human cell lines such as HepG2 or HEK293.

There are marked differences in codon choice between organisms, which generally mandates adequate codon adaptation to the target organism for artificially transferred genes. As differences in codon choice are particularly pronounced in highly expressed genes (Hershberg, Ruth, and Dmitri A. Petrov. "Selection on codon bias." Annual review of genetics 42 (2008): 287-299) it is therefore generally assumed that codon choice—or codon bias—in highly expressed genes is under selection pressure and in this way "optimal". Therefore, optimal codon choice for an organism is largely determined through imitation of codon choice in the organism's highly expressed genes. The most prominent measure of codon optimality or adaptation to an organism's highly expressed genes is the codon adaptation index (CAI) being accompanied by a plethora of related indices (Nucl. Acid Res. 1987, 15 (3), 1281-1295). These indices are valuable and known measures of "codon optimality" as adaptation of codon choice to that of highly expressed genes often correlates with increased levels of protein expression as well as an overall increase in an organism's fitness which may become evident through increased growth rates.

This is a key finding for many biotechnological applications and in particular to artificial or synthetic gene transfer which will generally not result in sufficient protein yield if the codon usage of transferred genes were not adapted to that of the target organisms (highly expressed genes).

For example, DE 102 60 805 A1 relates to a method for optimizing a nucleotide sequence for the purpose of expression of a protein on the basis of the amino acid sequence of said protein.

In addition, US 2014/0244228 A1 relates to a method of optimization of a nucleotide coding sequence coding for an amino acid sequence, wherein the nucleotide coding sequence is optimized for expression in a host cell.

Furthermore, US 2011/0081708 A1 relates to recombinant protein expression in bacterial, yeast, insect or mammalian cells, and in particular, to a system and a method for sequence optimization for improved recombinant protein expression using a particle swarm optimization algorithm.

Algorithmically, this is implemented in a variety of commonly used software tools (such as e.g. GeneOptimizer (GeneArtAG, LifeTechnologies), Gene Designer (DNA 2.0 Inc., BMC Bioinformatics 2006, 7:285), OPTIMIZER (Nuc. Acid. Res. 2007, 35, W126-W131), QPSOBT (J. Bioinf. and Seq. Anal. 2010, 2(2), 25-29), Visual Gene Developer (BMC Bioinformatics, 2011, 12, 340), JCat (Nucl. Acid Res. 2005, 33 W526-W531). Although this is the current state of the art, there is a serious drawback of this method: As codon adaptation to highly expressed genes is a purely heuristic measure it does not provide a deeper understanding of the underlying processes and does not answer the question what determines optimality in a context dependent and mechanistic fashion. As a consequence this heuristic codon optimization repeatedly causes unexpected or suboptimal outcomes.

Additionally to commonly used indices for codon optimization, the present invention comprises a mechanistical model for simulating the translation process. In general, there are several mechanistic models which study the translation dynamics of proteins by following the ribosome dynamics on the mRNA (e.g. Dominique Chu, James Thompson, and Tobias von der Haar. Charting the dynamics of translation. Biosystems, 119:1-9, May 2014. doi: 10.1016/j.biosystems.2014.02.005. URL; S. Reuveni, I. Meilijson, M. Kupiec, E. Ruppin, and T. Tuller. Genome-scale analysis of translation elongation with a ribosome flow model. PLoS Comput. Biol., 7 (9):e1002127, 2011; T. Tuller, A. Carmi, K. Vestsigian, S. Navon, Y. Dorfan, J. Zaborske, T. Pan, O. Dahan, I. Furman, and Y. Pilpel. An evolutionarily conserved mechanism for controlling the efficiency of protein translation. Cell, 141(2):344-354, 2010; Hadas Zur and Tamir Tuller. Strong association between mRNA folding strength and protein abundance in *S. cerevisiae*. EMBO Rep., 13(3):272-277, 2012. URL; Hadas Zur and Tamir Tuller. Rfmapp: ribosome flow model application. Bioinformatics, 28(12):1663-1664, June 2012. doi: 10.1093/bioinformatics/bts185. URL Hadas Zur and Tamir Tuller. Rfmapp: ribosome flow model application. Bioinformatics, 28(12):1663-1664, June 2012. doi: 10.1093/bioinformatics/bts185. URL Marlena Siwiak, Piotr Zielenkiewicz, Transimulation—Protein Biosynthesis Web Service PLoS One 8(9) e73943, 2013) being variants of a class of models referred to as Totally Asymmetric Exclusion Process (TASEP) (Tobias von der Haar. Mathematical and computational modelling of ribosomal movement and protein synthesis: an overview. Computational and structural biotechnology journal, 1(1):1-7, 2012)): after attachment of ribosomes to mRNA (initiation step), the ribosomes can only move forward to successively translate codons into amino acids (elongation step, totally asymmetric) while multiple ribosomes cannot overtake one another (spatially exclusive).

Moreover, WO 2016/112142 A1 relates to a free-energy based model of translation elongation to predict and optimize protein yield and aggregation. In particular, the procedures to derive ribosome wait times are based on the hypothesis that a slight displacement of ribosomes leads to longer ribosome waiting times, which is modelled in a free-energy-based framework. In addition, new codons with probabilities proportional to the corresponding tRNA abundance (or a "user predefined value") are proposed, wherein the proposals are accepted depending on a free-energy-signal (phase angle). The target functions used are ribosome displacement, translation bottlenecks and total wait cycle. The described optimization procedure is a deterministic optimization.

US 2013/149699 A1 relates to compositions and methods that are provided for modulating the translation kinetics of an mRNA, or a region or domain of an mRNA, by appropriate selection of codons, particularly with respect to "wobble" codon pairs. The codons are selected based on a "kinetic map" which lists codon specific elongation rates (experimentally determined, approximated by tRNA repertoire, "wobble codon pairs" or by other means). "Harmonized sequences" try to reproduce the kinetic map of a sequence from the source to the target organism which is considered optimal.

Amanda M. Lanza et al.: "A condition-specific codon optimization approach for improved heterologous gene expression in Saccharomyces cerevisiae", BMC Systems Biology 2014, 8:33 generally relates to codon optimization. In contrast to traditional techniques in which codon usage is adapted to codon usage bias (CUB) seen in highly expressed genes Lanza et al. add additional information on context dependent CUB (cell conditions, growth conditions, . . . ) and codon pairing.

Armando Fernandes et. al.: "Improving Protein Expression Prediction Using Extra Features and Ensemble Averaging", PLOS ONE, vol. 1, no. 3, 2016 relates to a method for improvement of machine learning models capable of predicting protein expression levels based on their codon encoding.

EP 2 545 176 A1 relates to an isolated polynucleotide encoding a human polypeptide having a predetermined amino acid sequence, as well as to a method of generating a polypeptide.

DESCRIPTION OF THE INVENTION

In view of the above mentioned drawbacks of the prior art, it is an object of the present invention to provide a non-heuristic codon optimization based on biological translation dynamics. Further, it is an object to allow for the provision of nucleotide sequence encoding a predetermined amino acid sequence, the nucleotide sequence having the desired expression properties, e.g. protein expression efficiency or alternative target functions as for example translation accuracy.

The object is achieved with the features of the independent claims. The dependent claims relate to further aspects of the invention.

In one aspect of the present invention a method for determining an optimized nucleotide sequence encoding a predetermined amino acid sequence is provided, wherein the nucleotide sequence is optimized for expression in a host cell. The method comprises the steps of: (a) generating a plurality of candidate nucleotide sequences encoding the predetermined amino acid sequence; (b) obtaining a sequence score based on a scoring function based on a plurality of sequence features that influence protein expression in the host cell using a statistical machine learning algorithm, wherein the plurality of sequence features comprises one or more sequence features selected from the group consisting of protein per time, average elongation rate and accuracy for each of the plurality of candidate nucleotide sequences of step (a); and (c) determining the candidate nucleotide sequence with optimized protein expression in the host cell as the optimized nucleotide sequence.

According to a preferred embodiment, the plurality of sequence features comprises protein per time and average elongation rate and/or accuracy. That is, the plurality of sequence features comprises at least one of the following combinations: a) protein per time and average elongation rate, b) protein per time and accuracy and c) protein per time and average elongation rate and accuracy. In other words, in a preferred embodiment of the method of the invention, the plurality of sequence features comprises protein per time and at least one other sequence feature.

Preferably the candidate nucleotide sequences with the highest sequence score is attributed to the highest predicted protein expression in the host cell, and the nucleotide sequence with the lowest sequence score is attributed to the lowest predicted protein expression in the host cell.

The mechanistic nature of the score allows for additional consideration of sequence target functions as for example translation accuracy.

Hence, the skilled person can adapt the scoring function, in particular by assigning weights to the individual sequence features. This allows for specific optimization of some aspects, for example by prioritizing translation-accuracy over other features to achieve highly accurate translation.

The present invention introduces a codon-specific elongation model (COSEM) for prediction and adaptation of optimal codon usage mainly based on translation speed (protein per time (COSEM current) and average elongation rate) and accuracy. The model is integrated with further relevant covariates into a protein expression score (in the following also named "sequence score") which is used to confirm the optimization approach with proteome data from widely used prokaryotic, eukaryotic, and human expression systems. In addition, the multi-parameter algorithm cannot only be used for increasing protein yield but also encompasses fine-tuning protein expression, including decreasing the protein yield, e.g. for synthetic attenuated virus engineering. Hence, the term "optimization" may relate to increasing the expression or to decrease the expression, preferably to a desired level.

The term "sequence features" refers to features or properties of a sequence that are given by the sequence. In a preferred embodiment the sequence features are features of the candidate sequence that influence expression of the nucleotide sequence in an amino acid sequence. Such features include the folding behavior of a nucleotide sequence. The folding of an mRNA at its 5'-end into secondary structures may hinder ribosome-initiation and may therefore be considered. Some of the sequence features may differ in their influence on expression from host organism to host organism. For example the GC content (referring to the portion of nucleotides being G or C rather than A or T) is varying from organism to organism. Hence, the skilled person will acknowledge that the sequence features of the method have to be considered according to the host organism. For instance, if the GC content of the host organism is high, e.g. over 50% or higher, the GC content of the optimized nucleotide sequence encoding the predetermined amino acid sequence should be selected as to being in the same range as the average GC content of the host organism. On the other hand, if the candidate sequence has a high GC content, e.g. over 50% or higher, preferably as high as 80%, the expression might be less efficient in host organisms that contains a low GC content, e.g. 40% or lower, preferably as low as 20%. The skilled person is in the position to determine the GC content of a host organism and to evaluate a candidate sequence accordingly, and in particular the GC3 content, i.e. the fraction of G and C at the third positions of the codons.

The sequence features selected from the group consisting of protein per time, average elongation rate and accuracy may be based on a mechanistic model of protein translation.

The plurality of candidate nucleotide sequences may comprise generating at least 100 candidate nucleotide sequences, preferably at least 250 candidate nucleotide sequences, more preferably at least 500 candidate nucleotide sequences. However, in a preferred embodiment, the number of candidate nucleotide sequences for said plurality of candidate is the number at which a maximum score of candidate sequences reaches a predetermined equilibrium value (cf. step d1)), see infra.

The plurality of sequence features may further comprise one or more sequence features selected from the group consisting of GC3 content, rate of slowest stretch of 10 codons, 5' folding energy, and 5' number of mRNA hairpins.

The term "GC3 content" relates the fraction of guanine and cytosine in the third codon positions.

Rate of slowest codon (bottleneck index) relates to the slowest elongation rate of a 5 to 15 codon sliding window, preferably a 10 codon sliding window (see JiaJia Dong, Beate Schmittmann, and Royce K P Zia (2004). Inhomogeneous exclusion processes with extended objects: The effect of defect locations. Physical Review E, 76(5):051113).

"5' folding energy" preferably relates to the folding energy of first 10 to 50 codons, more preferred the first 30 codons. Calculation of the folding energy can be performed as described previously (see Wanjun Gu, Tong Zhou, and Claus 0. Wilke (2010). A universal trend of reduced mRNA stability near the translation initiation site in prokaryotes and eukaryotes. PLoS Comput Biol, 6(2):e1000664, incorporated herein by reference).

"5' number of hairpins" relates to the number of hairpins within the first 10 to 50 codons, preferably within the first 30 codons.

"Hairpin" denotes a stem-loop intramolecular base pairing that can occur in single-stranded RNA. It occurs when two regions of the same strand, usually complementary in nucleotide sequence when read in opposite directions, basepair to form a double helix (also referred to as the stem) that ends in an unpaired loop. Herein, a hairpin preferably denotes a structure of at least 2 pairs of nucleotides forming the stem and 3 to 20 nucleotides forming a loop.

Codon-specific elongation rates and accuracies for translation are preferably calculated by minimizing the kinetic distance between a set of measured in vitro rates and predicted rates compatible with translation in vivo. This has been described and exemplified for *E. coli* before (see Sophia Rudorf and Reinhard Lipowsky (2015). Protein Synthesis in *E. coli*: Dependence of Codon-Specific Elongation on tRNA Concentration and Codon Usage. PLoS ONE, 10(8): 1; and Sophia Rudorf, et al. (2014), Deducing the kinetics of protein synthesis in vivo from the transition rates measured in vitro. PLoS Comput Biol, 10(10): e1003909; both incorporated herein by reference). The skilled person will be able to obtain codon-specific elongation rates and accuracies also for other organism using suited parameters. Preferred parameters include Ribosomal transition rates, Definition of "cognate", Definition of "near cognate", codon usage, ribosomes per cell, eEF1a1 per cell, average cell volume, and overall elongation rate. The skilled person is able to determine these parameters by the information as disclosed in Rudorf and Lipowsky and Rudorf et al.; see above. For some organisms these have been already determined. Examples are given in Table S1, which are preferred herein for the therein recited host cells.

In a preferred embodiment codon specific elongation rates and accuracies are determined as follows: translation of a codon is described by a twelve-state Markov process with twelve independent transition rates. Experimentally determined in vitro values of these transition rates (Kirill B Gromadski and Marina V Rodnina (2004). Kinetic determinants of high-fidelity tRNA discrimination on the ribosome. Mol. Cell, 13(2):191-200; incorporated herein by reference) are used to predict a set of in vivo transition rates compatible with the organism- and growth-rate dependent overall rate of protein synthesis. Furthermore, the codon-specific elongation rates and accuracies depend on the concentrations of free ternary complexes via competition of cognate, near-cognate and non-cognate ternary complexes at the ribosomes' binding sites which are used to estimate the rates in the above mentioned twelve-state Markov process (see Rudorf, S.; Lipowsky, R.: Protein Synthesis in *E. coli*: Dependence of Codon-Specific Elongation on tRNA Concentration and Codon Usage. PLoS One 2015, FIG. 3, Refs. 37-38). Thus, from codon usages and measured or estimated tRNA abundances the concentrations of the above mentioned corresponding ternary complexes are preferably calculated by taking into account the recharging of tRNAs by aminoacyl tRNA synthetases, whereas a simpler model could be based only on tRNA abundances. (Rudorf, S.; Lipowsky, R.: Protein Synthesis in *E. coli*: Dependence of Codon-Specific Elongation on tRNA Concentration and Codon Usage. PLoS One 2015). A detailed listing of preferred codon-specific elongation rates and accuracies for certain organism is found in Tables S7 to S12. Also a list of preferred cognate, near-cognate (possibly missense) or non-cognate codons is given in Tables S1 to S6 for preferred organisms (host cells). For *E. coli* a preferred average initiation is reported 5 min$^{-1}$ for the lac-operon and 4 min$^{-1}$ as median for all *E. coli* genes. A preferred initiation rate for *E. coli* is 100 s$^{-1}$ or larger than 10 s$^{-1}$. For *S. cerevisiae* a preferred median is 2.5 s$^{-1}$ or the range of 1-5 s$^{-1}$. Preferred for human stem cells, e.g. Hela, but also HEK293, the median is 0.06 s$^{-1}$ and preferably larger than 0.01 s$^{-1}$ Preferred drop-off rates for *E. coli*, *S. cerevisiae* and human cell lines have been chosen to 6.6 $10^{-3}$ s$^{-1}$, 9.9 $10^{-3}$ s$^{-1}$ and 1.8 $10^{-3}$ s$^{-1}$, respectively.

The codon optimization procedure of the present invention aims at the optimization of the expression of a protein in a host organism. Accordingly, the skilled person will acknowledge that the sequence features are to be considered with respect to the organism in which the sequence is to be expressed, i.e. the host organism. Accordingly, the sequence features of GC3 content, bottleneck index (average rate of slowest codons), 5' folding energy, 5' number of hairpins, accuracy, average elongation rate, and protein per time (3' current) are preferably considered with respect to the host organism. The determination of these sequence features for a certain organism requires different levels of input data and tools for evaluation. While GC3 content requires only information about a gene's nucleotide sequence and open reading frame as a basis for simple nucleotide counting, the bottleneck index and average elongation rate require additional information about codon specific elongation rates whereas sequence accuracy requires information about codon specific accuracies. Protein per time (COSEM) current requires a mechanistic model and needs information about further biological parameters such as translation initiation and drop-off rates which can potentially be inferred if adequate experimental data are available. 5' folding energy and number of hairpins can be derived in various ways, for example using bio-informatic tools such as RNAfold (Lorenz, Ronny and Bernhart, Stephan H. and Höner zu Siederdissen, Christian and Tafer, Hakim and Flamm, Christoph and Stadler, Peter F. and Hofacker, Ivo L. ViennaRNA Package 2.0 Algorithms for Molecular Biology, 6:1 26, 2011, doi: 10.1186/1748-7188-6-26).

The codon-specific elongation model (COSEM) combines a deep understanding of dynamic features extensively studied in TASEPs with significant improvements in biological realism. Earlier parameter sets are refined to parameterize the model with biologically plausible translation-initiation rates, codon specific elongation rates and accuracies, as well as ribosome drop-off rates. These COSEM parameters are based on concentrations of cognate and near-cognate tRNAs, elongation factors and ribosome sizes and are as such specific for the organism in which the protein is to be expressed. This integration of well studied TASEPs models with biologically relevant parameter sets allows for a determination of the impact of codon choice on protein levels (in terms of COSEM current) and translation accuracy in a mechanistic manner both at initiation and elongation steps. The codon-specific elongation model (COSEM) further facilitates thought experiments which can frame translation dynamics within a more general dynamic picture for example to explain ribosome dynamics. Most importantly, the model is used for the first time to optimize genes in a context dependent manner for accuracy, protein output in addition to further sequence features.

That is, COSEM is the basis of the feature COSEM current (=protein per time) to be considered in the protein expression score. The further feature "average elongation rate" can be directly derived from COSEM parameters, the feature "accuracy" can be derived from codon specific accuracies as complementary COSEM parameters. These three features are combined with further features (e.g. GC3 content) into the protein expression score.

The derivation of sequence features (protein per time, average elongation rate, accuracy, rate of slowest stretch of 12 codons, 5' folding energy of the first 30 codons, 5' number of mRNA hairpins of the first 30 codons, GC3 content, . . . ) is based on various input parameters and models, including a mechanistic model based on host specific measurements for the parameters protein per time, average elongation rate and accuracy.

The optimization of the nucleotide sequence in accordance with the present invention is, thus, predominantly based on parameters of the (to be optimized) sequence, i.e., in particular by the sequence features protein per time, average elongation rate, accuracy, rate of slowest stretch of 12 codons, 5' folding energy of the first 30 codons, 5' number of mRNA hairpins of the first 30 codons, GC3 content. These sequence parameters/features are, of course, measured in a host cell or derived from parameters measured in the host cell in accordance with the experimental evidence of the present invention. Nevertheless, the nature of these features depends on the characteristics of the sequence (to be optimized) itself in the first place.

Moreover, the method of the present invention, inter alia, makes use of the mRNA folding as a potential covariate in the protein expression score while the mechanistic model referred to in the present invention utilizes the collective dynamics of ribosomes on an mRNA.

Indeed, the method of the present invention, in particular, utilizes the feature "COSEM current" or "protein per time and mRNA". This feature represents protein produced per mRNA and time, simultaneously taking collective dynamics of protein translation, i.e., dynamics of ribosomes on mRNA, into account.

The protein expression score may be further improved through the consideration of mRNA transcript levels where available.

In particular, the present invention combines further sequence features as outlined above to obtain a full protein expression score (scoring function), wherein the scoring function at least comprises one or more sequence features selected from the group consisting of protein per time, average elongation rate and accuracy for each of the plurality of candidate nucleotide sequences and preferably other sequence features which influence protein expression.

Preferably, the statistical machine learning algorithm is a boosted generalized additive model (Torsten Hothorn, Peter Buehlmann, Thomas Kneib, Matthias Schmid, and Benjamin Hofner. mboost: Model-based boosting. R package version, pages 2-1, 2012).

That is, according to the boosted generalized additive model the different factors (sequence features) of the scoring function are weighted with component-wise smoothing splines and modeled separately through least square analysis with log-transformed protein abundance data from PaxDb in E. coli, S. cerevisiae and HEK293 and using available data on protein abundance (Mingcong Wang, Manuel Weiss, Milan Simonovic, Gabriele Haertinger, Sabine P Schrimpf, Michael O Hengartner, and Christian von Mering. Paxdb, a database of protein abundance averages across all three domains of life. Molecular & Cellular Proteomics, 11(8): 492-500, 2012) where available, for example.

It turns out that most factors can be approximated as (piece-wise) linear effects within relevant ranges of the sequence feature values.

In general, the protein expression score for a sequence is thus optimized in two phases: a) at every position in a test sequence x the codon that optimizes the elongation rates and possibly the accuracies locally relative to those in the predetermined amino acid sequence and b) for every sequence generated this way, the protein expression score is calculated including a simulation of the codon-specific elongation model. In the end, the sequence with the highest protein expression score (scoring function) may be chosen as the optimal sequence.

In a preferred embodiment of the invention an increase in protein per time (COSEM current), a higher elongation rate, less bottlenecks, higher transcript amount, high accuracy and/or having a not too negative folding energy all contribute to higher expression.

As each amino acid may be encoded by up to 6 different codons, the method comprises the generation of a plurality of candidate nucleotide sequences. It will be readily understood that each candidate nucleotide sequence codes for the same amino acid sequence, i.e. the predetermined amino acid sequence. In order to find an optimized nucleotide sequence, the method preferably uses a plurality of candidate nucleotide sequences that differ in at least one nucleotide while encoding the same amino acid sequence. In principle the plurality of candidate nucleotide sequence shall contain a randomized combination of codons encoding in order to determine which has the desired expression properties. However, in order to have a certain bias in the randomization, the method of the invention weights all codons encoding the amino acid at the respective position according to their organism and codon specific accuracies and elongation rates, i.e. a score for the codon representing its effect on translation accuracy and elongation rates in the host organism.

Hence, in a preferred embodiment, generating a plurality of candidate nucleotide sequences may comprise: (a1) obtaining a local score for each codon encoding a first amino acid of the amino acid sequence, wherein the local score is based on organism and codon specific elongation rates and accuracies in the form of a local scoring function; (b1) picking a random codon encoding the amino acid weighted according to the calculated local score of step (a1); (c1) generating a candidate nucleotide sequence by repeating steps (a1) and (b1) for all remaining amino acids of the amino acid sequence; and (d1) repeating steps (a1) to (c1) to obtain a plurality of scored candidate nucleotide sequences.

Preferably, repeating (a1) to (c1) is stopped when the obtained sequence score of candidate sequences according to step (b) reaches a predetermined equilibrium value. In particular, random sequences may be successively selected as described above. A subsequently selected sequence does not necessarily have to be better than the previous sequence in terms of the respective sequence score. However, the maximum of the sequence score as a function of the amount of sequences generated may reach an "optimal" sequence score, wherein the term "optimal" may be defined by the aforementioned predetermined equilibrium value. Thus, the sequence score may also be referred to as a maximum sequence score. However, the maximum sequence score may be unknown beforehand, which is the reason why one has to revert back to the above mentioned predetermined equilibrium value according to step (b).

Preferably, the amino acid sequence is encoded by a wildtype-sequence from a source organism. The amino acid sequence may also be an artificial sequence which does not naturally occur in nature. The nature of the amino acid sequence is not limited. Examples for artificial amino acid sequences include, without being limiting, fusion sequences or combinations of different protein motifs/domains originating from different proteins. Artificial amino acid sequences may also comprise motifs/domains which are modified compared to the motifs/domains from which they are derived leading to an altered activity (preferably an improved activity) compared to the sequence from which they are derived from.

Before step (a1) the method may perform step (a1i): determining if the wildtype-nucleotide-sequence contains a ramp of slow codons for the source organism, wherein if it contains a ramp of slow codons, a predetermined number of the first codons are not considered in the subsequent steps (a1)-(d1) and the codon optimization is performed from the predetermined number of codons on.

The predetermined equilibrium value in step (d1) may be defined by the coefficient of variation of the maximum score of the last 100 sequences falling below 10%, preferably 5%, and more preferably 1%.

The "predetermined number of first codons" may vary depending on the needs, e.g. on the total length of the sequence and/or the involved organisms. In a preferred embodiment the predetermined number is 10 to 100 codons, preferably 20 to 90 codons, yet more preferably 40 to 60 codons, and in a particular preferred embodiment the predetermined number is 50 codons.

The predetermined number of first codons may be within the range of the first 10 to 100 codons, preferably within the range of the first 20 to 90 codons, more preferably within the range of the first 40 to 60 codons, and most preferably the first 50 codons.

The term "first" in this regard is to be construed as relating to the codons directly following and including the start codon of the nucleotide sequence encoding the predetermined amino acid sequence or downstream from the start codon.

The method may further comprise adapting a relative weighting of sequence features to allow for an optimization with respect to translation accuracy or slow translation for increased time of co-translational folding.

The skilled person will acknowledge that the present inventive method for codon optimization may be performed for generating a nucleotide sequence encoding for a predetermined amino acid sequence and having the desired expression features. However, it may be the case that the optimization procedure starts with an amino acid sequence encoding nucleotide sequence, e.g. obtained from a source organism. Such a "wild-type nucleotide" sequence may be obtained from the host organism, e.g. in order to optimize expression. In this case the source and the host organism are the same. However, in a preferred embodiment of the invention the wild-type-nucleotide sequence is obtained from an organism different of the host organism.

In case the optimization procedure has to start from a (wildtype) nucleotide sequence to be optimized, the first step would be the translation into the thereby encoded amino acid sequence. Based on this amino acid sequence the optimized codon sequence encoding said amino acid sequence is determined according to the invention. Hence, the method may further comprise the following steps which are executed before step (a1i): (a1ii) translating the wildtype-nucleotide-sequence into an encoded amino acid sequence and (a1iii) splitting the wildtype nucleotide sequence into codons according to the encoded amino acid sequence.

When derived from a source organism the wildtype-nucleotide-sequence might contain a ramp of slow codons. Such ramp of slow codons means that the nucleotide sequence contains at its 5' encoding region codons that are suboptimal for expression in the source organism. For yet not identified reasons the presence of such ramp indicates that optimization within the ramp leads to insufficient expression. (Tuller, Tamir, et al. "An evolutionarily conserved mechanism for controlling the efficiency of protein translation." Cell 141.2 (2010): 344-354)). Hence, it is desirable to determine whether a wildtype-nucleotide-sequence contains a ramp of slow codons. In case the wildtype-sequence contains such ramp of slow codons the codons within the ramp are taken as they are and the optimization is performed on the codons downstream of the ramp. The determination if the wildtype-nucleotide-sequence contains a ramp of slow codons may comprise comparing an average codon adaption index, CAI, of the predetermined number of the first codons and an average codon adaption index, CAI, of the subsequent codons of the wildtype-nucleotide-sequence, wherein the CAI is determined with respect to the wildtype-nucleotide-sequence and can be substituted by an average codon-specific elongation rate if codon specific elongation rates are available for the wildtype-nucleotide-sequence.

It may be determined that the wildtype-nucleotide-sequence contains a ramp of slow codons if the average CAI or the average codon-specific elongation rate of the predetermined number of the first codons is different by a predetermined amount within the range of 10-50%, preferably within the range of 20-40% and more preferably by 30% compared to the average CAI or the average codon-specific elongation rate of the subsequent codons of the wildtype-nucleotide-sequence.

Determining the presence of a ramp of slow codons and the average CAI is commonly known by the skilled person (see (Tuller, Tamir, et al. "An evolutionarily conserved mechanism for controlling the efficiency of protein translation." Cell 141.2 (2010): 344-354).

In another aspect of the present invention a system for determining an optimized nucleotide sequence encoding a predetermined amino acid sequence is provided, wherein the nucleotide sequence is optimized for expression in a host cell. The system comprises: a first unit configured to generate a plurality of candidate nucleotide sequences encoding the predetermined amino acid sequence; a second unit configured to obtain a sequence score based on a scoring function based on a plurality of sequence features that influence protein expression in the host cell using a statistical machine learning algorithm, wherein the plurality of sequence features comprises one or more sequence features selected from the group consisting of protein per time, average elongation rate, and accuracy for each of the plurality of candidate nucleotide sequences; and a third unit configured to determine the candidate nucleotide sequence with optimized protein expression in the host cell as the optimized nucleotide sequence.

Preferably, the candidate nucleotide sequences with the highest sequence score is attributed to the highest predicted protein expression in the host cell, and the nucleotide sequence with the lowest sequence score is attributed to the lowest predicted protein expression in the host cell.

In order to generate a plurality of candidate nucleotide sequences the first unit may further be configured to: obtain a local score for each codon encoding a first amino acid of the amino acid sequence, wherein the local score is based on organism codon specific elongation rates and accuracies in the form of a local scoring function based on codon specific elongation rates and accuracies; pick a random codon encoding the amino acid weighted according to the calculated local score; generate a candidate nucleotide sequence by repeating obtaining a local score and picking a random codon for all remaining amino acids of the amino acid sequence; and obtain a plurality of scored candidate nucleotide sequences by repeating obtaining a local score, picking a random codon and generate a candidate nucleotide sequence.

Preferably, the first unit is further configured to stop obtaining scored candidate nucleotide sequences when the obtained (maximum) sequence score of candidate sequences reaches a predetermined equilibrium value.

The first unit may further be configured to determine if the wildtype-nucleotide-sequence contains a ramp of slow codons for the source organism before obtaining a score for each codon encoding the first amino acid of the amino acid sequence, wherein if it contains a ramp of slow codons, a predetermined number of the first codons are not considered, and codon optimization is performed from the predetermined number of codons on.

The first unit may further be configured to adapt a relative weighting of sequence features to allow for a sequence proposal with respect to translation accuracy or slow translation for increased time of co-translational folding.

The first unit is further configured to: translate the wildtype-nucleotide-sequence into an encoded amino acid sequence and split the wildtype-nucleotide-sequence into codons according to the encoded amino acid sequence, wherein the first unit is further configured to execute the translation and the splitting before determining if the wildtype-nucleotide-sequence contains a ramp of slow codons for the source organism.

The second unit may further be configured to determine if the wildtype-nucleotide-sequence contains a ramp of slow codons by comparing an average codon adaption index, CAI, of the predetermined number of the first codons and an average codon adaption index, CAI, of the subsequent codons of the wildtype-nucleotide-sequence, wherein the CAI is determined with respect to the wildtype-nucleotide-sequence and can be substituted by an average codon-specific elongation rate if codon specific elongation rates are available for the wildtype-nucleotide-sequence.

The second unit may further be configured to determine that the wildtype-nucleotide-sequence contains a ramp of slow codons if the average CAI or the average codon-specific elongation rate of the predetermined number of the first codons is different by a predetermined amount within the range of 10-50%, preferably within the range of 20-40% and more preferably by 30% compared to the average CAI or the average codon-specific elongation rate of the subsequent codons of the wildtype-nucleotide-sequence.

The model was validated in the present examples on large scale data sets for *E. coli, S. cerevisiae* and mammal cell lines, such as human cell lines HEK293 showing improved predictive power. In addition, two exemplary genes were chosen, manA and ova, for a more detailed analysis and for which variants for expression in *Salmonella enterica* serovar Typhimurium and comparison of experimentally measured protein expression with theoretical predictions were designed.

Hence, in another aspect the present invention relates to the use of the method according to the present invention for codon optimization of a starting sequence of natural or artificial origin comprising a peptide encoding gene for the expression in a prokaryotic or eukaryotic host cell. The host cell according to the present invention may be chosen according to the needs. It may be chosen from natural occurring or recombinant bacterial cells, fungal cells, plant cells and animal cells. Any host cell or organism may be chosen which is suited for expressing a nucleic acid in order to obtain a thereby encoded protein, such as a prokaryotic or eukaryotic host cell or organism. The host cell or organism preferably may be selected from the group consisting of *Escherichia coli, Saccharomyces cerevisieae*; and mammalian cells, such as Hek293, HepG2 or HeLa. It can also be used in a plethora of other expression systems such as *Pseudomonas fluorescens, Corynebacterium glutamicum, Pichia pastoris, Aspergillus niger, Chlamydomonas reinhardtii, Synechococcus elongatus, Trichoplusia ni, Leishmania major, Mus musculus* and the Chinese Hamster Ovary cell line CHO. The use may be the use for increasing or attenuating expression of the peptide encoding sequence; depending on what is desired. In fact this is one major advantage of the present method, as it makes expression efficiency predictable and thereby provides a tool for obtaining a desired expression level based on codon optimization.

In a further aspect of the present invention a computer program product is provided comprising one or more computer readable media having computer executable instructions for performing the steps of the above described method according to the present invention.

The method and computer programs above are suited to optimize expression of a nucleic acid in a host cell in order to obtain a protein of interest encoded on said nucleic acid. Hence, the present invention also relates to a method for producing a protein of interest comprising the steps of:—introducing a nucleic acid encoding the protein of interest into a host cell; and—incubating said host cell under conditions allowing for expression of said nucleic acid to obtain said protein of interest; wherein said nucleic acid comprises a nucleotide sequence being codon optimized for expression of said protein of interest in said host cell by a method for determining an optimized nucleotide sequence encoding according to the invention. In a preferred embodiment the method for producing a protein of interest comprises the step of determining an optimized nucleotide sequence encoding the amino acid sequence according to the present invention. The skilled person will understand that the determination of the optimized nucleotide sequence is performed before introduction of the nucleic acid into the host cell.

"Expression" refers to transcription and translation occurring within a host cell. The level of expression of a DNA molecule in a host cell may be determined on the basis of either the amount of corresponding mRNA that is present within the cell or the amount of the DNA-encoded protein produced by the host cells. Further detail for the term "expression" within the context of the present invention can be obtained via a review of Sambrook et al. (2012), "Molecular Cloning: A Laboratory Manual", 4$^{th}$ edition, *Cold Spring Harbor Laboratory Press*, ISBN: 978-1-936113-42-2, which is incorporated herein by reference.

Further, it will be understood by the skilled person that the nucleic acid introduced into the host cell comprises the optimized nucleotide sequence such that its sequence is expressed to a protein under the desired conditions. To this end, the nucleic acid may comprise a promoter operatively linked to the optimized nucleotide sequence. In a particular preferred embodiment the nucleic acid introduced comprises an expression cassette. An expression cassette may be a part of an expression vector, such as DNA vector used for cloning and transformation. The expression cassette directs the cell's machinery to make RNA and protein as encoded on the optimized nucleotide sequence. An expression cassette is composed of one or more genes and the sequences controlling their expression. An expression cassette usually comprises: a promoter sequence, an open reading frame coding for the amino acid sequence of a polypeptide (i.e. the nucleotide sequence optimized according to the invention), and optionally a 3'-untranslated region that, in eukaryotes, usually contains a polyadenylation site.

The term "operatively linked" or "operably linked", as used in connection with the present invention, refers to a linkage between one or more expression control sequences and/or the coding region in the nucleic acid, i.e. the optimized nucleotide sequence to be expressed in such a way that expression is achieved under conditions compatible with the expression control sequence, e.g. so that the promoter triggers expression of the nucleotide sequence.

The host cell is preferably selected from the group consisting of prokaryotic or eukaryotic host cells, such as natural occurring or recombinant bacterial cells, fungal cells, plant cells and animal cells, preferably any one of *Escherichia coli*; fungi, such as *Saccharomyces cerevisiae*, and mammalian cells, such as Hek293, HepG2 or HeLa.

Some preferred embodiments are now described with reference to the drawings. For explanation purpose, various specific details are set forth, without departing from the scope of the present invention as claimed.

The phase diagram was generated for a synthetic mRNA of 300 codons length with elongation rate $\langle \omega \rangle$ =60 s−1 and drop-off rate $\gamma$=10−2 s−1. With increasing initiation rate and decreasing termination rate the ribosome density shows a sharp transition from a low (LD) to a high (HD) density regimes with the latter being characterized by ribosome jamming. With a ribosomal footprint of d=10 the transition to the maximum current (MC) regime can be estimated to occur at $$\alpha / \langle \omega \rangle = \beta / \langle \omega \rangle = \frac{1}{\sqrt{d}+1}.$$

As a consequence of ribosome drop-off at a rate $\gamma$ the regime of high ribosome density (HD) and jamming is reduced. Without a bottleneck at the end of mRNA protein translation can be expected to operate in the upper part of the phase diagram with $\beta \approx 1$.

Figure 8:
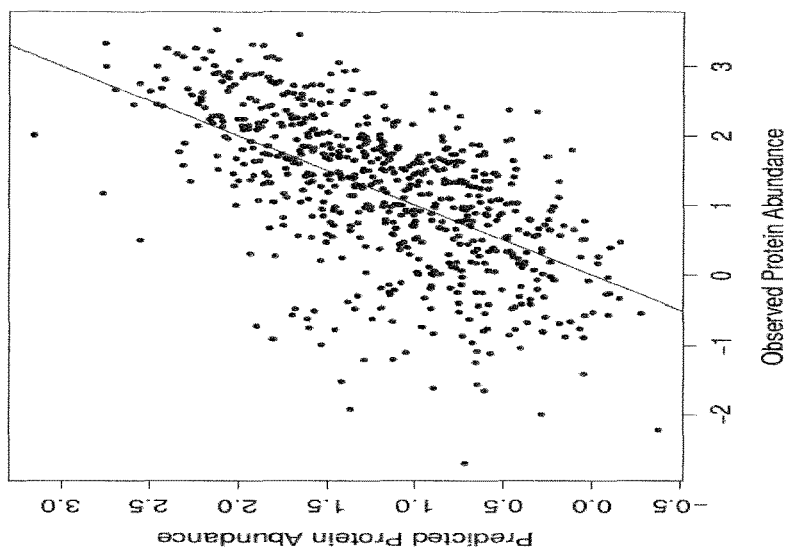
Figure 8:
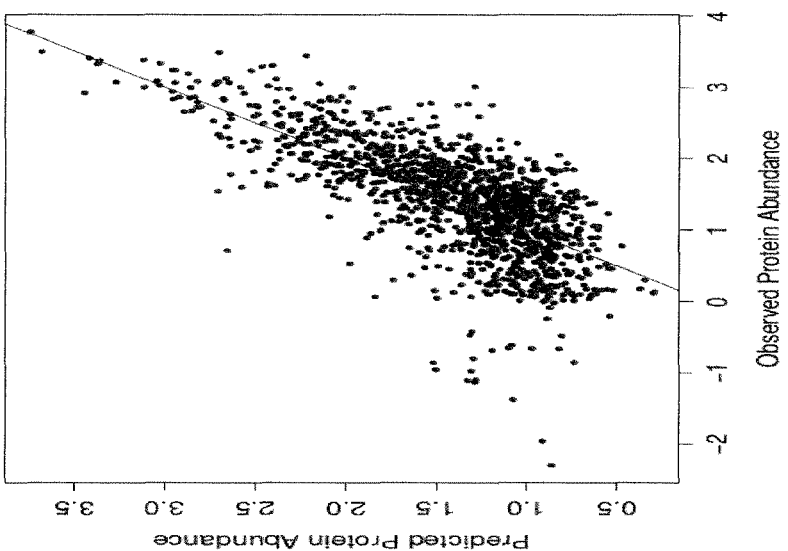
Figure 8:
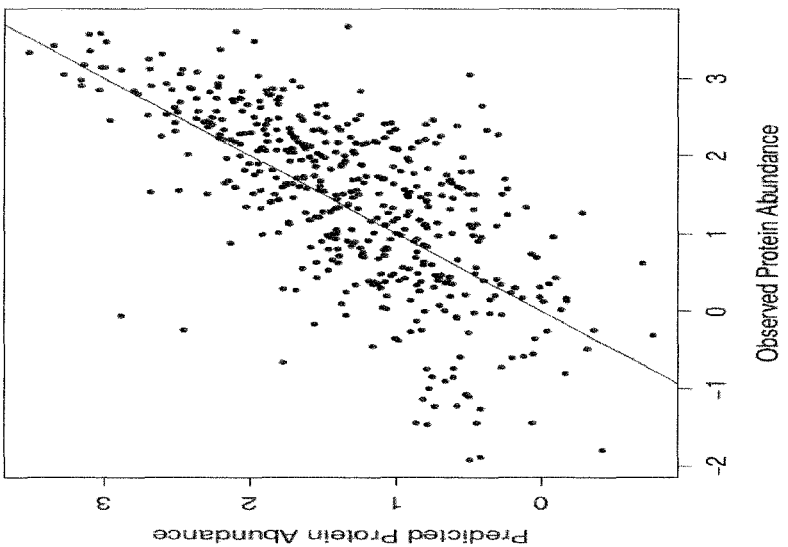

FIG. 8: Comparing measured protein abundance with predicted protein expression from the scoring function for all *E. coli*, *S. cerevisiae* and HEK293 genes where proteome data were available. The coefficients of determination R2 for *E. coli*, *S. cerevisiae* and HEK293 are 0.45, 0.50 and 0.38, respectively. Protein abundances are log-transformed, for *E. coli* and *S. cerevisiae* there is a noticeable cutoff at 0 caused by a lower resolution limit of the measurement methods used.

Figure 9A:
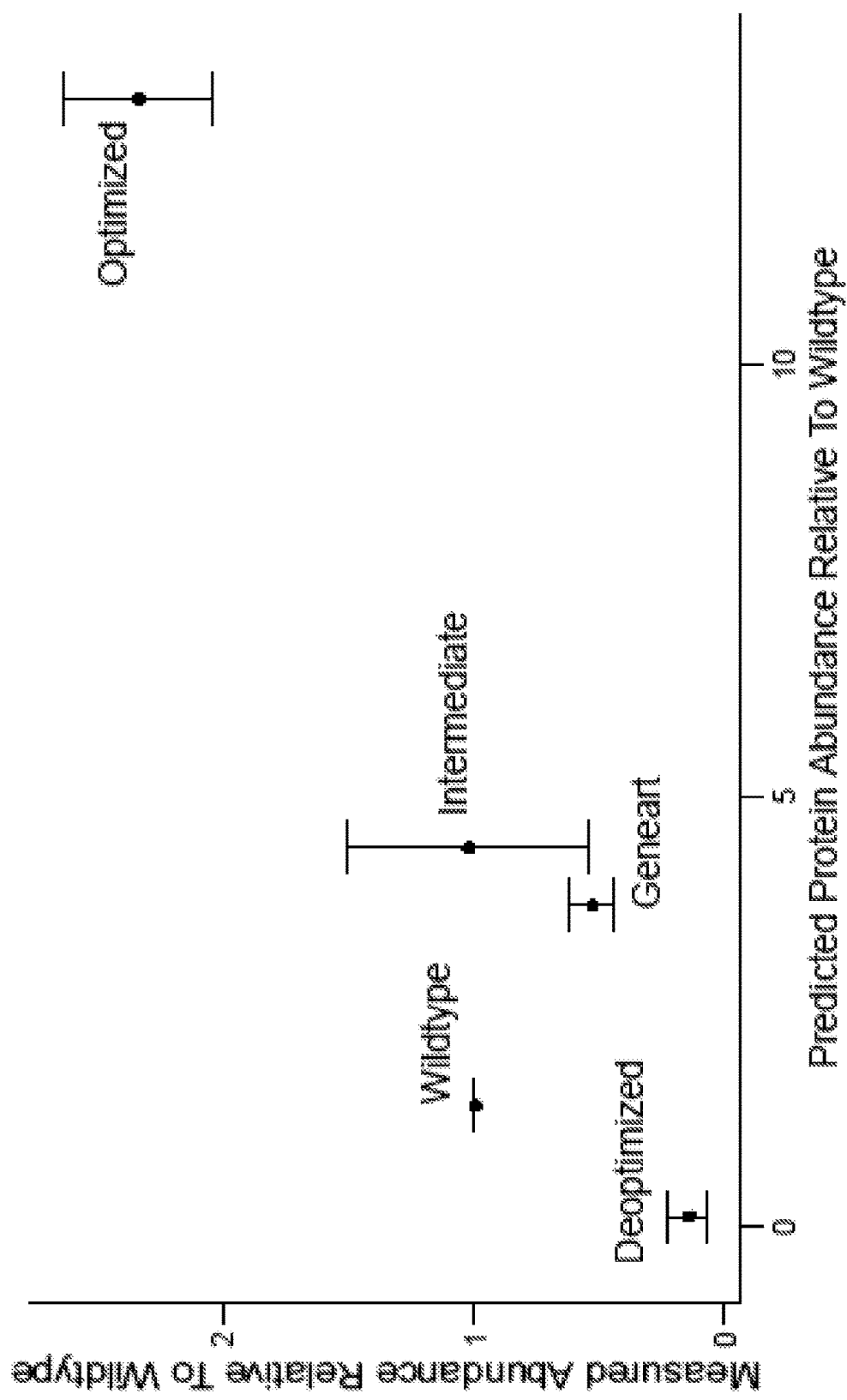

FIG. 9A/B: Protein expression of synthetic ova and manA in *Salmonella enterica* serovar Typhimurium. Measured protein abundance relative to wildtype compared to protein expression score relative to wild type for ova variants (A)

and manA variants (B). Ova protein levels were measured by Western blots (mean and standard deviation from 4 Western blots (biological replicates)), ManA protein levels are weighted averages of mass spectrometry measurements (5 biological replicates, 3 digestion replicates and 3 technical replicates each) and Western blots (3-5 replicates each) which correlate well.

Figure 9B:
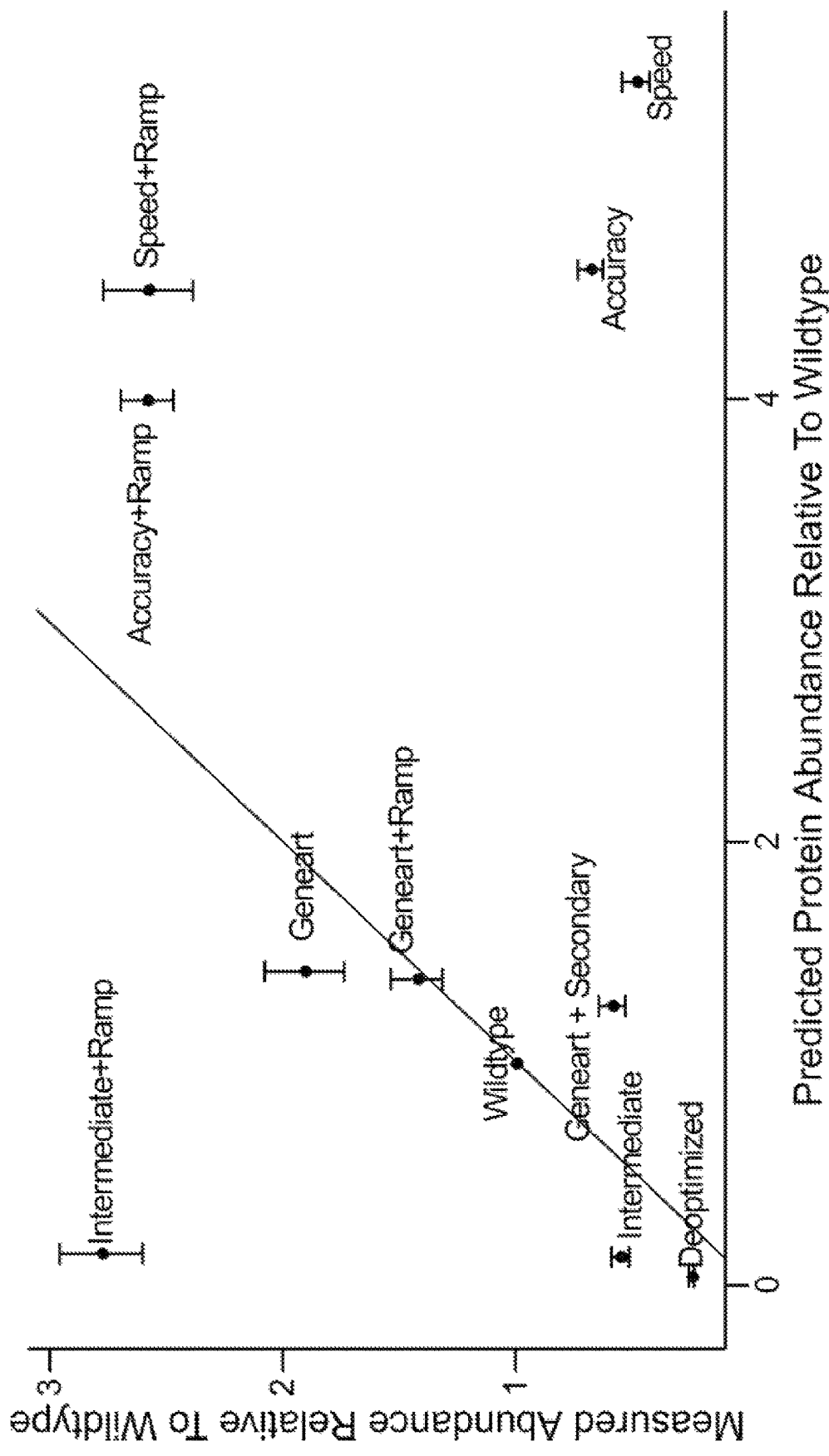
Figure 10:
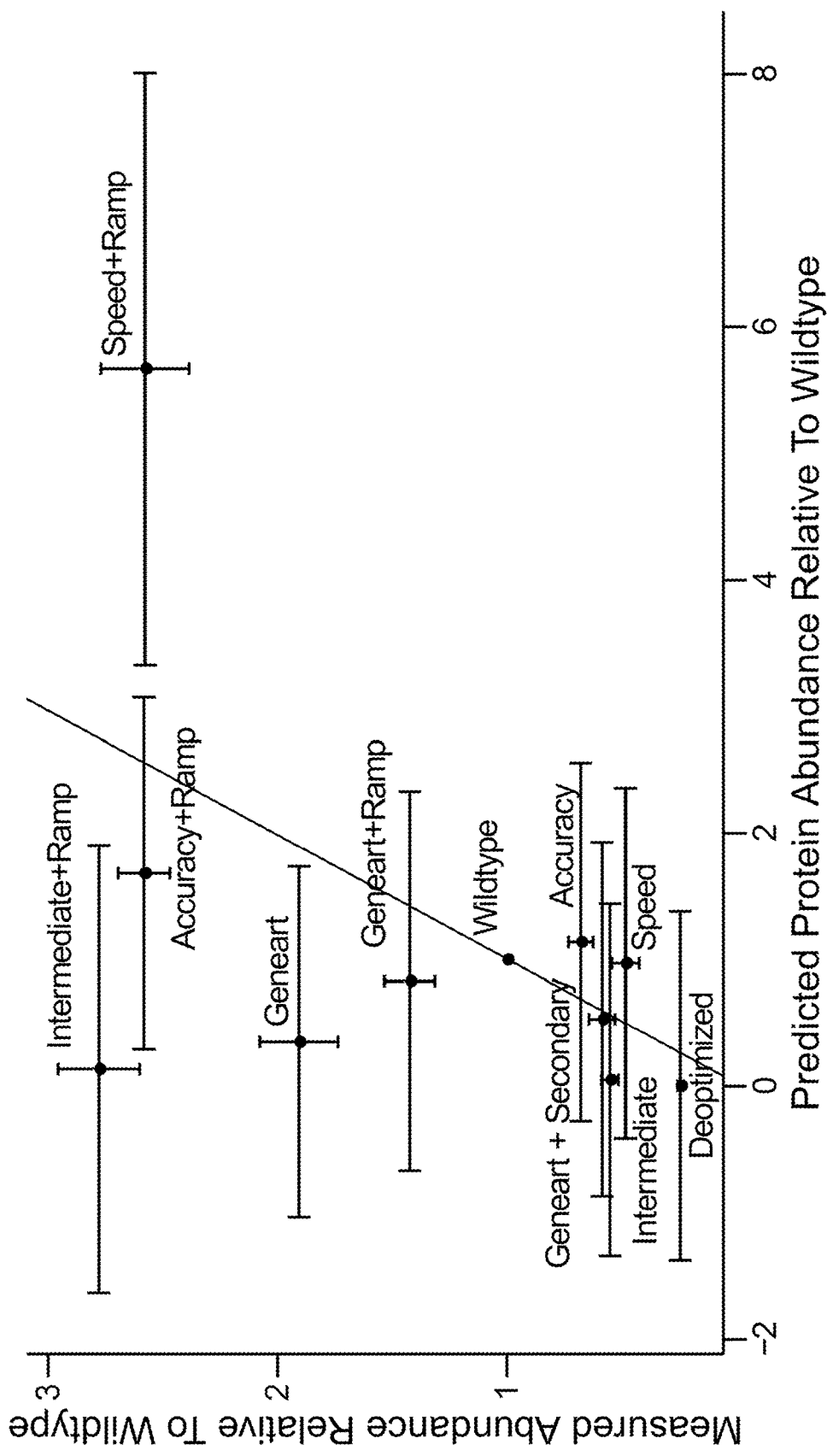

FIG. 10: Measured protein abundance relative to wild type compared to protein expression score relative to wild type manA variants. Protein levels are weighted averages of mass spectrometry measurements (5 biological replicates, 3 digestion replicates and 3 technical replicates each) and Western blots (3-5 replicates each) which correlate well. Different from FIG. 9B mRNA levels were determined for manA by quantitative real-time PCR (3 biological replicates and 3 technical replicates each) for consideration in the protein expression score. Transcript levels are not significantly different from each other within the large errors seen in the rtPCR measurements. Their consideration in the protein expression score therefore results in shifts and large error bars in the predicted protein levels without adding information.

Figure 11:
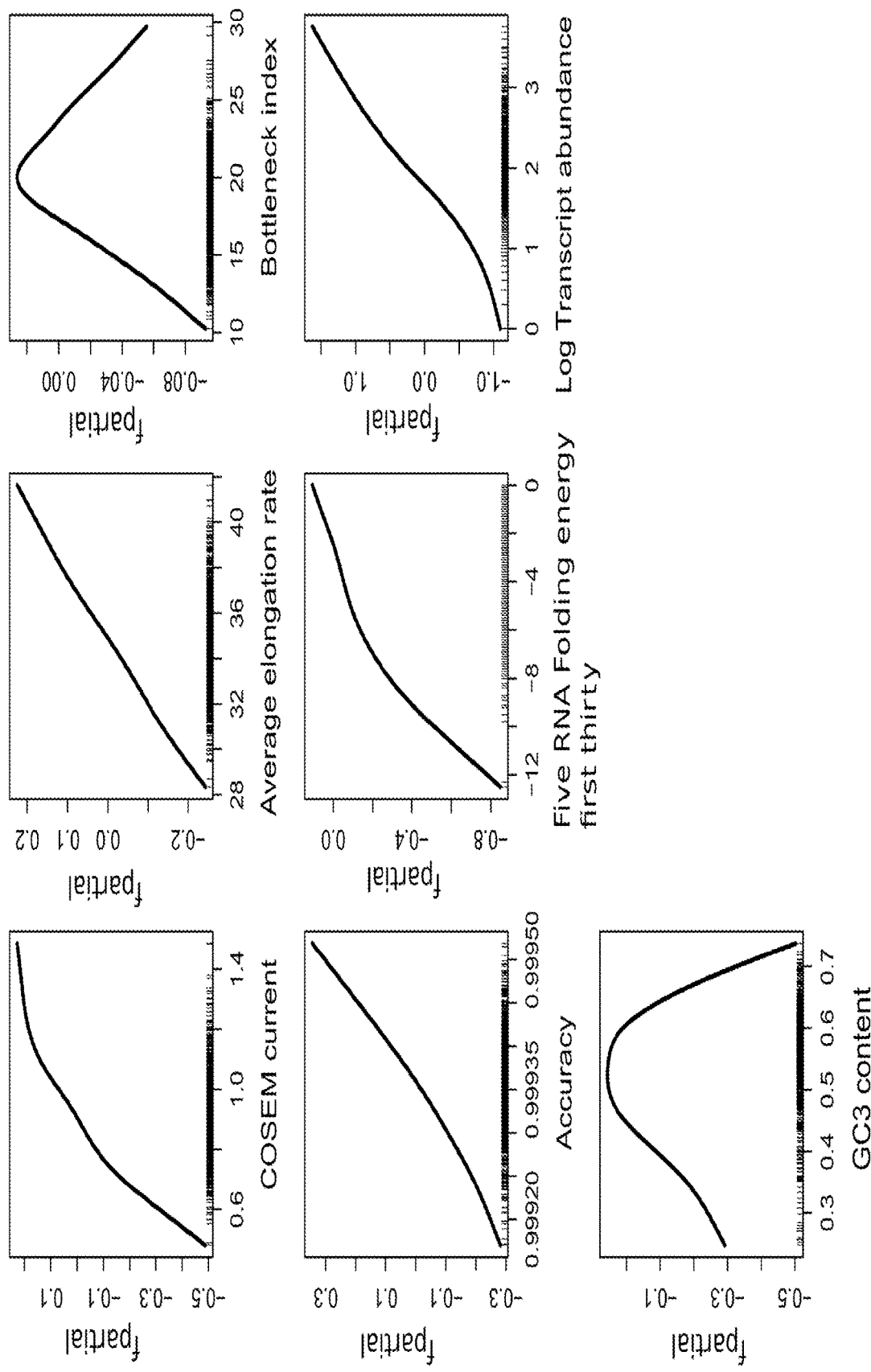

FIG. 11: Relative contributions and base functions of the scoring function of *E. coli*. To estimate protein abundance a generalized additive model with model-based boosting was trained on 80% of the data set. Shown are only covariates that significantly improved prediction.

Figure 12:
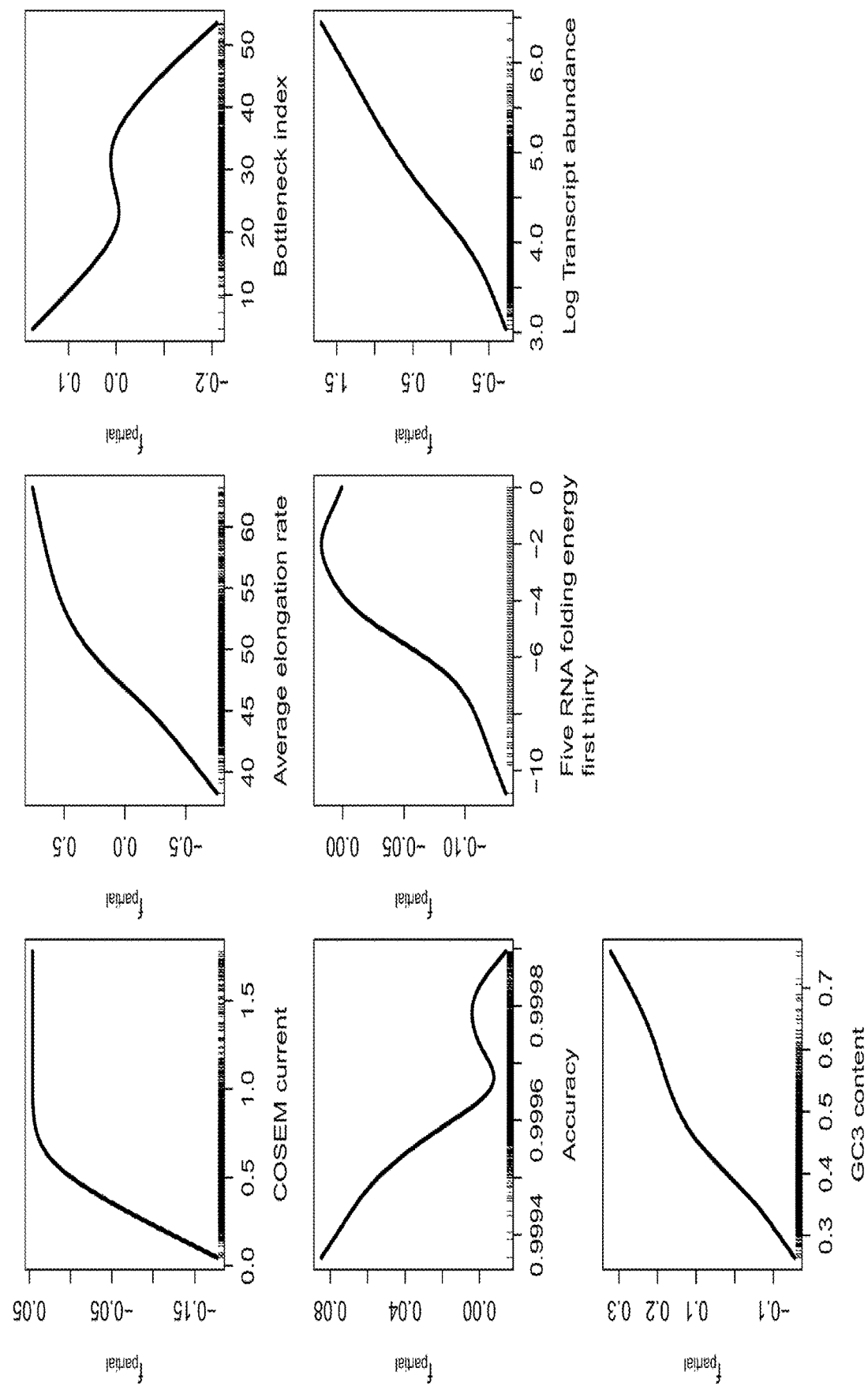

FIG. 12: Weight of Base functions for yeast.

Figure 13:
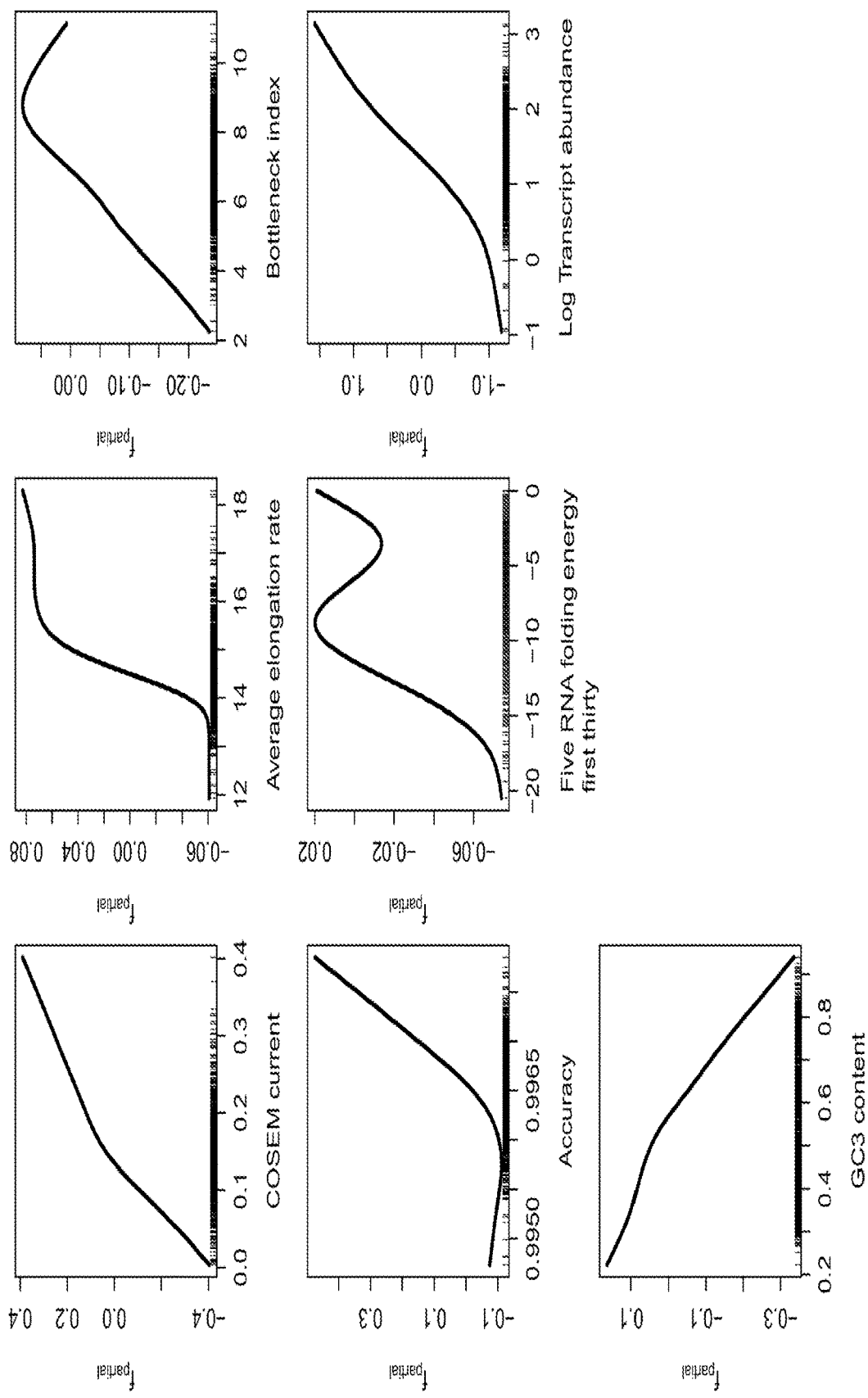

FIG. 13: Weight of Base functions for HEK293.

Figure 14:
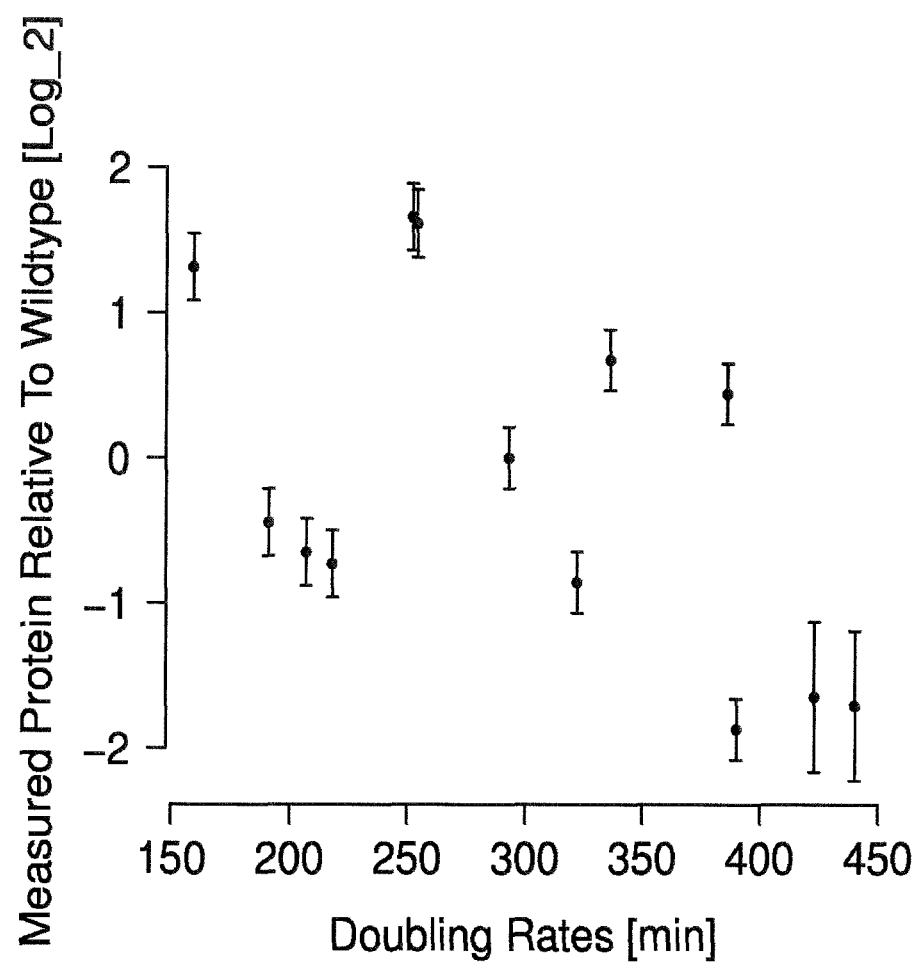

FIG. 14: Protein expression levels relative to wild type compared to doubling times of *S. enterica* serovar Typhimurium on minimal mannose medium. An increase in expression of manA reduces the doubling time and hence increases the growth rate.

Figure 15:
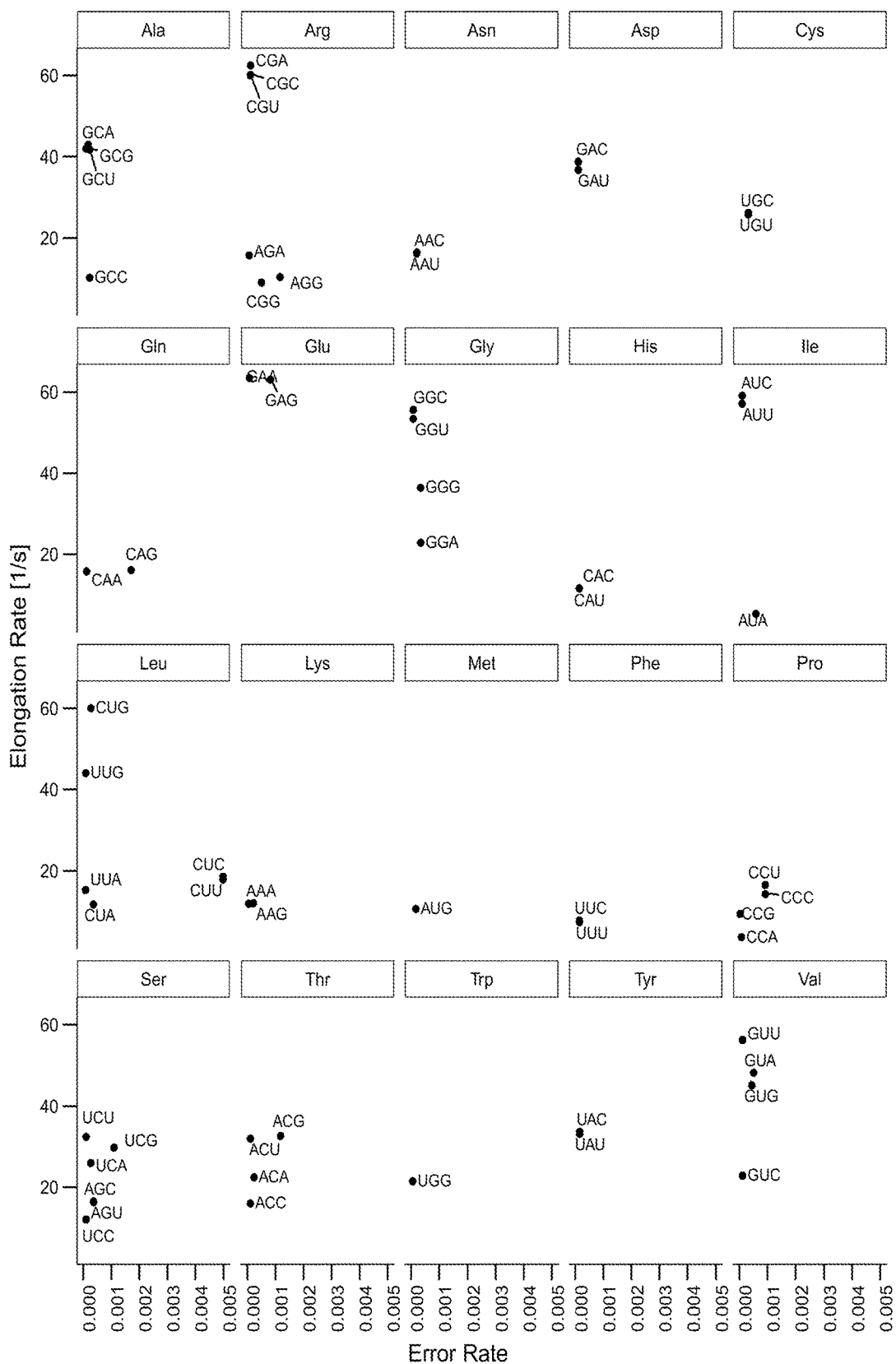

FIG. 15: Elongation rate and error frequencies for *E. coli*. In most cases an increase in elongation rate correlates with a decrease in error frequency.

Figure 16:
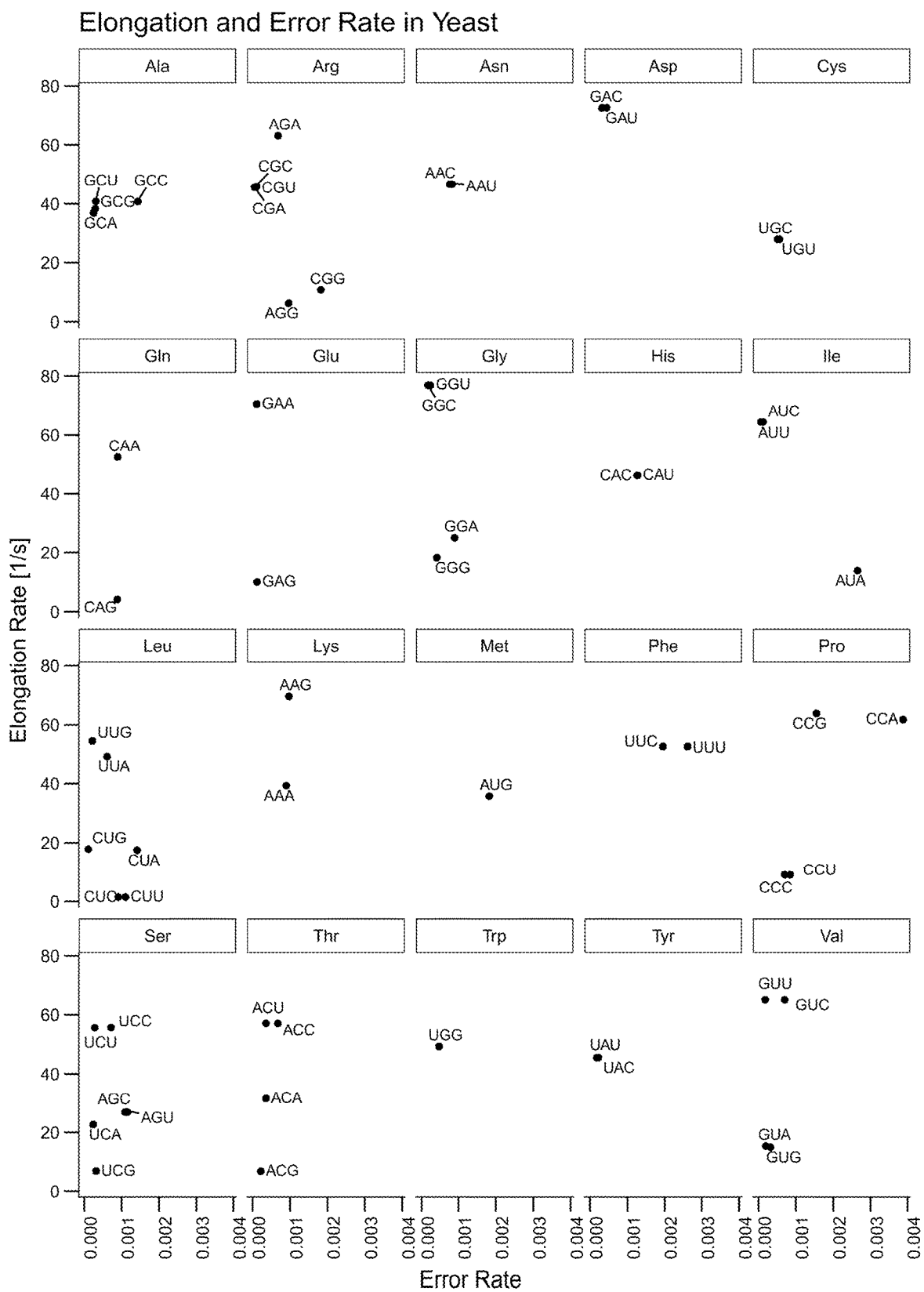

FIG. 16: Elongation rate and error frequencies for yeast. In most cases an increase in elongation rate correlates with a decrease in error frequency.

Figure 17:
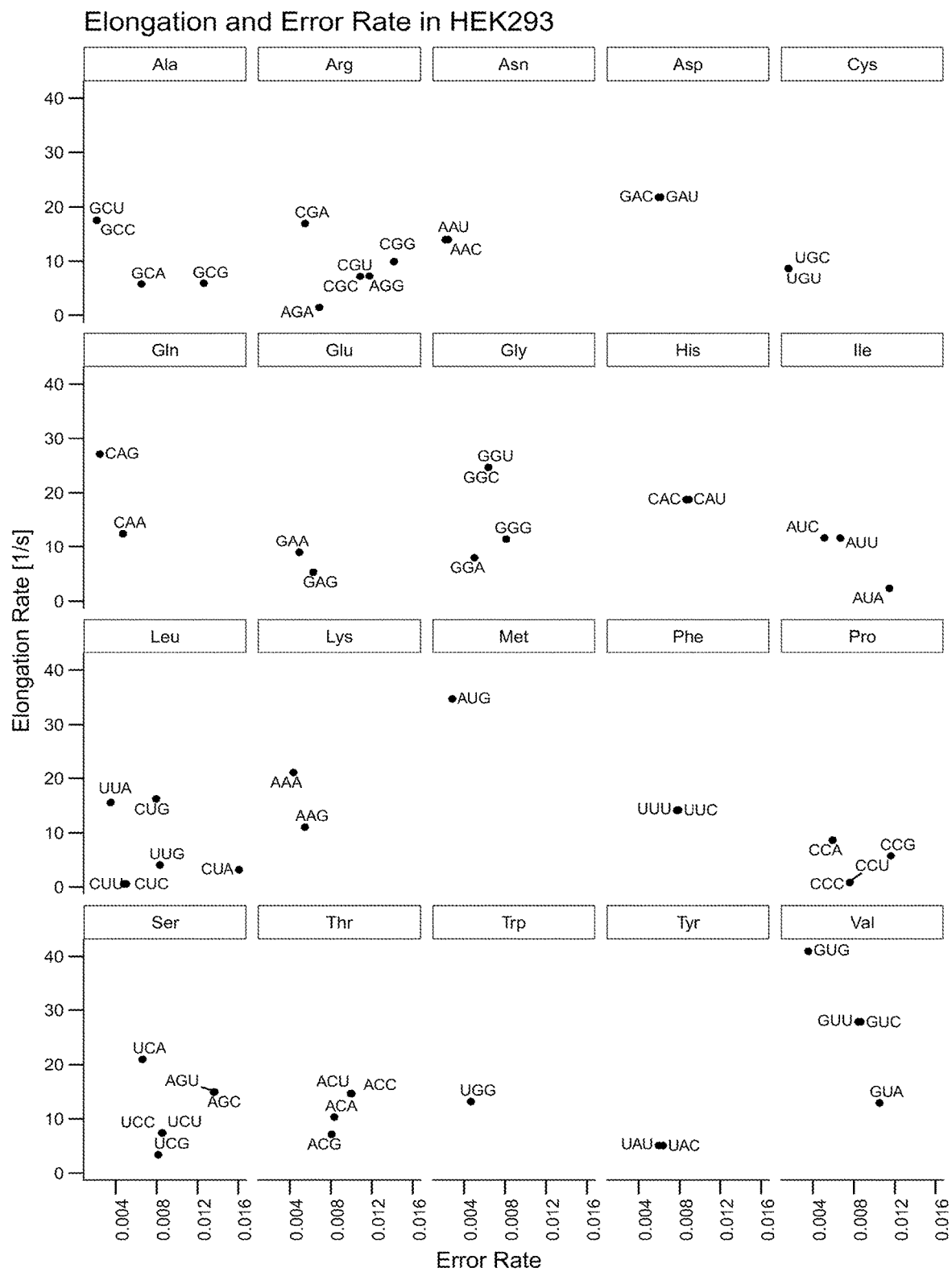

FIG. 17: Elongation rate and error frequencies for HEK293. In most cases an increase in elongation rate correlates with a decrease in error frequency.

DETAILED DESCRIPTION OF PREFERRED EMBODIMENTS

Figure 1:
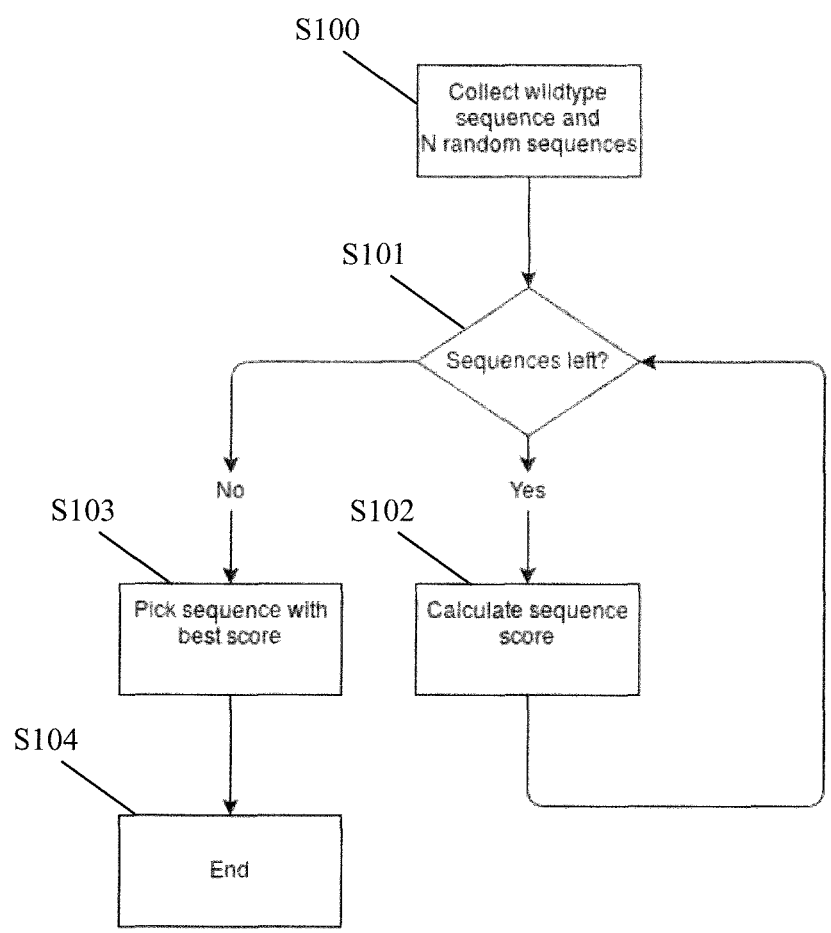
FIG. 1 is a flow chart of determining an optimized nucleotide sequence according to an embodiment of the present invention.

FIG. 1 is a flow chart of an exemplary embodiment of the present invention.

According to step S100, N random candidate nucleotide sequences are obtained for a given wildtype nucleotide sequence. How to obtain the N random candidate nucleotide sequences will be described in more detail with reference to the flow chart of FIG. 2 below.

In step S101 it is determined if there is a candidate nucleotide sequence left from the N random candidate nucleotide sequences for which no sequence score has been calculated. In the affirmative, step S102 is executed, i.e. the calculation of a sequence score for a particular candidate nucleotide sequence.

Steps S101 and S102 are repeated until a sequence score has been calculated for all of the N random candidate nucleotide sequences, i.e. until it is determined in step S101 that no candidate sequences are left from the N random candidate nucleotide sequences for which no sequence score has been calculated.

In case it has been determined in step S101 that a sequence score for all of the N random candidate nucleotide sequences has been calculated, step S103 picks the candidate sequence with the best score, which ends the method in step S104.

Best score in this regard refers to the score closest to the desired one, i.e. being predictive for the nucleotide sequence having the desired expression properties. The candidate nucleotide sequence that is picked in step S103 may be attributed to the highest predicted protein expression in the host cell, i.e. the picked candidate sequence is determined to be the optimized nucleotide sequence for increasing protein expression. Likewise, in step S103 the candidate nucleotide sequence with the lowest score may be determined. In case the expression shall be as low as possible, the candidate nucleotide sequence with the lowest score is picked in step S103. If the score reflects accuracy as the desired expression property the score may be attributed to the highest accuracy in translation in the host cell.

Figure 2:
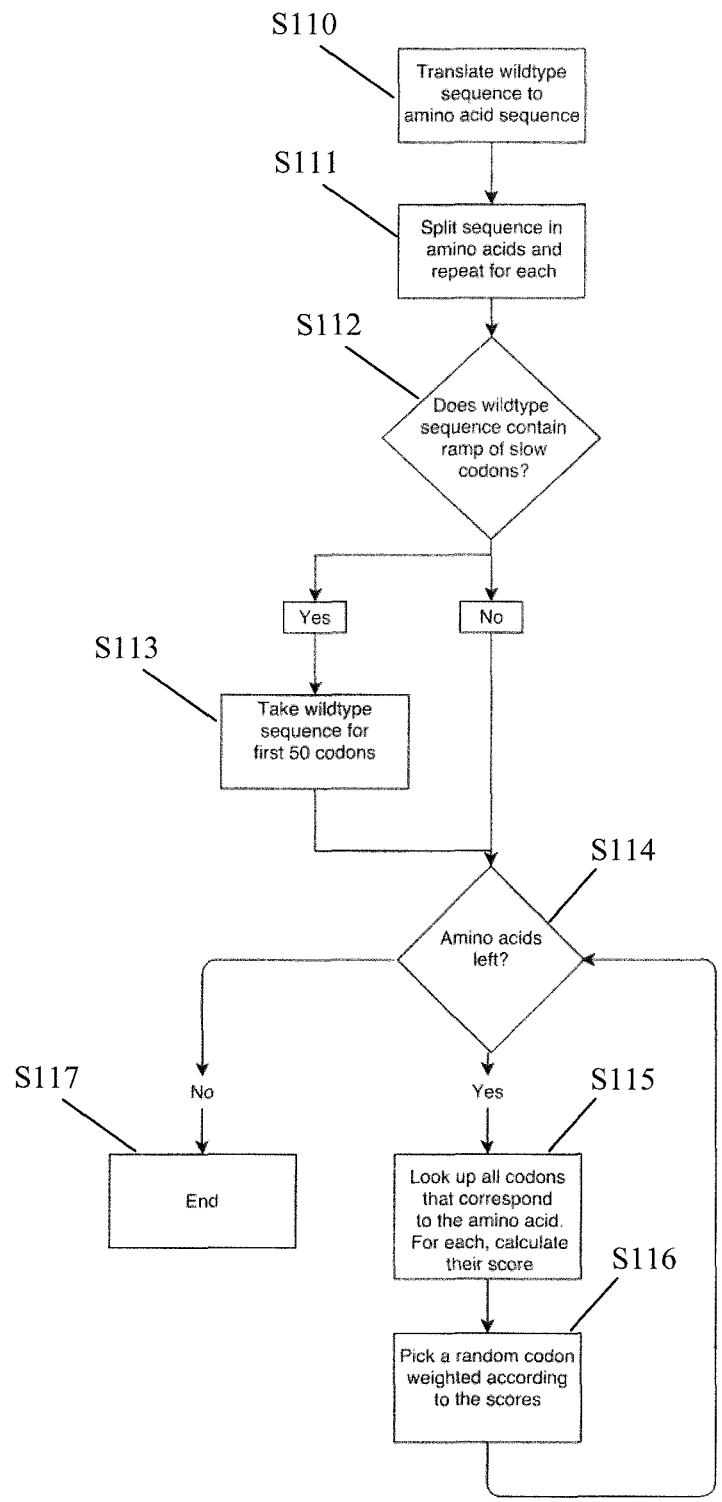
FIG. 2 is a flow chart illustrating the determination of a predetermined number of candidate sequences according to an embodiment of the present invention.

Obtaining the N random candidate nucleotide sequences is now further described with reference to the flow chart according to FIG. 2.

In a first step S110, the wildtype nucleotide sequence is translated into the encoded amino acid sequence and in a subsequent step S111 the nucleotide sequence is split into codons which are allocated to the respective amino acids of the encoded amino acid sequence.

Next, in step S112 it is determined if the wildtype nucleotide sequence contains a ramp of slow codons. That is, the average codon adaption index (CAI) of a predetermined number, e.g. 50, of the first codons and a CAI of the subsequent codons of the wildtype nucleotide sequence are compared to each other.

If the wildtype nucleotide sequence contains a ramp of slow codons is usually determined if the average CAI of the predetermined number of the first codons is different by a pre determined amount within the range of 10% to 50%, preferably 20% to 40% and more preferably 30% compared to the average CAI of the subsequent codons of the wildtype nucleotide sequence.

If it is determined that the wildtype nucleotide sequence contains a ramp of slow codons, step S113 determines that the predetermined number of first codons are to be taken from the wildtype nucleotide sequence as they are and the optimization method is performed for the codons starting from the first codon following the predetermined number, e.g. from the $51^{st}$ codon on.

Next, in step S114 it is determined if there is an amino acid left which has not been processed under the subsequent steps S115 and S116.

In case step S114 determines that there is an amino acid left which has not been processed under steps S115 and S116, step S115 is executed next. Step S115 obtains a local score for each codon encoding the current amino acid and calculates a local score based on organism and codon specific elongation rates and accuracies in the form of a local scoring function. Where the local scoring function is a weighted sum of the elongation rate of the proposed codon relative to that of the codon used in the starting sequence and the accuracy of the proposed codon relative to that of the codon used in the starting sequence.

In step S116 a random codon encoding the amino acid for the current position is picked, wherein the codon is weighted according to the obtained local score of step S115.

By repeating steps S115 and S116 for all remaining amino acids, a candidate nucleotide sequence is generated and step S117 ends the procedure.

Steps S110-S117 are then repeated for N times in order to generate N random candidate nucleotide sequences, wherein N may be a predetermined number set by the user or N may be determined by a criteria set by a user.

For example, a predetermined equilibrium value may be defined to determine N, wherein the coefficient of variation of the (maximum) sequence score of the last 100 sequences falls below a certain percentage, e.g. 10%, preferably 5%, and more preferably 1%.

Figure 3:
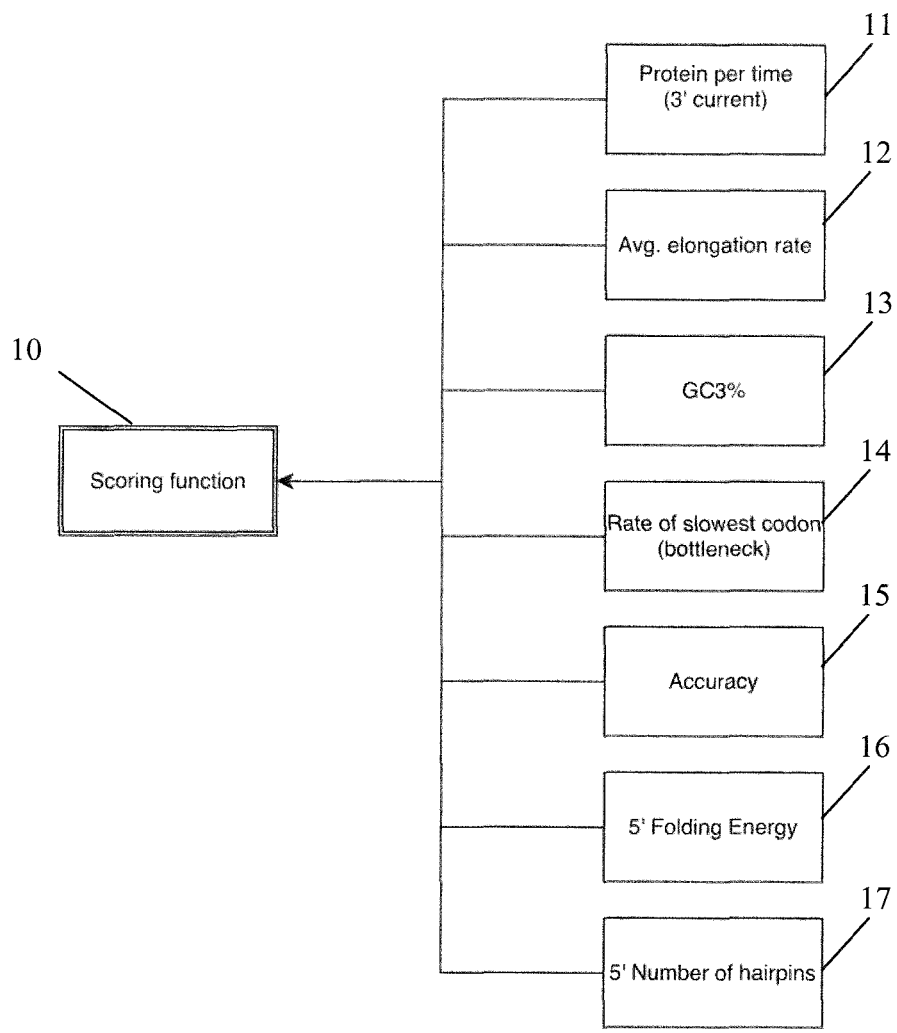
FIG. 3 illustrates the different sequence features as input into the scoring function according to an embodiment of the present invention. Note that mRNA levels might be considered as an additional feature if available.

FIG. 3 illustrates the different sequence features 11-17 which are input to the scoring function 10 according to an exemplary embodiment of the present invention. The protein expression score (sequence score) can be further improved through the consideration of mRNA transcript levels as a sequence feature where available.

In particular, the inputs to the scoring function 10 are protein per time (3' current or COSEM current) 11, average elongation rate 12, GC3 content 13, rate of slowest codon (bottleneck index) 14, accuracy 15, 5' folding energy 16 and 5' number of hairpins 17. However, further sequence features are possible and may be incorporated into the scoring function (see also scoring function below).

The sequence features of protein per time 11, average elongation rate 12 and accuracy 15 are based on a mechanistic model of protein translation.

The exact combination of sequence features may depend on the target organism and is determined by a statistical machine learning algorithm, preferably a boosted generalized additive model, which is further described with reference to FIG. 4.

Figure 4:
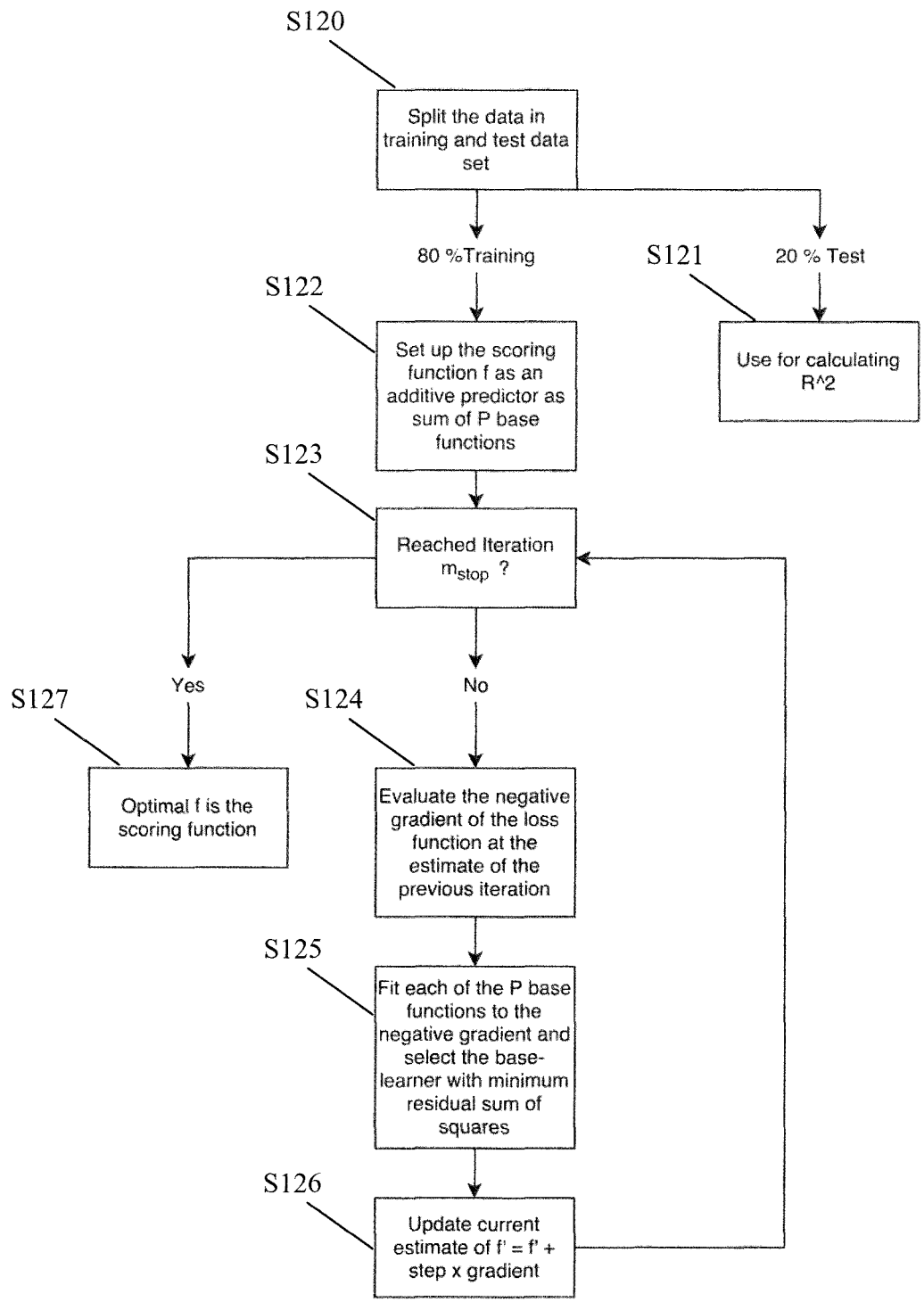
FIG. 4 is a flow chart illustrating a boosted generalized additive model according to an embodiment of the present invention.

The boosted generalized additive model according to FIG. 4 is based on the work of Torsten Hothorn, Peter Buehlmann, Thomas Kneib, Matthias Schmid, and Benjamin Hofner. mboost: Model-based boosting. R package version, pages 2-1, 2012.

In general, the scoring function $f$ is made up of base functions of the covariates:

$$\hat{f}(\vec{x}_j) = \sum_k \hat{f}_k(x_{kj})$$

wherein the index k represents the following features in sequence j to be described by base functions $\hat{f}_k$ which are estimated as described in the following with reference to FIG. 4. The functions in the above formula relate to the following sequence features:

Cosem Current (protein per time)
sequence accuracy
5' folding energy
influence of predefined motifs
GC3% or GC3 content
5' number of hairpins
bottleneck index
mRNA transcript abundance
number of AGG in first 30 codons
number of out-of-frame stop-codons
average elongation rate Note that the influence of predefined motifs, the number of hairpins, mRNA transcript levels and a ramp of slow codons are not generally included in the scoring function, but may be included in order to improve the scoring function for certain target organism.

In addition, the above list of sequence features is not exclusive and may be extended by incorporating further sequence features influencing the protein expression.

In step S120 a proteomics data set is divided into a training data set and test data set with a split of preferably 80% and 20% or 70% and 30%.

The test data set is used to calculate the $R^2$ value as illustrated by step S121.

The training data set is further processed in step S122, wherein the scoring function $f$ is set up as an additive predictor as the sum of the P base functions.

In step S123 it is determined if the iteration $m_{stop}$ is reached, wherein the parameter $m_{stop}$ is determined using cross validation of the loss function, i.e. the deviation of $f$ from the measured protein amount.

Next, in step S124 the negative gradient of the loss function at the estimate of the previous iteration is evaluated.

Step S125 fits each of the P base functions to the negative gradient and selects the base learner with minimum residual sum of squares.

Step S126 then updates the current estimate of $f'=f'+$step x gradient, wherein the step size is preferably set based on an experience-based value of 0.01.

Once the iteration $m_{stop}$ in step S123 is reached, the scoring function is determined as the optimal $f$ in step S127.

Figure 5:
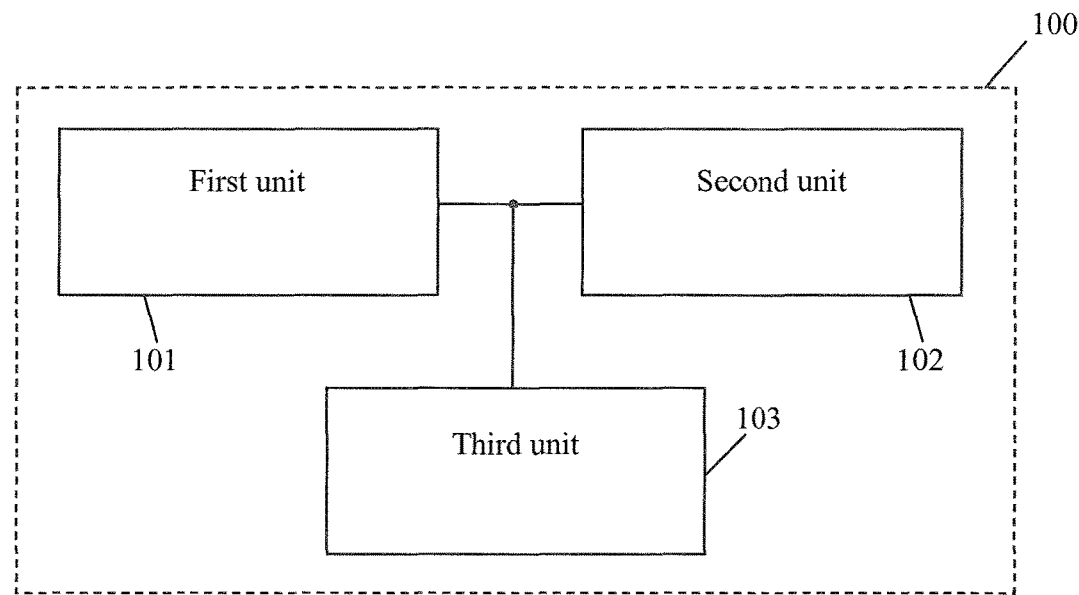
FIG. 5 illustrates a system according to an embodiment of the present invention.

FIG. 5 illustrates a system 100 according to another exemplary embodiment of the present invention. The system 100 comprises a first unit 101, a second unit 102 and a third unit 103.

The first unit 101 is connected to the second unit 102 and configured to generate a plurality of candidate nucleotide sequences as outlined above with reference to FIGS. 1-4. The first unit 101 is further configured to send the generated plurality of candidate nucleotide sequences to the second unit 102.

The second unit 102 is connected to the first unit 101 and the third unit 103. The second unit 102 receives the plurality of candidate nucleotide sequences from the first unit 101 and is configured to obtain or generate a sequence score based on a scoring function as outlined above with reference to FIGS. 1-4. That is, the second unit 102 is configured to obtain a sequence score based on a scoring function based on the plurality of sequence features generated by the first unit 101 that influence protein expression in the host cell using a statistical machine learning algorithm. The plurality of sequence features comprises one or more sequence features selected from the group consisting of protein per time, average elongation rate, and accuracy for each of the plurality of candidate nucleotide sequences. Subsequently, the second unit 102 sends the obtained sequence score to the third unit 103.

The third unit 103 is connected to the second unit 102 and receives the obtained sequence score from the second unit 102. The third unit 103 is further configured to determine the candidate nucleotide sequence with optimized protein expression in the host cell as the optimized nucleotide sequence according to the above description with reference to FIGS. 1-4. That is, the third unit 103 is configured to determine the candidate nucleotide sequence with optimized protein expression in the host cell as the optimized nucleotide sequence. The candidate nucleotide sequences with the highest sequence score is attributed to the highest predicted protein expression in the host cell, and the nucleotide sequence with the lowest sequence score is attributed to the lowest predicted protein expression in the host cell. The scoring function can be adapted to other target functions, a high score may alternatively represent high or low translation accuracy.

The first to third units may be implemented on a single computer system either as hardware or software modules.

Alternatively, the first to third units may be separate components configured for their intended purpose and connected to each other by conventional methods, i.e. wired or wireless.

As the present invention may be embodied in several forms without departing from the scope or essential characteristics thereof, it should be understood that the above-described embodiments are not limited by any of the details of the foregoing descriptions, unless otherwise specified, but rather should be construed broadly within the scope as defined in the appended claims, and therefore all changes and modifications that fall within the present invention are therefore intended to be embraced by the appended claims.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. The words carrier, holder, satellite, plate, platter, susceptor etc. represent the same meaning in this text and are in use interchangeably. The same is valid for the group of words like channel, hollow tube, hole, path etc. The variety of definitions has a regional and/or a professional origin.

The present invention is further described with reference to the following examples.

I. Materials and Methods

Figure 6:
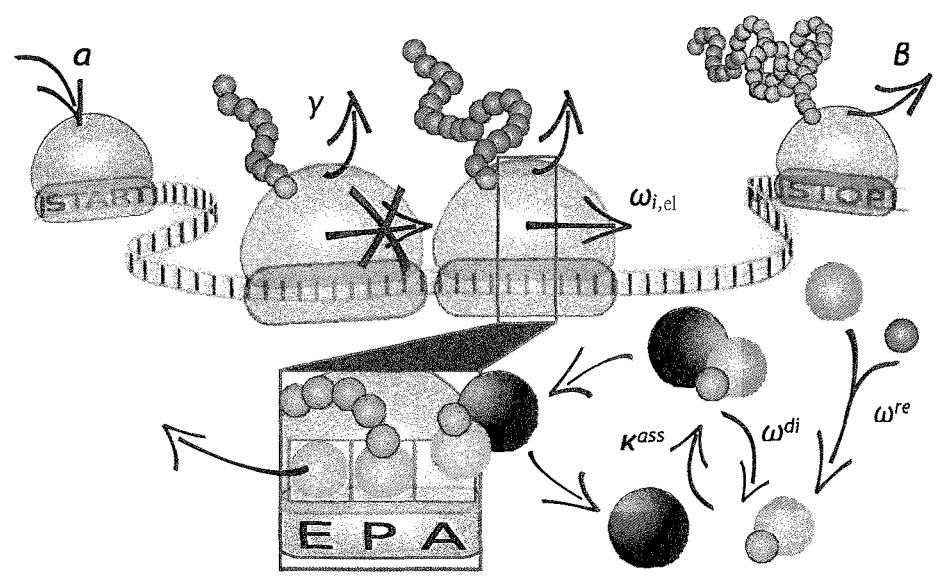
FIG. 6: Sketch of the codon-specific elongation model (COSEM): Ribosomes attach to an mRNA with initiation rate $\alpha$ determined by the ribosome concentration if the initiation site is not occupied and move to the next position with an elongation rate $\omega_{i,elo}$ (or $\omega_i$ for short) and accuracy $\alpha_i$ specific to codon at position i in the sequence as well as the organism under consideration. Elongation rates and accuracies are derived from the interaction between aa-tRNA (grey spheres, aminoacylated if associated with a green sphere), elongation factors (blue spheres) and GTP molecules (not shown) taking their organism specific concentrations into account (for details see (36, 37)). Protein translation may be terminated prematurely by ribosome drop-off at a rate $\Upsilon$. Furthermore, ribosomes cannot overtake one another and can, at most, approach one another within one ribosomal footprint. Finally, the ribosome detaches from the last codon at a rate $\beta$ and a complete protein has been produced.

1. The Codon-Specific Elongation Model (COSEM) and Simulation of Protein Translation Protein translation within the codon-specific elongation model (COSEM) strongly leans on the dynamics of the totally asymmetric exclusion process (TASEP) as sketched in FIG. 6. The ribosome attaches to the mRNA with an initiation rate, α, depending on the concentration of ribosomes available for translation initiation. It covers d codons corresponding to the ribosomal footprint and advances with a position dependent elongation rate $\omega_{i,elo}$ (or $\omega_i$ for short) and accuracy $\alpha_i$ depending on the translated codon. If a ribosome is selected for movement but is blocked by a preceding ribosome, it is flagged for moving as soon as the blocking ribosome advances. Protein elongation is in competition with ribosome drop-off that is modelled through a drop-off rate per time γ. For the simulations of the codon-specific elongation model kinetic Monte Carlo was used (22, 54): a list of all events that can occur is created (ribosome initiation, elongation and drop-off) each with their respective rates. The sum of all these rates gives the rate with which any of the events occurs. A random event is chosen weighted by the individual rates. This event is then executed, if possible, and the simulation time is advanced by the logarithm of the total rate of all events. Generally, it is also possible to use a simpler version in which time is advanced with a small increment δt at every iteration step. Then, for every event with rate r the probability of occurring in the time frame St is approximately δt r. This simpler implementation is nearly as fast as kinetic Monte Carlo. For extended error checking the simulations where performed both ways and the source code is available upon request.

Although maximizing the $\omega_i$ maximizes the amount of protein produced per mRNA and time, i.e. the COSEM current, there is no simple dependence between the set of elongation rates $\{\omega_i\}$ and the actual amount of protein translated per time and mRNA:
in the presence of bottlenecks of slow codons an increase in average elongation rate (either determined through the arithmetic or harmonic mean over a gene sequence of n codons) might not directly relate to an increase in protein production. Thus, the average elongation rate $<\omega>$ is complemented by the simulated protein production rate or COSEM current p. Optimizing p instead of $<\omega>$ can be particularly relevant when considering the trade-off between fast and accurate codons.

2. Codon-Specific Elongation Rates and Accuracies

Codon-specific elongation rates and accuracies for translation in *E. coli* were calculated by minimizing the kinetic distance between a set of measured in-vitro rates and predicted rates compatible with translation in-vivo as described in (36, 37). To obtain codon-specific elongation rates and accuracies for HepG2, HEK293 and *S. cerevisiae* cells, we applied the same method using parameters listed in Table S1. Briefly, translation of a codon is described by a twelve-state Markov process with twelve independent transition rates. Experimentally determined in-vitro values of these transition rates (18) are used to predict a set of in-vivo transition rates compatible with the organism- and growth-rate dependent overall rate of protein synthesis. Furthermore, the codon-specific elongation rates and accuracies were assumed to depend on the concentrations of free ternary complexes via competition of cognate, near-cognate and non-cognate ternary complexes at the ribosomes' binding sites. Thus, from codon usages and measured or estimated tRNA abundances the concentrations of the corresponding ternary complexes are calculated by taking into account the recharging of tRNAs by aminoacyl tRNA synthetases. A detailed listing of all model parameters and codon-specific elongation rates and accuracies can be found in Tables S1 to S12.

For *E. coli* a preferred average initiation is reported 5 min-1 for the lac-operon and 4 min$^{-1}$ as median for all *E. coli* genes. A preferred initiation rate for *E. coli* is 100 s$^{-1}$ or larger than 10 s$^{-1}$. For *S. cerevisiae* a preferred median is 2.5 s$^{-1}$ or the range of 1-5 s$^{-1}$. Preferred for human stem cells, e.g. HeLa, but also HEK293, the median is 0.06 s$^{-1}$ and preferably larger than 0.01 s$^{-1}$. Preferred drop-off rates for *E. coli*, *S. cerevisiae* and human cell lines have been chosen to 6.6 10-3 s$^{-1}$, 9.9 10-3 s$^{-1}$ and 1.8 10-3 s$^{-1}$, respectively (Sin, Celine, Davide Chiarugi, and Angelo Valleriani. "Quantitative assessment of ribosome drop-off in *E. coli*" Nucleic acids research 44.6 (2016): 2528-2537. "Dissecting eukaryotic translation and its control by ribosome density mapping". In: Nucleic acids research 33.8 (2005), pp. 2421-2432).

TABLE S1

Parameters used to calculate codon-specific elongation rates and error frequencies for *S. cerevisiae* and HEK293 cells.

| Parameter | Organism | Value | Reference |
|---|---|---|---|
| Ribosomal transition rates | both | Table S2 | this document |
| Definition of "cognate" | *S. Cerevisae* | Table S3 | [66] |
|  | HEK293 | Table S4 | [67] |
| Definition of "near-cognate" | both |  | according to [68, 69] |
| Codon usages | *S. Cerevisae* | Table S5 | from mRNA abundances [70] |
|  | HEK293 | Table S6 | from mRNA abundances [71] |
| tRNAs per cell | *S. Cerevisae* | Table S3 | [66] |
|  | HEK293 | Table S4 | [72] |
| Ribosomes per cell | *S. Cerevisae* | 2.00E+05 | [70] |
|  | HEK293 | 1.00E+07 | [63] |

TABLE S1-continued

Parameters used to calculate codon-specific elongation rates and error frequencies for *S. cerevisiae* and HEK293 cells.

| Parameter | Organism | Value | Reference |
|---|---|---|---|
| eEF1a1 per cell | *S. Cerevisiae* | 2.00E+06 | [74] |
|  | HEK293 | 1.00E+08 | [73] |
| Cell volume | *S. Cerevisiae* | 37 μm³ | [75] |
|  | HEK293 | 1150 μm³ | [76] |
| Overall elongation rate | *S. Cerevisae* | 33 s⁻¹ | [70] |
|  | HEK293 | 6 s⁻¹ | [77] |

TABLE S2

In-vivo rates of ribosomal transitions for *S. cerevisiae* and HEK293 cells. The in-vivo rates of ribosomal transitions (with relative standard deviations RSD) were obtained under the assumption of a 2-1-2 pathway of tRNA release from the ribosomal E site by minimizing the kinetic distance to rates measured in vitro for *E. coli*, see [68, 69] for a detailed description and the corresponding parametes in *E. coli*.

| Rate | *S. Cerevisae* | HEK293 | RSD | Unit |
|---|---|---|---|---|
| $\kappa^*_{on}$ | 94.00 | 94.00 | 0.10 | $\mu M^{-1}s^{-1}$ |
| $\omega^*_{off}$ | 6400.00 | 1800.00 | 0.40 | $s^{-1}$ |
| $\omega^*_{rec}$ | 14900.00 | 2900.00 | 0.30 | $s^{-1}$ |
| $\omega^*_{21}$ | 2.00 | 2.00 | 0.30 | $s^{-1}$ |
| $\omega^*_{23}$ | 2300.00 | 1500.00 | 0.30 | $s^{-1}$ |
| $\omega^*_{con}$ | 820.00 | 470.00 |  | $s^{-1}$ |
| $\omega^*_{45}$ | 750.00 | 230.00 | 0.20 | $s^{-1}$ |
| $\omega^*_{40}$ | 1.00 | 1.00 |  | $s^{-1}$ |
| $\omega^*_{76}$ | 16700.00 | 3200.00 | 0.30 | $s^{-1}$ |
| $\omega^*_{78}$ | 3.00 | 5.00 | 0.30 | $s^{-1}$ |
| $\omega^*_{910}$ | 0.28 | 0.29 | 0.20 | $s^{-1}$ |
| $\omega^*_{90}$ | 8.00 | 6.00 | 0.20 | $s^{-1}$ |
| $\omega^*_{pro}$ | 450.00 | 170.00 | 0.50 | $s^{-1}$ |

TABLE S3

Concentrations of tRNAs in *S. cerevisiae*.

| Anti-Codon | Amino acid | Molecules/cell |
|---|---|---|
| UGC | Ala | 51437 |
| IGC | Ala | 113163 |
| UCU | Arg | 113163 |
| CCU | Arg | 10289 |
| CCG | Arg | 10289 |
| ICG | Arg | 61726 |
| GUU | Asn | 102875 |
| GUC | Asp | 154315 |
| GCA | Cys | 41152 |
| UUG | Gln | 92589 |
| CUG | Gln | 10289 |
| UUC | Glu | 144026 |
| CUC | Glu | 20574 |
| UCC | Gly | 30863 |
| CCC | Gly | 20574 |
| GCC | Gly | 164601 |
| GUG | His | 72012 |
| UAU | Ile | 20574 |
| IAU | Ile | 133738 |
| UAG | Leu | 30863 |
| GAG | Leu | 10289 |
| UAA | Leu | 72012 |
| CAA | Leu | 102875 |
| UUU | Lys | 72012 |
| CUU | Lys | 144026 |
| CAU | Met | 51437 |
| GAA | Phe | 102875 |
| UGG | Pro | 102875 |
| IGG | Pro | 20574 |
| GCU | Ser | 41152 |
| UGA | Ser | 30863 |
| CGA | Ser | 10289 |
| IGA | Ser | 113163 |
| UGU | Thr | 41152 |
| CGU | Thr | 10289 |
| IGU | Thr | 113163 |
| CCA | Trp | 61726 |
| GUA | Tyr | 82300 |
| UAC | Val | 20574 |
| CAC | Val | 20574 |
| IAC | Val | 144026 |

TABLE S4

Concentrations of tRNAs in HEK293 cells.

| Anti-Codon | Amino acid | Molecules/cell |
|---|---|---|
| UGC | Ala | 916573 |
| AGC | Ala | 3384116 |
| CGC | Ala | 850415 |
| UCG | Arg | 2250540 |
| CCG | Arg | 1446617 |
| ACG | Arg | 1179105 |
| UCU | Arg | 329157 |
| CCU | Arg | 1053973 |
| AUU | Asn | 0 |
| GUU | Asn | 2452966 |
| GUC | Asp | 4288905 |
| GCA | Cys | 1292794 |
| UUG | Gln | 1782775 |
| CUG | Gln | 4822637 |
| UUC | Glu | 1552467 |
| CUC | Glu | 1328953 |
| UCC | Gly | 1195112 |
| CCC | Gly | 1813654 |
| GCC | Gly | 4646638 |
| GUG | His | 3156779 |
| UAU | Ile | 381136 |
| AAU | Ile | 2266860 |
| GAU | Ile | 3321 |
| UAG | Leu | 470419 |
| UAA | Leu | 2049035 |
| CAA | Leu | 726362 |
| CAG | Leu | 3139571 |
| AAG | Leu | 492534 |
| UUU | Lys | 3297624 |
| CUU | Lys | 2095918 |
| CAU | Met | 7409911 |
| GAA | Phe | 2426202 |
| UGG | Pro | 1273045 |
| AGG | Pro | 601330 |
| CGG | Pro | 778307 |
| UGA | Ser | 2949312 |
| CGA | Ser | 436044 |
| AGA | Ser | 1339964 |
| GCU | Ser | 2392655 |
| UGU | Thr | 1461888 |
| CGU | Thr | 961206 |
| AGU | Thr | 2399438 |
| CCA | Trp | 1695475 |
| GUA | Tyr | 984731 |
| AUA | Tyr | 261 |
| UAC | Val | 1960321 |
| CAC | Val | 10343136 |
| AAC | Val | 5919816 |

TABLE S5

Anti-codons of cognate tRNAs and codon usages (CU) for all codons in *S. cerevisiae*.

| Codon | Anti-codon | CU [%] |
|---|---|---|
| AAA | UUU | 2.91 |
| AAC | GUU | 3.01 |
| AAG | CUU | 5.76 |
| AAU | GUU | 1.77 |
| ACA | UGU | 0.9 |
| ACC | IGU | 1.99 |
| ACG | CGU | 0.39 |
| ACU | IGU | 2.5 |
| AGA | UCU | 3.79 |
| AGC | GCU | 0.59 |
| AGG | CCU | 0.46 |
| AGU | GCU | 0.73 |
| AUA | UAU | 0.75 |
| AUC | IAU | 2.41 |
| AUG | CAU | 1.47 |
| AUU | IAU | 2.7 |
| CAA | UUG | 3.2 |
| CAC | GUG | 1.13 |
| CAG | CUG | 0.64 |
| CAU | GUG | 0.86 |
| CCA | UGG | 2.64 |
| CCC | IGG | 0.35 |
| CCG | UGG | 0.23 |
| CCU | IGG | 0.87 |
| CGA | ICG | 0.1 |
| CGC | ICG | 0.13 |
| CGG | CCG | 0.08 |
| CGU | ICG | 0.93 |
| CUA | UAG | 0.91 |
| CUC | GAG | 0.27 |
| CUG | UAG | 0.54 |
| CUU | GAG | 0.62 |
| GAA | UUC | 5.2 |
| GAC | GUC | 2.35 |
| GAG | CUC | 1.13 |
| GAU | GUC | 2.73 |
| GCA | UGC | 0.95 |
| GCC | IGC | 2.07 |
| GCG | UGC | 0.33 |
| GCU | IGC | 4.65 |
| GGA | UCC | 0.58 |
| GGC | GCC | 0.76 |
| GGG | CCC | 0.37 |
| GGU | GCC | 4.81 |
| GUA | UAC | 0.61 |
| GUC | IAC | 2.36 |
| GUG | CAC | 0.68 |
| GUU | IAC | 3.43 |
| UAA |  | stop |
| UAC | GUA | 2.07 |
| UAG |  | stop |
| UAU | GUA | 1.07 |
| UCA | UGA | 0.94 |
| UCC | IGA | 1.91 |
| UCG | CGA | 0.4 |
| UCU | IGA | 2.87 |
| UGA |  | stop |
| UGC | GCA | 0.39 |
| UGG | CCA | 0.96 |
| UGU | GCA | 0.87 |
| UUA | UAA | 1.87 |
| UUC | GAA | 2.34 |
| UUG | CAA | 4.08 |
| UUU | GAA | 1.57 |

TABLE S6

Anti-codons of cognate tRNAs and codon usages (CU) for all codons in HEK293 cells.

| Codon | Anti-codon | CU [%] |
|---|---|---|
| AAA | UUU | 2.73 |
| AAC | GUU | 1.94 |
| AAG | CUU | 4.11 |
| AAU | GUU | 1.66 |
| ACA | UGU | 1.41 |
| ACC | AGU | 1.76 |
| ACG | CGU | 0.56 |
| ACU | AGU | 1.31 |
| AGA | UCU | 1.14 |
| AGC | GCU | 1.64 |
| AGG | CCU | 1.02 |
| AGU | GCU | 1.12 |
| AUA | UAU | 0.62 |
| AUC | AAU, GAU | 2.29 |
| AUG | CAU | 2.35 |
| AUU | AAU | 1.79 |
| CAA | UUG | 1.04 |
| CAC | GUG | 1.32 |
| CAG | CUG | 3.45 |
| CAU | GUG | 0.97 |
| CCA | UGG | 1.58 |
| CCC | AGG | 1.8 |
| CCG | CGG | 0.64 |
| CCU | AGG | 1.71 |
| CGA | UCG | 0.75 |
| CGC | ACG | 1.17 |
| CGG | CCG | 1.28 |
| CGU | ACG | 0.62 |
| CUA | UAG | 0.65 |
| CUC | AAG | 1.7 |
| CUG | CAG | 3.68 |
| CUU | AAG | 1.29 |
| GAA | UUC | 3.19 |
| GAC | GUC | 2.69 |
| GAG | CUC | 4.35 |
| GAU | GUC | 2.59 |
| GCA | UGC | 1.68 |
| GCC | AGC | 2.91 |
| GCG | CGC | 0.75 |
| GCU | AGC | 2.14 |
| GGA | UCC | 1.67 |
| GGC | GCC | 2.38 |
| GGG | CCC | 1.51 |
| GGU | GCC | 1.33 |
| GUA | UAC | 0.77 |
| GUC | AAC | 1.41 |
| GUG | CAC | 2.94 |
| GUU | AAC | 1.2 |
| UAA |  | stop |
| UAC | GUA | 1.49 |
| UAG |  | stop |
| UAU | GUA, AUA | 1.23 |
| UCA | UGA | 1.04 |
| UCC | AGA | 1.58 |
| UCG | CGA | 0.41 |
| UCU | AGA | 1.45 |
| UGA |  | stop |
| UGC | GCA | 0.9 |
| UGG | CCA | 1.02 |
| UGU | GCA | 0.78 |
| UUA | UAA | 0.67 |
| UUC | GAA | 1.86 |
| UUG | CAA | 1.26 |
| UUU | GAA | 1.68 |

TABLE S7

Codon-specific elongation rates for *E. coli* at a specific growth rate of 2.5 h$^{-1}$ as previously published in [65]. See supplemental data in [65] for codon-specific elongation rates at other specific growth rates.

| Codon | Codon-specific elongation rate [s$^{-1}$] |
|---|---|
| AAA | 12.28 |
| AAC | 16.65 |
| AAG | 12.17 |
| AAU | 16.43 |
| ACA | 22.66 |
| ACC | 16.23 |
| ACG | 32.91 |
| ACU | 32.21 |
| AGA | 15.95 |
| AGC | 16.75 |
| AGG | 10.64 |
| AGU | 16.55 |
| AUA | 5.53 |
| AUC | 59.37 |
| AUG | 10.87 |
| AUU | 57.40 |
| CAA | 15.99 |
| CAC | 11.85 |
| CAG | 16.30 |
| CAU | 11.83 |
| CCA | 3.92 |
| CCC | 14.55 |
| CCG | 9.68 |
| CCU | 16.79 |
| CGA | 62.78 |
| CGC | 60.37 |
| CGG | 9.26 |
| CGU | 60.30 |
| CUA | 11.98 |
| CUC | 18.82 |
| CUG | 60.32 |
| CUU | 18.12 |
| GAA | 63.67 |
| GAC | 38.98 |
| GAG | 63.24 |
| GAU | 37.06 |
| GCA | 43.12 |
| GCC | 10.43 |
| GCG | 42.27 |
| GCU | 41.95 |
| GGA | 23.06 |
| GGC | 55.93 |
| GGG | 36.68 |
| GGU | 53.69 |
| GUA | 48.35 |
| GUC | 23.09 |
| GUG | 45.43 |
| GUU | 56.47 |
| UAA | stop |
| UAC | 33.90 |
| UAG | stop |
| UAU | 33.44 |
| UCA | 26.18 |
| UCC | 12.27 |
| UCG | 30.02 |
| UCU | 32.65 |
| UGA | stop |
| UGC | 26.44 |
| UGG | 21.68 |
| UGU | 26.09 |
| UUA | 15.52 |
| UUC | 8.05 |
| UUG | 44.25 |
| UUU | 7.60 |

TABLE S8

Codon-specific elongation rates for *S. cerevisiae*.

| Codon | Codon-specific elongation rate [s$^{-1}$] |
|---|---|
| AAA | 39.61 |
| AAC | 46.99 |
| AAG | 69.91 |
| AAU | 46.99 |
| ACA | 31.84 |
| ACC | 57.40 |
| ACG | 7.23 |
| ACU | 57.40 |
| AGA | 63.49 |
| AGC | 27.25 |
| AGG | 6.64 |
| AGU | 27.25 |
| AUA | 14.29 |
| AUC | 64.73 |
| AUG | 36.11 |
| AUU | 64.73 |
| CAA | 52.70 |
| CAC | 46.49 |
| CAG | 4.54 |
| CAU | 46.49 |
| CCA | 62.11 |
| CCC | 9.34 |
| CCG | 64.19 |
| CCU | 9.34 |
| CGA | 45.98 |
| CGC | 46.28 |
| CGG | 11.05 |
| CGU | 46.28 |
| CUA | 17.82 |
| CUC | 1.79 |
| CUG | 18.18 |
| CUU | 1.79 |
| GAA | 70.86 |
| GAC | 72.97 |
| GAG | 10.42 |
| GAU | 72.97 |
| GCA | 37.24 |
| GCC | 41.15 |
| GCG | 38.63 |
| GCU | 41.15 |
| GGA | 25.46 |
| GGC | 77.24 |
| GGG | 18.60 |
| GGU | 77.24 |
| GUA | 15.74 |
| GUC | 65.35 |
| GUG | 15.34 |
| GUU | 65.35 |
| UAA | stop |
| UAC | 45.87 |
| UAG | stop |
| UAU | 45.87 |
| UCA | 23.05 |
| UCC | 56.02 |
| UCG | 7.23 |
| UCU | 56.02 |
| UGA | stop |
| UGC | 28.23 |
| UGG | 49.66 |
| UGU | 28.23 |
| UUA | 49.64 |
| UUC | 52.98 |
| UUG | 54.89 |
| UUU | 52.98 |

TABLE S9

Codon-specific elongation rates for HEK293.

| Codon | Codon-specific elongation rate [s$^{-1}$] |
|---|---|
| AAA | 21.21984 |
| AAC | 14.12447 |

TABLE S9-continued

Codon-specific elongation rates for HEK293.

| Codon | Codon-specific elongation rate [$s^{-1}$] |
|---|---|
| AAG | 11.23207 |
| AAU | 14.12483 |
| ACA | 10.48064 |
| ACC | 14.78216 |
| ACG | 7.33020 |
| ACU | 14.78260 |
| AGA | 1.59880 |
| AGC | 15.08409 |
| AGG | 7.37762 |
| AGU | 15.08453 |
| AUA | 2.51558 |
| AUC | 11.82971 |
| AUG | 34.86228 |
| AUU | 11.81255 |
| CAA | 12.59770 |
| CAC | 18.93839 |
| CAG | 27.28044 |
| CAU | 18.93835 |
| CCA | 8.84760 |
| CCC | 1.00958 |
| CCG | 5.92273 |
| CCU | 1.00958 |
| CGA | 17.13684 |
| CGC | 7.35781 |
| CGG | 10.10466 |
| CGU | 7.35781 |
| CUA | 3.35796 |
| CUC | 0.71702 |
| CUG | 16.39336 |
| CUU | 0.71704 |
| GAA | 9.11984 |
| GAC | 21.96470 |
| GAG | 5.48026 |
| GAU | 21.96470 |
| GCA | 5.89915 |
| GCC | 17.75464 |
| GCG | 6.04496 |
| GCU | 17.75464 |
| GGA | 8.12605 |
| GGC | 24.84194 |
| GGG | 11.61666 |
| GGU | 24.84194 |
| GUA | 13.09163 |
| GUC | 28.00956 |
| GUG | 41.11098 |
| GUU | 28.01011 |
| UAA | 171.67736 |
| UAC | 5.27462 |
| UAG | 171.67736 |
| UAU | 5.27632 |
| UCA | 21.12999 |
| UCC | 7.59376 |
| UCG | 3.59940 |
| UCU | 7.59376 |
| UGA | 171.67736 |
| UGC | 8.83135 |
| UGG | 13.32441 |
| UGU | 8.83135 |
| UUA | 15.73559 |
| UUC | 14.33256 |
| UUG | 4.20173 |
| UUU | 14.33295 |

TABLE S10

Codon-specific error frequencies for E. coli at a specific growth rate of 2.5 $h^{-1}$.

| Codon | Error frequency [$10^{-4}$] |
|---|---|
| AAA | 8.96 |
| AAC | 7.65 |
| AAG | 9.66 |

TABLE S10-continued

Codon-specific error frequencies for E. coli at a specific growth rate of 2.5 $h^{-1}$.

| Codon | Error frequency [$10^{-4}$] |
|---|---|
| AAU | 8.37 |
| ACA | 3.54 |
| ACC | 6.74 |
| ACG | 2.17 |
| ACU | 3.55 |
| AGA | 6.80 |
| AGC | 10.90 |
| AGG | 9.61 |
| AGU | 11.55 |
| AUA | 26.51 |
| AUC | 0.69 |
| AUG | 18.24 |
| AUU | 1.22 |
| CAA | 8.94 |
| CAC | 12.61 |
| CAG | 8.80 |
| CAU | 12.77 |
| CCA | 38.82 |
| CCC | 6.98 |
| CCG | 15.52 |
| CCU | 8.49 |
| CGA | 0.44 |
| CGC | 1.03 |
| CGG | 18.21 |
| CGU | 1.05 |
| CUA | 14.13 |
| CUC | 9.11 |
| CUG | 1.04 |
| CUU | 11.02 |
| GAA | 1.08 |
| GAC | 3.18 |
| GAG | 1.18 |
| GAU | 4.40 |
| GCA | 2.49 |
| GCC | 14.36 |
| GCG | 2.92 |
| GCU | 3.08 |
| GGA | 8.91 |
| GGC | 1.64 |
| GGG | 4.06 |
| GGU | 2.33 |
| GUA | 1.97 |
| GUC | 6.99 |
| GUG | 3.19 |
| GUU | 1.78 |
| UAA | stop |
| UAC | 1.82 |
| UAG | stop |
| UAU | 2.19 |
| UCA | 2.37 |
| UCC | 7.13 |
| UCG | 3.15 |
| UCU | 2.79 |
| UGA | stop |
| UGC | 5.12 |
| UGG | 4.64 |
| UGU | 5.59 |
| UUA | 6.11 |
| UUC | 19.47 |
| UUG | 2.16 |
| UUU | 26.22 |

TABLE S11

Codon-specific error frequencies for S. cerevisiae.

| Codon | Error frequency [$10^{-4}$] |
|---|---|
| AAA | 2.08 |
| AAC | 2.00 |
| AAG | 0.40 |
| AAU | 2.00 |

TABLE S11-continued

Codon-specific error frequencies for *S. cerevisiae*.

| Codon | Error frequency [$10^{-4}$] |
|---|---|
| ACA | 2.28 |
| ACC | 1.02 |
| ACG | 11.78 |
| ACU | 1.02 |
| AGA | 0.56 |
| AGC | 3.66 |
| AGG | 11.67 |
| AGU | 3.66 |
| AUA | 5.82 |
| AUC | 0.93 |
| AUG | 1.68 |
| AUU | 0.93 |
| CAA | 1.17 |
| CAC | 1.40 |
| CAG | 17.04 |
| CAU | 1.40 |
| CCA | 0.66 |
| CCC | 9.20 |
| CCG | 0.26 |
| CCU | 9.20 |
| CGA | 1.14 |
| CGC | 1.03 |
| CGG | 4.95 |
| CGU | 1.03 |
| CUA | 3.55 |
| CUC | 49.82 |
| CUG | 2.69 |
| CUU | 49.82 |
| GAA | 0.69 |
| GAC | 1.04 |
| GAG | 8.18 |
| GAU | 1.04 |
| GCA | 1.72 |
| GCC | 2.24 |
| GCG | 0.97 |
| GCU | 2.24 |
| GGA | 3.39 |
| GGC | 0.76 |
| GGG | 3.35 |
| GGU | 0.76 |
| GUA | 5.04 |
| GUC | 1.10 |
| GUG | 4.37 |
| GUU | 1.10 |
| UAA | stop |
| UAC | 1.55 |
| UAG | stop |
| UAU | 1.55 |
| UCA | 2.69 |
| UCC | 0.97 |
| UCG | 10.94 |
| UCU | 0.97 |
| UGA | stop |
| UGC | 3.15 |
| UGG | 0.53 |
| UGU | 3.15 |
| UUA | 0.77 |
| UUC | 1.47 |
| UUG | 0.84 |
| UUU | 1.47 |

TABLE S12

Codon-specific error frequencies for HEK293 cells.

| Codon | Error frequency [$10^{-4}$] |
|---|---|
| AAA | 4.88 |
| AAC | 15.46 |
| AAG | 22.17 |
| AAU | 15.46 |
| ACA | 15.16 |
| ACC | 10.59 |

TABLE S12-continued

Codon-specific error frequencies for HEK293 cells.

| Codon | Error frequency [$10^{-4}$] |
|---|---|
| ACG | 29.21 |
| ACU | 10.59 |
| AGA | 109.98 |
| AGC | 11.34 |
| AGG | 31.56 |
| AGU | 11.34 |
| AUA | 104.34 |
| AUC | 22.37 |
| AUG | 4.62 |
| AUU | 22.41 |
| CAA | 15.84 |
| CAC | 8.77 |
| CAG | 4.56 |
| CAU | 8.77 |
| CCA | 16.90 |
| CCC | 179.23 |
| CCG | 29.98 |
| CCU | 179.23 |
| CGA | 5.28 |
| CGC | 27.38 |
| CGG | 20.58 |
| CGU | 27.38 |
| CUA | 55.73 |
| CUC | 343.60 |
| CUG | 17.06 |
| CUU | 343.54 |
| GAA | 19.98 |
| GAC | 9.73 |
| GAG | 56.89 |
| GAU | 9.73 |
| GCA | 32.46 |
| GCC | 11.97 |
| GCG | 41.88 |
| GCU | 11.97 |
| GGA | 21.81 |
| GGC | 7.80 |
| GGG | 22.57 |
| GGU | 7.80 |
| GUA | 19.95 |
| GUC | 8.50 |
| GUG | 3.69 |
| GUU | 8.49 |
| UAA | stop |
| UAC | 35.56 |
| UAG | stop |
| UAU | 35.54 |
| UCA | 3.94 |
| UCC | 22.90 |
| UCG | 38.16 |
| UCU | 22.90 |
| UGA | stop |
| UGC | 20.19 |
| UGG | 6.62 |
| UGU | 20.19 |
| UUA | 7.06 |
| UUC | 11.71 |
| UUG | 81.58 |
| UUU | 11.71 |

3. Optimizing Protein Translation with the Codon-Specific Elongation Model and Protein Expression Score 3.1 the Protein Expression Score While the COSEM current pj of a sequence j results from a mechanistic model of protein translation and can as such already be considered as a predictor for protein expression we would like to integrate further potentially influencing variables into a full model or protein expression score for a sequence j, i.e. depending on a vector of variables $\vec{x}_j = (x_{1j}, x_{2j}, \ldots) = (p_j, \ldots)$ with the COSEM current pj being one component.

$$\hat{f}(\vec{x}_j) = \sum_k \hat{f}_k(x_{kj})$$

wherein the index k runs along the following features $x_{kj}$ in sequence j to be described by base functions $f_k$ which are estimated as described in the following with reference to FIG. 4. The functions in the above formula relate to the following sequence features:

Cosem Current $p_j$ (protein per time) [protein/(s mRNA)]
average elongation rate [codon/s]
bottleneck index [codon/s], minimum over average elongation rates seen in a sliding window of 10 codons
ramp of slow codons or ramp index [codon/s], i.e. average elongation rate in the first 30 codons
mRNA transcript abundance [$\log_{10}$(FPKM)]
GC3% or GC3 content
   sequence accuracy
   5' folding energy [kcal/mol]
   influence of predefined motifs
   5' number of hairpins
   number of AGG in first 30 codons
   number of out-of-frame stop-codons Note that the influence of predefined motifs, the number of hairpins, number of AGG in first 30 codons, out-of-frame stop-codons, mRNA transcript levels and a ramp of slow codons are not generally included in the scoring function, but may be included in order to improve the scoring function for certain target organisms.

The factors are weighted with component-wise smoothing splines $f_k$ and modeled separately through least-square regression (25) with log-transformed protein abundance data from PaxDb in E. coli, S. cerevisiae and HEK293 and using available data on protein and transcript abundance (55) where available. FIGS. 11-13 show all covariates with their respective weights in the protein expression score for E. coli, S. cerevisiae and HEK293.

3.2 Optimizing Protein Translation

While the protein expression score translates sequence features into a protein expression score, it also allows to address the inverse problem, i.e. to select sequences with features that maximize the protein expression score and in this way derive optimized sequences.

Sequence Proposals

For sequence proposals elongation rates and accuracies at each position i in the proposed test sequence j, $\omega_{ij}$ $a_{ij}$, are normalized to those seen in the wild type or starting sequence $\omega_{iwt}$ $a_{iwt}$. The first test sequence j is generated by choosing at each position i in the sequence the codon that maximizes $$\omega_1 \frac{\omega_{i,j}}{\omega_{i,wt}} + \omega_2 \frac{a_{i,j}}{a_{i,wt}},$$

assuming that this locally optimal sequence is close to the globally optimal sequence (defined as maximizing the protein expression score). Subsequent test sequences j are drawn by selecting codons at each position i with probabilities proportional to $$\omega_1 \frac{\omega_{i,j}}{\omega_{i,wt}} + \omega_2 \frac{a_{i,j}}{a_{i,wt}}.$$

The factors w1 and w2 allow for weighting of codon elongation rates versus accuracies in the codon proposals.

Sequence Selection

For each proposed sequence j the sequence features as contained in the protein expression score) are evaluated. In particular, the accuracy of the whole sequence j of n codons is calculated as the probability of making no mistake aj=a1j . . . anj (accordingly for the wild type sequence). The protein production rate or COSEM current pj of a test sequence j is derived from simulations of the codon-specific elongation model (COSEM) after equilibration. From proposed sequence j's features the protein expression score is derived and both the sequence and its score are kept for further reference if the score maximizes earlier achieved scores. The optimization terminates as soon as the coefficient of variation among the last 100 maximal protein expression scores falls below a given threshold as a measure of the decreasing slope/equilibration.

A sensible combination of maximizing COSEM current and translation accuracy is particularly relevant in biological settings in which collective phenomena as ribosome jamming take place: a local improvement on accuracy may not lead to a decreased COSEM current, even in cases that involve a local decrease in elongation rate.

3.3 Bacterial Strains, Plasmids and Oligonucleotides

*Salmonella enterica* serovar Typhimurium (S. Typhimurium) strain SL7207 ($\Delta$hisG, $\Delta$aroA) is an attenuated derivative of the wildtype isolate SL1344 with an auxotrophy for aromatic amino acids (24). Originally, this strain was generously provided by Bruce Stocker. Strain SL7207$\Delta$araBAD was derived from the original strain and has been recently described (35). Strain SL7207$\Delta$araBAD$\Delta$manA (SL-361) was constructed in this work by $\lambda$-Red recombinase mediated deletion of manA. E. coli strain NEB5$\alpha$ (New England Biolabs) was used for general cloning purposes.

Oligonucleotides used in this work are listed in Table S15.

TABLE S15

Oligonucleotides used.

| Name | Target | 5'-3' sequence |
|---|---|---|
| oHL20 | kan of pKD4 | GCCTGCTTGCCGAATATC |
| oJT1 | pKD4 | ATGCAAAAACTCATTAACTCAGTGCA AAACTATGCCTGGGTGTGTAGGCTGG AGCTGCTTC |
| oJT2 | pKD4 | CTACAGCTTGTTATAAACACGCGCTA AACGGCCCGTGCCGCTGGCGCATATG AATATCCTCCTTAG |
| oJT4 | downstream region of genomic manA | GAAACCAGGCGGATTAAACC |

TABLE S15-continued

Oligonucleotides used.

| Name | Target | 5'-3' sequence |
|---|---|---|
| oJT7 | wt manA cloning | GGATATCATATGCAAAAACTCATTAACTCAG |
| oJT8 | wt manA cloning | GGATATCACTAGTCTACAGCTTGTTATAAACACG |
| oJT11 | cam | TCCGGCCTTTATTCACATTC |
| oJT12 | cam | CGTTTCAGTTTGCTCATGGA |
| oJT13 | manA promoter | CCTCCCATTGATCTCCACAT |
| oJT14 | manA2 | GGTCAGTGCGGTTTTGCTAC |
| oJT16 | manA3, 8, 9, 10 | GATTGGCGATGCCATAAAGT |
| oJT17 | wt manA | ATTGGCGATGCCATAAAGTT |
| oJT21 | manA | GTTTTAGAGCCCCATGCGTA |
| oJT23 | manA5 | GTTTGCGATGCCGTACAGTT |
| oJT24 | manA6 | GGGTTGGCTATACCGTACAA |
| oJT27 | manA1 | CCATACAGTTCGGTCAGTGC |
| oJT28 | manA4 | TGGTTGTTGTTGTGGATTGG |

Plasmid pKD4 was used as DNA template for amplification of the linear DNA fragment for depletion of manA from strain SL7207 and pKD46 was used for the temporal expression λ-Red recombinase (7). Codon-adapted manA and ova variants were synthesized, sequenced and subcloned by Geneart/Life Technologies (cf. Table S16).

TABLE S16

Sequences used; CDS denotes the coding sequences which are shown below as SEQ ID NOs: 18 to 38.

| Plasmid name | gid | CDS name | DNA # | GK | Longname | Alternate Name | CDS |
|---|---|---|---|---|---|---|---|
| pETcoco-I | 0 | w/o | 375 | 393 | | | 18 |
| pJT6a | wt | manAwt | 685 | 397 | manA_orig | Wildtype | 18 |
| pJT7a | 1 | manA1 | 680 | 531 | manA_opt_and_slow_before_secondary | Geneart + Secondary | 19 |
| pJT8a | 2 | manA2 | 678 | 532 | man_opt_geneart | Geneart | 20 |
| pJT9a | 3 | manA3 | 682 | 533 | manA_opt_and_ramp | Geneart + Ramp | 21 |
| pJT27a | 4 | manA4a | 746 | 528 | manA_origOptSpeedFold | Deoptimized | 22 |
| pJT28 | 5 | manA5 | 727 | 460 | manA_origOpt5050 | Intermediate | 23 |
| pJT29 | 6 | manA6 | 729 | 461 | manA_origAcc | Accuracy | 24 |
| pJT36 | 7 | manA7 | 738 | 524 | manaGeschwindigkeit | Speed | 25 |
| pJT37 | 8 | manA8 | 740 | 525 | manA_origAccRamp | Accuracy + Ramp | 26 |
| pJT38 | 9 | manA9 | 742 | 526 | manA_origOpt5050Ramp | Intermediate + Ramp | 27 |
| pJT39 | 10 | manA10 | 744 | 527 | manaGeschwindigkeitRamp | Speed + Ramp | 28 |
| pJT27 | | manA4 | 725 | 459 | manA4 different clone | | 29 |
| pJT27b | | manA4b | 748 | 529 | manA4 different clone | | 30 |
| pJT27c | | manA4c | 750 | 530 | manA4 different clone | | 31 |
| 5'utr | | | | | | | 32 |
| 5'utr promoter | | | | | | | 33 |
| ova_origOptAcc | pJT15 | | | | | Accuracy | 34 |
| ovasyn | pJT16 | | | | | Geneart | 35 |
| ova_orig5050 | pJT I 7 | | | | | Intermediate | 36 |
| ova_orig | pJT18 | | | | | Wildtype | 37 |
| ova_origOptSpeed | pJT19 | | | | | Deoptimized | 38 |

SEQ ID NO: 18
ATGCAAAAACTCATTAACTCAGTGCAAAACTATGCCTGGGGAAGTAAAACTGCGTT

AACGGAACTTTATGGCATCGCCAATCCGCAGCAGCAGCCAATGGCTGAACTCTGGA

```
                                             -continued
TGGGCGCGCATCCCAAAAGCAGCTCGCGAATCACCACCGCCAACGGCGAAACCGTC

TCCCTGCGTGACGCCATCGAAAAGAATAAAACCGCCATGCTGGGCGAAGCGGTAGC

CAACCGTTTCGGCGAACTGCCGTTTCTGTTTAAAGTACTGTGCGCCGCACAACCGCT

CTCTATTCAGGTGCACCCGAATAAACGCAACTCCGAAATCGGTTTCGCGAAAGAAA

ATGCGGCGGGTATCCCCATGGATGCCGCAGAGCGGAACTATAAAGATCCTAACCAT

AAACCAGAGCTGGTTTTTGCCCTGACGCCTTTCCTGGCGATGAACGCGTTCCGCGAA

TTTTCTGACATTGTCTCTTTACTGCAACCTGTCGCCGGCGCGCATTCCGCTATCGCCC

ACTTTTTGCAGGTGCCGAATGCTGAACGTCTGAGCCAGCTTTTCGCCAGCCTGTTGA

ATATGCAAGGCGAAGAAAAATCCCGCGCGTTAGCCGTACTCAAAGCGGCGCTTAAC

AGCCAGCAAGGCGAACCGTGGCAAACGATCCGCGTGATTTCAGAGTATTATCCTGA

CGACAGCGGGCTTTTCTCTCCTTTGTTGCTGAATGTGGTCAAACTGAATCCCGGCGA

GGCGATGTTCCTGTTTGCTGAAACGCCTCATGCTTATCTGCAGGGCGTTGCGCTGGA

AGTCATGGCGAACTCCGATAACGTTCTGCGCGCTGGCCTTACGCCAAAATATATCGA

CATCCCTGAGCTGGTCGCGAACGTGAAGTTCGAACCTAAGCCTGCCGGCGAGTTGCT

GACTGCCCCGGTGAAAAGCGGCGCGGAGCTGGACTTCCCAATTCCGGTTGACGATTT

TGCTTTTTCACTGCACGACCTGGCGCTTCAGGAGACGAGCATCGGCCAACACAGCGC

CGCGATTCTGTTCTGCGTTGAGGGTGAGGCGGTGTTACGTAAAGATGAACAGCGTCT

GGTACTGAAGCCGGGTGAATCTGCCTTTATCGGCGCGGATGAGTCTCCGGTTAACGC

CAGCGGCACGGGCCGTTTAGCGCGTGTTTATAACAAGCTGTAG

SEQ ID NO: 19
ATGCAGAAACTGATTAATAGCGTGCAGAATTATGCATGGGGATCGAAAACCGCACT

GACCGAACTGTATGGTATTGCAAATCCGCAGCAGCAGCCAATGGCAGAACTGTGGA

TGGGTGCACATCCGAAAAGCAGCTCCCGAATTACCACCGCAAATGGTGAAACCGTT

AGCCTGCGTGATGCAATCGAAAAAAACAAAACCGCCATGCTGGGTGAAGCAGTTGC

AAATCGTTTTGGTGAACTGCCGTTTCTGTTTAAAGTTCTGTGTGCAGCACAGCCGCT

GAGCATTCAGGTTCATCCGAATAAACGTAATAGCGAAATTGGCTTTGCCAAAGAAA

ATGCAGCAGGTATTCCCATGGATGCAGCAGAACGTAACTATAAAGATCCGAATCAT

AAACCAGAACTGGTTTTTGCACTGACCCCGTTTCTGGCAATGAATGCATTTCGTGAA

TTTAGCGATATTGTGAGCCTGCTGCAGCCGGTTGCCGGTGCCCATAGCGCAATTGCA

CATTTTCTGCAGGTTCCGAATGCCGAACGTCTGAGCCAGCTGTTTTGCAAGCCTGCTG

AATATGCAGGGTGAAGAAAAAGCCGTGCACTGGCAGTTCTGAAAGCAGCACTGAA

TAGCCAGCAGGGCGAACCGTGGCAGACCATTCGTGTTATTAGCGAATATTATCCGG

ATGATAGCGGTCTTTTTAGCCCTCTGCTGCTGAATGTTGTTAAACTGAATCCGGGTG

AAGCCATGTTTCTGTTCGCAGAAACACCGCATGCTTATCTGCAGGGTGTTGCACTGG

AAGTTATGGCAAATAGCGATAATGTTCTGCGTGCAGGTCTGACCCCGAAATACATTG

ATATTCCAGAACTGGTTGCCAACGTGAAATTTGAACCGAAACCGGCAGGCGAACTG

CTGACCGCACCGGTAAAAGCGGTGCAGAACTGGATTTTCCGATTCCGGTGGATGAT

TTTGCATTTAGTTTGCATGATCTGGCACTGCAAGAAACCAGCATTGGTCAGCATAGC

GCAGCAATTCTGTTTTGTGTTGAAGGTGAAGCCGTTCTGCGTAAAGATGAACAGCGT

CTGGTTCTGAAACCTGGTGAAAGCGCATTTATTGGTGCAGATGAAAGTCCGGTTAAT

GCAAGCGGCACCGGTCGTCTGGCACGTGTTTATAACAAACTGTAA
```

SEQ ID NO: 20

```
ATGCAGAAACTGATTAATAGCGTGCAGAATTATGCATGGGGTAGCAAAACCGCACT
GACCGAACTGTATGGTATTGCAAATCCGCAGCAGCAGCCGATGGCAGAACTGTGGA
TGGGTGCACATCCGAAAAGCAGCAGTCGTATTACCACCGCAAATGGTGAAACCGTT
AGCCTGCGTGATGCAATCGAAAAAAACAAAACCGCCATGCTGGGTGAAGCAGTTGC
AAATCGTTTTGGTGAACTGCCGTTTCTGTTTAAAGTTCTGTGTGCAGCACAGCCGCT
GAGCATTCAGGTTCATCCGAATAAACGTAATAGCGAAATTGGCTTTGCCAAAGAAA
ATGCAGCAGGTATTCCGATGGATGCAGCAGAACGTAACTATAAAGATCCGAATCAT
AAACCGGAACTGGTTTTTGCACTGACCCCGTTTCTGGCAATGAATGCATTTCGTGAA
TTTAGCGATATTGTGAGCCTGCTGCAGCCGGTTGCCGGTGCACATAGCGCAATTGCA
CATTTTCTGCAGGTTCCGAATGCAGAACGTCTGAGCCAGCTGTTTGCAAGCCTGCTG
AATATGCAGGGTGAAGAAAAAAGCCGTGCACTGGCAGTTCTGAAAGCAGCACTGAA
TAGCCAGCAGGGCGAACCGTGGCAGACCATTCGTGTTATTAGCGAATATTATCCGG
ATGATAGCGGTCTGTTTAGCCCTCTGCTGCTGAATGTTGTTAAACTGAATCCGGGTG
AAGCCATGTTTCTGTTCGCAGAAACACCGCATGCATATCTGCAGGGTGTTGCACTGG
AAGTTATGGCAAATAGCGATAATGTTCTGCGTGCAGGTCTGACCCCGAAATACATTG
ATATTCCAGAACTGGTTGCCAACGTGAAATTTGAACCGAAACCGGCAGGCGAACTG
CTGACCGCACCGGTTAAAAGCGGTGCAGAACTGGATTTTCCGATTCCGGTGGATGAT
TTTGCATTTAGTCTGCATGATCTGGCACTGCAAGAAACCAGCATTGGTCAGCATAGC
GCAGCAATTCTGTTTTGTGTTGAAGGTGAAGCCGTTCTGCGTAAAGATGAACAGCGT
CTGGTTCTGAAACCTGGTGAAAGCGCATTTATTGGTGCAGATGAAAGTCCGGTTAAT
GCAAGCGGCACCGGTCGTCTGGCACGTGTTTATAACAAACTGTAA
```

SEQ ID NO: 21

```
ATGCAAAAACTCATTAACTCAGTGCAAAACTATGCCTGGGGAAGTAAAACTGCGTT
AACGGAACTTTATGGCATCGCCAATCCTCAGCAGCAGCCAATGGCTGAACTCTGGAT
GGGCGCGCATCCCAAAAGCTCATCGCGAATCACGACCGCGAATGGTGAAACCGTTA
GCCTGCGTGATGCAATCGAAAAAAACAAAACCGCCATGCTGGGTGAAGCAGTTGCA
AATCGTTTTGGTGAACTGCCGTTTCTGTTTAAAGTTCTGTGTGCAGCACAGCCGCTG
AGCATTCAGGTTCATCCGAATAAACGTAATAGCGAAATTGGCTTTGCCAAAGAAAA
TGCAGCAGGTATTCCGATGGATGCAGCAGAACGTAACTATAAAGATCCGAATCATA
AACCAGAACTGGTTTTTGCACTGACCCCGTTTCTGGCAATGAATGCATTTCGTGAAT
TTAGCGATATTGTGAGCCTGCTGCAGCCGGTTGCCGGTGCCCATAGCGCAATTGCAC
ATTTTCTGCAGGTTCCGAATGCCGAACGTCTGAGCCAGCTGTTTGCAAGCCTGCTGA
ATATGCAGGGTGAAGAAAAAAGCCGTGCACTGGCAGTTCTGAAAGCAGCACTGAAT
AGCCAGCAGGGCGAACCGTGGCAGACCATTCGTGTTATTAGCGAATATTATCCGGA
TGATAGCGGTCTTTTTAGCCCTCTGCTGCTGAATGTTGTTAAACTGAATCCGGGTGA
AGCCATGTTTCTGTTCGCAGAAACACCGCATGCTTATCTGCAGGGTGTTGCACTGGA
AGTTATGGCAAATAGCGATAATGTTCTGCGTGCAGGTCTGACCCCGAAATACATTGA
TATTCCAGAACTGGTTGCCAACGTGAAATTTGAACCGAAACCGGCAGGCGAACTGC
TGACCGCACCGGTTAAAAGCGGTGCAGAACTGGATTTTCCGATTCCGGTGGATGATT
TTGCATTTAGTTTGCATGATCTGGCACTGCAAGAAACCAGCATTGGTCAGCATAGCG
CAGCAATTCTGTTTTGTGTTGAAGGTGAAGCCGTTCTGCGTAAAGATGAACAGCGTC
```

```
TGGTTCTGAAACCTGGTGAAAGCGCATTTATTGGTGCAGATGAAAGTCCGGTTAATG
CAAGCGGCACCGGTCGTCTGGCACGTGTTTATAACAAACTGTAA
```

SEQ ID NO: 22
```
ATGCAAAAGCTAATAAATTCCGTCCAAAATTATGCCTGGGGATCCAAGACCGCCCT
AACCGAGCTATATGGAATAGCCAATCCACAACAACAACCAATGGCCGAGCTATGGA
TGGGAGCCCATCCAAAGTCCTCCTCCCGGATAACCACCGCCAATGGAGAGACCGTC
TCCCTACGGGATGCCATAGAGAAGAATAAGACCGCCATGCTAGGAGAGGCCGTCGC
CAATCGGTTTGGAGAGCTACCATTTCTATTTAAGGTCCTATGTGCCGCCCAACCACT
ATCCATACAAGTCCATCCAAATAAGCGGAATTCCGAGATAGGATTTGCCAAGGAGA
ATGCCGCCGGAATACCAATGGATGCCGCCGAGCGGAATTATAAGGATCCAAATCAT
AAGCCAGAGCTAGTCTTTGCCCTAACCCCATTTCTAGCCATGAATGCCTTTCGGGAG
TTTTCCGATATAGTCTCCCTACTACAACCAGTCGCCGGAGCCCATTCCGCCATAGCC
CATTTTCTACAAGTCCCAAATGCCGAGCGGCTATCCCAACTATTTGCCTCCCTACTA
AATATGCAAGGAGAGGAGAAGTCCCGGGCCCTAGCCGTCCTAAAGGCCGCCCTAAA
TTCCCAACAAGGAGAGCCATGGCAAACCATACGGGTCATATCCGAGTATTATCCAG
ATGATTCCGGACTATTTTCCCCACTACTACTAAATGTCGTCAAGCTAAATCCAGGAG
AGGCCATGTTTCTATTTGCCGAGACCCCACATGCCTATCTACAAGGAGTCGCCCTAG
AGGTCATGGCCAATTCCGATAATGTCCTACGGGCCGGACTAACCCCAAAGTATATA
GATATACCAGAGCTAGTCGCCAATGTCAAGTTTGAGCCAAAGCCAGCCGGAGAGCT
ACTAACCGCCCCAGTCAAGTCCGGAGCCGAGCTAGATTTTCCAATACCAGTCGATGA
TTTTGCCTTTTCCCTACATGATCTAGCCCTACAAGAGACCTCCATAGGACAACATTCC
GCCGCCATACTATTTTGTGTCGAGGGAGAGGCCGTCCTACGGAAGGATGAGCAACG
GCTAGTCCTAAAGCCAGGAGAGTCCGCCTTTATAGGAGCCGATGAGTCCCCAGTCA
ATGCCTCCGGAACCGGACGGCTAGCCCGGGTCTATAATAAGCTATAG
```

SEQ ID NO: 23
```
ATGCAGAAACTGATCAACTCAGTTCAGAACTACGCATGGGGCTCAAAAACGGCAC
TGACGGAACTGTACGGCATCGCAAACCCCCAGCAGCAGCCCATGGCAGAACTGTG
GATGGGCGCACACCCCAAATCATCATCACGAATCACGACGGCAAACGGCGAAAC
GGTTTCACTGCGAGACGCAATCGAAAAAAACAAAACGGCAATGCTGGGCGAAGC
AGTTGCAAACCGATTCGGCGAACTGCCCTTCCTGTTCAAAGTTCTGTGCGCAGCAC
AGCCCCTGTCAATCCAGGTTCACCCCAACAAACGAAACTCAGAAATCGGCTTCGC
AAAAGAAAACGCAGCAGGCATCCCCATGGACGCAGCAGAACGAAACTACAAAGA
CCCCAACCACAAACCCGAACTGGTTTTCGCACTGACGCCCTTCCTGGCAATGAAC
GCATTCCGAGAATrCTCAGACATCGTTTCACTGCTGCAGCCCGTTGCAGGCGCAC
ACTCAGCAATCGCACACTTCCTGCAGGTTCCCAACGCAGAACGACTGTCACAGCT
GTTCGCATCACTGCTGAACATGCAGGGCGAAGAAAAATCACGAGCACTGGCAGTT
CTGAAAGCAGCACTGAACTCACAGCAGGGCGAACCCTGGCAGACGATCCGAGTT
ATCTCAGAATACTACCCCGACGACTCAGGCCTGTTCTCACCCCTGCTGCTGAACGT
TGTTAAACTGAACCCCGGCGAAGCAATGTTCCTGTTCGCAGAAACGCCCCACGCA
TACCTGCAGGGCGTTGCACTGGAAGTTATGGCAAACTCAGACAACGTTCTGCGAG
CAGGCCTGACGCCCAAATACATCGACATCCCCGAACTGGTTGCAAACGTTAAATT
CGAACCCAAACCCGCAGGCGAACTGCTGACGGCACCCGTTAAATCAGGCGCAGA
```

-continued
ACTGGACTTCCCCATCCCCGTTGACGACTTCGCATTCTCACTGCACGACCTGGCAC

TGCAGGAAACGTCAATCGGCCAGCACTCAGCAGCAATCCTGTTCTGCGTTGAAGG

CGAAGCAGTTCTGCGAAAAGACGAACAGCGACTGGTTCTGAAACCCGGCGAATC

AGCATTCATCGGCGCAGACGAATCACCCGTTAACGCATCAGGCACGGGCCGACTG

GCACGAGTTTACAACAAACTGTAG

SEQ ID NO: 24
ATGCAAAAGCTCATAAACTCTGTGCAAAATTATGCATGGGGTAGCAAGACTGCTCT

AACAGAATTGTACGGTATAGCCAACCCGCAACAGCAACCTATGGCCGAACTATGGA

TGGGTGCTCACCCAAAGTCGAGCTCCCGGATAACTACCGCCAACGGAGAGACCGTC

TCACTTAGAGATGCGATTGAGAAGAATAAAACCGCCATGCTTGGGGAGGCGGTTGC

CAATCGGTTTGGTGAGTTACCATTTCTCTTTAAAGTATTATGTGCCGCCCAGCCACTC

TCGATACAGGTGCATCCGAATAAAAGAAATAGTGAGATAGGATTTGCCAAAGAAAA

CGCAGCAGGGATACCAATGGACGCCGCAGAGCGGAATTATAAAGACCCAAATCACA

AGCCCGAGTTAGTGTTCGCCTTAACCCCATTTCTAGCCATGAACGCATTCAGAGAGT

TCAGTGATATAGTCAGCCTACTACAGCCAGTCGCTGGAGCCCATAGCGCTATCGCCC

ACTTTCTTCAGGTGCCAAACGCCGAACGGCTCAGCCAACTTTTTGCGAGTCTATTAA

ATATGCAGGGTGAGGAAAAGTCGAGGGCACTTGCCGTGCTAAAGGCAGCCCTAAAT

TCCCAGCAAGGAGAGCCATGGCAAACTATACGCGTCATATCGGAATACTATCCTGA

CGACTCCGGGCTGTTTAGTCCGCTACTACTTAACGTCGTTAAACTAAATCCGGGCGA

AGCGATGTTTTTATTTGCTGAAACCCCTCACGCCTATCTTCAGGGTGTCGCCCTCGAA

GTGATGGCTAATTCAGATAATGTCTTACGGGCCGGTCTCACACCAAAGTATATAGAC

ATCCCAGAATTAGTCGCCAACGTGAAGTTCGAACCAAAGCCGGCCGGCGAGCTCTT

GACCGCCCCAGTCAAGAGCGGTGCTGAACTAGATTTTCCAATACCAGTCGACGACTT

CGCCTTTTCCCTCCATGACCTTGCCCTTCAGGAGACCTCCATAGGACAGCATAGCGC

CGCAATACTATTCTGCGTCGAAGGAGAAGCCGTGCTCCGGAAGGATGAGCAACGGC

TTGTGTTGAAGCCAGGAGAGAGCGCATTCATAGGAGCCGATGAGAGTCCGGTTAAT

GCTTCCGGTACCGGTAGACTAGCCAGGGTGTATAACAAACTGTAG

SEQ ID NO: 25
ATGCAGAAACTGATCAACTCTGTTCAGAACTACGCATGGGGCTCTAAAACGGCACT

GACGGAACTGTACGGCATCGCAAACCCTCAGCAGCAGCCTATGGCAGAACTGTGGA

TGGGCGCACACCCTAAATCTTCTTCTCGAATCACGACGGCAAACGGCGAAACGGTTT

CTCTGCGAGACGCAATCGAAAAAAACAAAACGGCAATGCTGGGCGAAGCAGTTGCA

AACCGATTCGGCGAACTGCCTTTCCTGTTCAAAGTTCTGTGCGCAGCACAGCCTCTG

TCTATCCAGGTTCACCCTAACAAACGAAACTCTGAAATCGGCTTCGCAAAAGAAAA

CGCAGCAGGCATCCCTATGGACGCAGCAGAACGAAACTACAAAGACCCTAACCACA

AACCTGAACTGGTTTTCGCACTGACGCCTTTCCTGGCAATGAACGCATTCCGAGAAT

TCTCTGACATCGTTTCTCTGCTGCAGCCTGTTGCAGGCGCACACTCTGCAATCGCAC

ACTTCCTGCAGGTTCCTAACGCAGAACGACTGTCTCAGCTGTTCGCATCTCTGCTGA

ACATGCAGGGCGAAGAAAAATCTCGAGCACTGGCAGTTCTGAAAGCAGCACTGAAC

TCTCAGCAGGGCGAACCTTGGCAGACGATCCGAGTTATCTCTGAATACTACCCTGAC

GACTCTGGCCTGTTCTCTCCTCTGCTGCTGAACGTTGTTAAACTGAACCCTGGCGAA

GCAATGTTCCTGTTCGCAGAAACGCCTCACGCATACCTGCAGGGCGTTGCACTGGAA

```
GTTATGGCAAACTCTGACAACGTTCTGCGAGCAGGCCTGACGCCTAAATACATCGAC

ATCCCTGAACTGGTTGCAAACGTTAAATTCGAACCTAAACCTGCAGGCGAACTGCTG

ACGGCACCTGTTAAATCTGGCGCAGAACTGGACTTCCCTATCCCTGTTGACGACTTC

GCATTCTCTCTGCACGACCTGGCACTGCAGGAAACGTCTATCGGCCAGCACTCTGCA

GCAATCCTGTTCTGCGTTGAAGGCGAAGCAGTTCTGCGAAAAGACGAACAGCGACT

GGTTCTGAAACCTGGCGAATCTGCATTCATCGGCGCAGACGAATCTCCTGTTAACGC

ATCTGGCACGGGCCGACTGGCACGAGTTTACAACAAACTGTAA
```

SEQ ID NO: 26
```
ATGCAAAAACTCATTAACTCAGTGCAAAACTATGCCTGGGGAAGTAAAACTGCGTT

AACGGAACTTTATGGCATCGCCAATCCTCAGCAGCAGCCAATGGCTGAACTCTGGAT

GGGCGCGCATCCCAAAAGCTCATCGCGAATCACGACCGCAAACGGCGAAACGGTTT

CACTGCGAGACGCAATCGAAAAAAACAAAACGGCAATGCTGGGCGAAGCAGTTGC

AAACCGATTCGGCGAACTGCCCTTCCTGTTCAAAGTTCTGTGCGCAGCACAGCCCCT

GTCAATCCAGGTTCACCCCAACAAACGAAACTCAGAAATCGGCTTCGCAAAAGAAA

ACGCAGCAGGCATCCCCATGGACGCAGCAGAACGAAACTACAAAGACCCCAACCAC

AAACCCGAACTGGTTTTCGCACTGACGCCCTTCCTGGCAATGAACGCATTCCGAGAA

TTCTCAGACATCGTTTCACTGCTGCAGCCCGTTGCAGGCGCACACTCAGCAATCGCA

CACTTCCTGCAGGTTCCCAACGCAGAACGACTGTCACAGCTGTTCGCATCACTGCTG

AACATGCAGGGCGAAGAAAATCACGAGCACTGGCAGTTCTGAAAGCAGCACTGA

ACTCACAGCAGGGCGAACCCTGGCAGACGATCCGAGTTATCTCAGAATACTACCCC

GACGACTCAGGCCTGTTCTCACCCCTGCTGCTGAACGTTGTTAAACTGAACCCCGGC

GAAGCAATGTTCCTGTTCGCAGAAACGCCCCACGCATACCTGCAGGGCGTTGCACTG

GAAGTTATGGCAAACTCAGACAACGTTCTGCGAGCAGGCCTGACGCCCAAATACAT

CGACATCCCCGAACTGGTTGCAAACGTTAAATTCGAACCCAAACCCGCAGGCGAAC

TGCTGACGGCACCCGTTAAATCAGGCGCAGAACTGGACTTCCCCATCCCCGTTGACG

ACTTCGCATTCTCACTGCACGACCTGGCACTGCAGGAAACGTCAATCGGCCAGCACT

CAGCAGCAATCCTGTTCTGCGTTGAAGGCGAAGCAGTTCTGCGAAAAGACGAACAG

CGACTGGTTCTGAAACCCGGCGAATCAGCATTCATCGGCGCAGACGAATCACCCGTT

AACGCATCAGGCACGGGCCGACTGGCACGAGTTTACAACAAACTGTAG
```

SEQ ID NO: 27
```
ATGCAAAAACTCATTAACTCAGTGCAAAACTATGCCTGGGGAAGTAAAACTGCGTT

AACGGAACTTTATGGCATCGCCAATCCTCAGCAGCAGCCAATGGCTGAACTCTGGAT

GGGCGCGCATCCCAAAAGCTCATCGCGAATCACGACCGCCAACGGAGAGACCGTCT

CACTTAGAGATGCGATTGAGAAGAATAAAACCGCCATGCTTGGGGAGGCGGTTGCC

AATCGGTTTGGTGAGTTACCATTTCTCTTTAAAGTATTATGTGCCGCCCAGCCACTCT

CGATACAGGTGCATCCGAATAAAAGAAATAGTGAGATAGGATTTGCCAAAGAAAAC

GCAGCAGGGATACCAATGGACGCCGCAGAGCGGAATTATAAAGACCCAAATCACA

AGCCCGAGTTAGTGTTCGCCTTAACCCCATTTCTAGCCATGAACGCATTCAGAGAGT

TCAGTGATATAGTCAGCCTACTACAGCCAGTCGCTGGAGCCCATAGCGCTATCGCCC

ACTTTCTTCAGGTGCCAAACGCCGAACGGCTCAGCCAACTTTTTGCGAGTCTATTAA

ATATGCAGGGTGAGGAAAAGTCGAGGGCACTTGCCGTGCTAAAGGCAGCCCTAAAT

TCCCAGCAAGGAGAGCCATGGCAAACTATACGCGTCATATCGGAATACTATCCTGA
```

```
                                                                -continued
CGACTCCGGGCTGTTTAGTCCGCTACTACTTAACGTCGTTAAACTAAATCCGGGCGA

AGCGATGTTTTTATTTGCTGAAACCCCTCACGCCTATCTTCAGGGTGTCGCCCTCGAA

GTGATGGCTAATTCAGATAATGTCTTACGGGCCGGTCTCACACCAAAGTATATAGAC

ATCCCAGAATTAGTCGCCAACGTGAAGTTCGAACCAAAGCCGGCCGGCGAGCTCTT

GACCGCCCCAGTCAAGAGCGGTGCTGAACTAGATTTTCCAATACCAGTCGACGACTT

CGCCTTTTCCCTCCATGACCTTGCCCTTCAGGAGACCTCCATAGGACAGCATAGCGC

CGCAATACTATTCTGCGTCGAAGGAGAAGCCGTGCTCCGGAAGGATGAGCAACGGC

TTGTGTTGAAGCCAGGAGAGAGCGCATTCATAGGAGCCGATGAGAGTCCGGTTAAT

GCTTCCGGTACCGGTAGACTAGCCAGGGTGTATAACAAACTGTAG

SEQ ID NO: 28
ATGCAAAAACTCATTAACTCAGTGCAAAACTATGCCTGGGGAAGTAAAACTGCGTT

AACGGAACTTTATGGCATCGCCAATCCTCAGCAGCAGCCAATGGCTGAACTCTGGAT

GGGCGCGCATCCCAAAAGCTCATCGCGAATCACGACCGCAAACGGCGAAACGGTTT

CTCTGCGAGACGCAATCGAAAAAAACAAAACGGCAATGCTGGGCGAAGCAGTTGCA

AACCGATTCGGCGAACTGCCTTTCCTGTTCAAAGTTCTGTGCGCAGCACAGCCTCTG

TCTATCCAGGTTCACCCTAACAAACGAAACTCTGAAATCGGCTTCGCAAAAGAAAA

CGCAGCAGGCATCCCTATGGACGCAGCAGAACGAAACTACAAAGACCCTAACCACA

AACCTGAACTGGTTTTCGCACTGACGCCTTTCCTGGCAATGAACGCATTCCGAGAAT

TCTCTGACATCGTTTCTCTGCTGCAGCCTGTTGCAGGCGCACACTCTGCAATCGCAC

ACTTCCTGCAGGTTCCTAACGCAGAACGACTGTCTCAGCTGTTCGCATCTCTGCTGA

ACATGCAGGGCGAAGAAAAATCTCGAGCACTGGCAGTTCTGAAAGCAGCACTGAAC

TCTCAGCAGGGCGAACCTTGGCAGACGATCCGAGTTATCTCTGAATACTACCCTGAC

GACTCTGGCCTGYTCTCTCCTCTGCTGCTGAACGTTGTTAAACTGAACCCTGGCGAA

GCAATGTTCCTGTTCGCAGAAACGCCTCACGCATACCTGCAGGGCGTTGCACTGGAA

GTTATGGCAAACTCTGACAACGTTCTGCGAGCAGGCCTGACGCCTAAATACATCGAC

ATCCCTGAACTGGTTGCAAACGTTAAATTCGAACCTAAACCTGCAGGCGAACTGCTG

ACGGCACCTGTTAAATCTGGCGCAGAACTGGACTTCCCTATCCCTGTTGACGACTTC

GCATTCTCTCTGCACGACCTGGCACTGCAGGAAACGTCTATCGGCCAGCACTCTGCA

GCAATCCTGTTCTGCGTTGAAGGCGAAGCAGTTCTGCGAAAAGACGAACAGCGACT

GGTTCTGAAACCTGGCGAATCTGCATTCATCGGCGCAGACGAATCTCCTGTTAACGC

ATCTGGCACGGGCCGACTGGCACGAGTTTACAACAAACTGTAA

SEQ ID NO: 29
ATGCAAAAGCTAATAAATTCCGTCCAAAATTATGCCTGGGGATCCAAGACCGCCCT

AACCGAGCTATATGGAATAGCCAATCCACAACAACAACCAATGGCCGAGCTATGGA

TGGGAGCCCATCCAAAGTCCTCCTCCCGGATAACCACCGCCAATGGAGAGACCGTC

TCCCTACGGGATGCCATAGAGAAGAATAAGACCGCCATGCTAGGAGAGGCCGTCGC

CAATCGGTTTGGAGAGCTACCATTTCTATTTAAGGTCCTATGTGCCGCCCAACCACT

ATCCATACAAGTCCATCCAAATAAGCGGAATTCCGAGATAGGATTTGCCAAGGAGA

ATGCCGCCGGAATACCAATGGATGCCGCCGAGCGGAATTATAAGGATCCAAATCAT

AAGCCAGAGCTAGTCTTTGCCCTAACCCCATTTCTAGCCATGAATGCCTTTCGGGAG

TTTTCCGATATAGTCTCCCTACTACAACCAGTCGCCGGAGCCCATTCCGCCATAGCC

CATTTTCTACAAGTCCCAAATGCCGAGCGGCTATCCCAACTATTTGCCTCCCTACTA
```

-continued

```
AATATGCAAGGAGAGGAGAAGTCCCGGGCCCTAGCCGTCCTAAAGGCCGCCCTAAA

TTCCCAACAAGGAGAGCCATGGCAAACCATACGGGTCATATCCGAGTATTATCCAG

ATGATTCCGGACTATTTTCCCCACTACTACTAAATGTCGTCAAGCTAAATCCAGGAG

AGGCCATGTTTCTATTTGCCGAGACCCCACATGCCTATCTACAAGGAGTCGCCCTAG

AGGTCATGGCCAATTCCGATAATGTCCTACGGGCCGGACTAACCCCAAAGTATATA

GATATACCAGAGCTAGTCGCCAATGTCAAGTTTGAGCCAAAGCCAGCCGGAGAGCT

ACTAACCGCCCCAGTCAAGTCCGGAGCCGAGCTAGATTTTCCAATACCAGTCGATGA

TTTTGCCTTTTCCCTACATGATCTAGCCCTACAAGAGACCTCCATAGGACAACATTCC

GCCGCCATACTATTTTGTGTCGAGGGAGAGGCCGTCCTACGGAAGGATGAGCAACG

GCTAGTCCTAAAGCCAGGAGAGTCCGCCTTTATAGGAGCCGATGAGTCCCCAGTCA

ATGCCTCCGGAACCGGACGGCTAGCCCGGGTCTATAATAAGCTATAG
```

SEQ ID NO: 30
```
ATGCAAAAGCTAATAAATTCCGTCCAAAATTATGCCTGGGGATCCAAGACCGCCCT

AACCGAGCTATATGGAATAGCCAATCCACAACAACAACCAATGGCCGAGCTATGGA

TGGGAGCCCATCCAAAGTCCTCCTCCCGGATAACCACCGCCAATGGAGAGACCGTC

TCCCTACGGGATGCCATAGAGAAGAATAAGACCGCCATGCTAGGAGAGGCCGTCGC

CAATCGGTTTGGAGAGCTACCATTTCTATTTAAGGTCCTATGTGCCGCCCAACCACT

ATCCATACAAGTCCATCCAAATAAGCGGAATTCCGAGATAGGATTTGCCAAGGAGA

ATGCCGCCGGAATACCAATGGATGCCGCCGAGCGGAATTATAAGGATCCAAATCAT

AAGCCAGAGCTAGTCTTTGCCCTAACCCCATTTCTAGCCATGAATGCCTTTCGGGAG

TTTTCCGATATAGTCTCCCTACTACAACCAGTCGCCGGAGCCCATTCCGCCATAGCC

CATTTTCTACAAGTCCCAAATGCCGAGCGGCTATCCCAACTATTTGCCTCCCTACTA

AATATGCAAGGAGAGGAGAAGTCCCGGGCCCTAGCCGTCCTAAAGGCCGCCCTAAA

TTCCCAACAAGGAGAGCCATGGCAAACCATACGGGTCATATCCGAGTATTATCCAG

ATGATTCCGGACTATTTTCCCCACTACTACTAAATGTCGTCAAGCTAAATCCAGGAG

AGGCCATGTTTCTATTTGCCGAGACCCCACATGCCTATCTACAAGGAGTCGCCCTAG

AGGTCATGGCCAATTCCGATAATGTCCTACGGGCCGGACTAACCCCAAAGTATATA

GATATACCAGAGCTAGTCGCCAATGTCAAGTTTGAGCCAAAGCCAGCCGGAGAGCT

ACTAACCGCCCCAGTCAAGTCCGGAGCCGAGCTAGATTTTCCAATACCAGTCGATGA

TTTTGCCTTTTCCCTACATGATCTAGCCCTACAAGAGACCTCCATAGGACAACATTCC

GCCGCCATACTATTTTGTGTCGAGGGAGAGGCCGTCCTACGGAAGGATGAGCAACG

GCTAGTCCTAAAGCCAGGAGAGTCCGCCTTTATAGGAGCCGATGAGTCCCCAGTCA

ATGCCTCCGGAACCGGACGGCTAGCCCGGGTCTATAATAAGCTATAG
```

SEQ ID NO: 31
```
ATGCAAAAGCTAATAAATTCCGTCCAAAATTATGCCTGGGGATCCAAGACCGCCCT

AACCGAGCTATATGGAATAGCCAATCCACAACAACAACCAATGGCCGAGCTATGGA

TGGGAGCCCATCCAAAGTCCTCCTCCCGGATAACCACCGCCAATGGAGAGACCGTC

TCCCTACGGGATGCCATAGAGAAGAATAAGACCGCCATGCTAGGAGAGGCCGTCGC

CAATCGGTTTGGAGAGCTACCATTTCTATTTAAGGTCCTATGTGCCGCCCAACCACT

ATCCATACAAGTCCATCCAAATAAGCGGAATTCCGAGATAGGATTTGCCAAGGAGA

ATGCCGCCGGAATACCAATGGATGCCGCCGAGCGGAATTATAAGGATCCAAATCAT

AAGCCAGAGCTAGTCTTTGCCCTAACCCCATTTCTAGCCATGAATGCCTTTCGGGAG
```

-continued
TTTTCCGATATAGTCTCCCTACTACAACCAGTCGCCGGAGCCCATTCCGCCATAGCC

CATTTTCTACAAGTCCCAAATGCCGAGCGGCTATCCCAACTATTTGCCTCCCTACTA

AATATGCAAGGAGAGGAGAAGTCCCGGGCCCTAGCCGTCCTAAAGGCCGCCCTAAA

TTCCCAACAAGGAGAGCCATGGCAAACCATACGGGTCATATCCGAGTATTATCCAG

ATGATTCCGGACTATTTTCCCCACTACTACTAAATGTCGTCAAGCTAAATCCAGGAG

AGGCCATGTTTCTATTTGCCGAGACCCCACATGCCTATCTACAAGGAGTCGCCCTAG

AGGTCATGGCCAATTCCGATAATGTCCTACGGGCCGGACTAACCCCAAAGTATATA

GATATACCAGAGCTAGTCGCCAATGTCAAGTTTGAGCCAAAGCCAGCCGGAGAGCT

ACTAACCGCCCCAGTCAAGTCCGGAGCCGAGCTAGATTTTCCAATACCAGTCGATGA

TTTTGCCTTTTCCCTACATGATCTAGCCCTACAAGAGACCTCCATAGGACAACATTCC

GCCGCCATACTATTTTGTGTCGAGGGAGAGGCCGTCCTACGGAAGGATGAGCAACG

GCTAGTCCTAAAGCCAGGAGAGTCCGCCTTTATAGGAGCCGATGAGTCCCCAGTCA

ATGCCTCCGGAACCGGACGGCTAGCCCGGGTCTATAATAAGCTATAG

SEQ ID NO: 32
AGGTTACTTCATGCGGGTTTCTTGGTTTAATACCTCCCATTGATCTCCACATTGAAAC

AGGGCTTGATACATATG

SEQ ID NO: 33
CTCCACATTGAAACAGGGCTTGATACATATG

SEQ ID NO: 34
ATGGGCTCAATCGGCGCAGCATCAATGGAATTCTGCTTCGACGTTTTCAAAGAACTG

AAAGTTCACCACGCAAACGAAAACATCTTCTACTGCCCCATCGCAATCATGTCAGCA

CTGGCAATGGTTTACCTGGGCGCAAAAGACTCAACGCGAACGCAGATCAACAAAGT

TGTTCGATTCGACAAACTGCCCGGCTTCGGCGACTCAATCGAAGCACAGTGCGGCAC

GTCAGTTAACGTTCACTCATCACTGCGAGACATCCTGAACCAGATCACGAAACCCAA

CGACGTTTACTCATTCTCACTGGCATCACGACTGTACGCAGAAGAACGATACCCCAT

CCTGCCCGAATACCTGCAGTGCGTTAAAGAACTGTACCGAGGCGGCCTGGAACCCA

TCAACTTCCAGACGGCAGCAGACCAGGCACGAGAACTGATCAACTCATGGGTTGAA

TCACAGACGAACGGCATCATCCGAAACGTTCTGCAGCCCTCATCAGTTGACTCACAG

ACGGCAATGGTTCTGGTTAACGCAATCGTTTTCAAAGGCCTGTGGGAAAAAACGTTC

AAAGACGAAGACACGCAGGCAATGCCCTTCCGAGTTACGGAACAGGAATCAAAACC

CGTTCAGATGATGTACCAGATCGGCCTGTTCCGAGTTGCATCAATGGCATCAGAAAA

AATGAAAATCCTGGAACTGCCCTTCGCATCAGGCACGATGTCAATGCTGGTTCTGCT

GCCCGACGAAGTTTCAGGCCTGGAACAGCTGGAATCAATCATCAACTTCGAAAAAC

TGACGGAATGGACGTCATCAAACGTTATGGAAGAACGAAAAATCAAAGTTTACCTG

CCCCGAATGAAAATGGAAGAAAAATACAACCTGACGTCAGTTCTGATGGCAATGGG

CATCACGGACGTTTTCTCATCATCAGCAAACCTGTCAGGCATCTCATCAGCAGAATC

ACTGAAAATCTCACAGGCAGTTCACGCAGCACACGCAGAAATCAACGAAGCAGGCC

GAGAAGTTGTTGGCTCAGCAGAAGCAGGCGTTGACGCAGCATCAGTTTCAGAAGAA

TTCCGAGCAGACCACCCCTTCCTGTTCTGCATCAAACACATCGCAACGAACGCAGTT

CTGTTCTTCGGCCGATGCGTTTCACCC

SEQ ID NO: 35
ATGGGCAGCATTGGAGCAGCTTCCATGGAATTCTGCTTCGACGTGTTCAAAGAGCTG

AAAGTCCACCACGCTAACGAAAACATCTTCTATTGTCCGATCGCCATTATGAGCGCC

-continued
```
CTGGCAATGGTTTATCTGGGTGCCAAAGATTCTACCCGTACACAGATTAACAAAGTG

GTCCGCTTCGACAAACTGCCTGGTTTTGGTGATAGCATCGAGGCACAGTGTGGTACA

AGTGTGAACGTCCATTCTAGCCTGCGTGATATTCTGAATCAGATTACGAAACCGAAC

GACGTGTATTCCTTTTCACTGGCCAGTCGTCTGTATGCCGAAGAACGTTATCCTATTC

TGCCGGAGTATCTGCAATGCGTGAAAGAACTGTATCGTGGCGGTCTGGAACCAATC

AATTTTCAAACGGCCGCTGATCAAGCACGTGAACTGATTAACAGTTGGGTGGAAAG

TCAGACCAATGGCATTATCCGTAATGTGCTGCAGCCTAGCAGTGTTGATTCTCAGAC

GGCAATGGTCCTGGTTAACGCTATTGTGTTTAAAGGCCTGTGGGAGAAAACATTCAA

AGACGAGGATACCCAAGCAATGCCTTTCCGTGTTACCGAGCAGGAAAGCAAACCTG

TTCAGATGATGTATCAAATTGGGCTGTTCCGTGTGGCAAGCATGGCATCCGAAAAAA

TGAAAATCCTGGAGCTGCCTTTTGCTAGTGGTACAATGAGCATGCTGGTTCTGCTGC

CAGATGAAGTTTCAGGTCTGGAGCAACTGGAAAGCATCATCAACTTCGAGAAACTG

ACCGAGTGGACCTCTTCTAACGTGATGGAGGAGCGTAAAATCAAAGTCTATCTGCCT

CGTATGAAAATGGAAGAGAAATATAACCTGACCTCCGTGCTGATGGCTATGGGGAT

TACTGACGTGTTTAGCAGTAGCGCCAATCTGAGTGGGATTTCAAGCGCTGAGTCTCT

GAAAATCTCTCAGGCCGTTCATGCCGCTCATGCCGAAATCAATGAAGCCGGTCGTGA

AGTCGTGGGAAGTGCTGAAGCCGGGGTGGATGCCGCTTCTGTTAGCGAAGAATTTC

GTGCCGATCACCCGTTTCTGTTCTGTATCAAACACATTGCTACCAACGCCGTACTGTT

TTTTGGACGCTGTGTGAGCCCG
```

SEQ ID NO: 36
```
ATGGGCTCAATCGGCGCTGCTTCCATGGAATTTTGTTTTGACGTATTCAAAGAACTG

AAAGTTCACCATGCCAACGAAAACATCTTCTATTGTCCAATCGCTATCATGTCCGCC

CTGGCAATGGTATACCTGGGCGCCAAAGACTCAACAAGGACGCAAATCAATAAGGT

GGTTCGATTTGACAAGCTGCCCGGCTTCGGTGACTCGATCGAGGCGCAGTGCGGGA

CCTCAGTTAATGTTCACTCATCACTGCGCGATATTCTGAATCAGATTACGAAACCTA

ATGATGTGTACTCGTTCTCATTGGCATCTCGACTATACGCAGAAGAGCGCTATCCGA

TCTTACCCGAGTACTTGCAATGCGTGAAAGAGCTTTACCGAGGGGGCCTGGAACCG

ATCAATTTTCAGACTGCTGCCGACCAAGCTCGAGAGCTTATTAACTCTTGGGTTGAA

TCACAAACAAACGGAATCATCCGTAATGTACTGCAGCCCTCTTCAGTGGACTCACAA

ACTGCCATGGTCTTGGTAAATGCGATCGTATTTAAAGGTTTGTGGGAGAAGACTTTC

AAAGACGAAGACACACAAGCTATGCCGTTCCGAGTTACGGAACAAGAGTCAAAGCC

TGTTCAAATGATGTATCAAATCGGCTTATTCCGAGTAGCATCGATGGCAAGCGAAAA

AATGAAGATCCTGGAGCTGCCTTTCGCATCAGGGACGATGTCAATGTTGGTATTACT

CCCTGATGAAGTCTCAGGTCTGGAACAGCTGGAGTCTATTATCAACTTCGAAAAACT

GACCGAATGGACTTCATCGAATGTTATGGAAGAACGCAAATCAAGGTGTACTTGC

CCCGAATGAAGATGGAGGAAAAATATAATCTGACTAGTGTTCTGATGGCGATGGGG

ATCACAGACGTATTTTCATCGTCTGCTAATTTGAGTGGAATCTCATCGGCTGAGTCG

CTAAAGATCTCACAAGCTGTGCACGCGGCACATGCTGAGATCAACGAGGCGGGGCG

AGAAGTAGTTGGTAGTGCTGAAGCGGGGGTTGACGCAGCCTCAGTATCGGAGGAAT

TCCGTGCCGATCACCCCTTCTTATTTTGCATCAAGCACATTGCAACAAACGCCGTCTT

ATTCTTTGGGCGATGTGTTTCCCCA
```

-continued

SEQ ID NO: 37
ATGGGCTCCATCGGCGCAGCAAGCATGGAATTTTGTTTTGATGTATTCAAGGAGCTC

AAAGTCCACCATGCCAATGAGAACATCTTCTACTGCCCCATTGCCATCATGTCAGCT

CTAGCCATGGTATACCTGGGTGCAAAAGACAGCACCAGGACACAGATAAATAAGGT

TGTTCGCTTTGATAAACTTCCAGGATTCGGAGACAGTATTGAAGCTCAGTGTGGCAC

ATCTGTAAACGTTCACTCTTCACTTAGAGACATCCTCAACCAAATCACCAAACCAAA

TGATGTTTATTCGTTCAGCCTTGCCAGTAGACTTTATGCTGAAGAGAGATACCCAAT

CCTGCCAGAATACTTGCAGTGTGTGAAGGAACTGTATAGAGGAGGCTTGGAACCTA

TCAACTTTCAAACAGCTGCAGATCAAGCCAGAGAGCTCATCAATTCCTGGGTAGAA

AGTCAGACAAATGGAATTATCAGAAATGTCCTTCAGCCAAGCTCCGTGGATTCTCAA

ACTGCAATGGTTCTGGTTAATGCCATTGTCTTCAAAGGACTGTGGGAGAAAACATTT

AAGGATGAAGACACACAAGCAATGCCTTTCAGAGTGACTGAGCAAGAAAGCAAAC

CTGTGCAGATGATGTACCAGATTGGTTTATTTAGAGTGGCATCAATGGCTTCTGAGA

AAATGAAGATCCTGGAGCTTCCATTTGCCAGTGGGACAATGAGCATGTTGGTGCTGT

TGCCTGATGAAGTCTCAGGCCTTGAGCAGCTTGAGAGTATAATCAACTTTGAAAAAC

TGACTGAATGGACCAGTTCTAATGTTATGGAAGAGAGGAAGATCAAAGTGTACTTA

CCTCGCATGAAGATGGAGGAAAAATACAACCTCACATCTGTCTTAATGGCTATGGG

CATTACTGACGTGTTTAGCTCTTCAGCCAATCTGTCTGGCATCTCCTCAGCAGAGAG

CCTGAAGATATCTCAAGCTGTCCATGCAGCACATGCAGAAATCAATGAAGCAGGCA

GAGAGGTGGTAGGGTCAGCAGAGGCTGGAGTGGATGCTGCAAGCGTCTCTGAAGAA

TTTAGGGCTGACCATCCATTCCTCTTCTGTATCAAGCACATCGCAACCAACGCCGTT

CTCTTCTTTGGCAGATGTGTTTCCCCT

SEQ ID NO: 38
ATGGGAAGCATAGGCGCAGCTTCCATGGAATTTTGCTTCGACGTATTTAAGGAGCTA

AAGGTCCATCATGCCAATGAGAATATATTTTATTGTCCAATAGCCATAATGTCCGCC

CTAGCCATGGTCTATCTAGGAGCCAAGGATTCCACCCGGACCCAAATAAATAAGGT

CGTCCGGTTTGATAAGCTACCAGGATTTGGAGATTCCATAGAGGCCCAATGTGGAAC

CTCCGTCAATGTCCATTCCTCCCTACGGGATATACTAAATCAAATAACCAAGCCAAA

TGATGTCTATTCCTTTTCCCTAGCCTCCCGGCTATATGCCGAGGAGCGGTATCCAATA

CTACCAGAGTATCTACAATGTGTCAAGGAGCTATATCGGGGAGGACTAGAGCCAAT

AAATTTTCAAACCGCCGCCGATCAAGCCCGGGAGCTAATAAATTCCTGGGTCGAGTC

CCAAACCAATGGAATAATACGGAATGTCCTACAACCATCCTCCGTCGATTCCCAAAC

CGCCATGGTCCTAGTCAATGCCATAGTCTTTAAGGGACTATGGGAGAAGACCTTTAA

GGATGAGGATACCCAAGCCATGCCATTTCGGGTCACCGAGCAAGAGTCCAAGCCAG

TCCAAATGATGTATCAAATAGGACTATTTCGGGTCGCCTCCATGGCCTCCGAGAAGA

TGAAGATACTAGAGCTACCATTTGCCTCCGGAACCATGTCCATGCTAGTCCTACTAC

CAGATGAGGTCTCCGGACTAGAGCAACTAGAGTCCATAATAAATTTTGAGAAGCTA

ACCGAGTGGACCTCCTCCAATGTCATGGAGGAGCGGAAGATAAAGGTCTATCTACC

ACGGATGAAGATGGAGGAGAAGTATAATCTAACCTCCGTCCTAATGGCCATGGGAA

TAACCGATGTCTTTTCCTCCTCCGCCAATCTATCCGGAATATCCTCCGCCGAGTCCCT

AAAGATATCCCAAGCCGTCCATGCCGCCCATGCCGAGATAAATGAGGCCGGACGGG

AGGTCGTCGGATCCGCCGAGGCCGGAGTCGATGCCGCCTCCGTCTCCGAGGAGTTTC

-continued
GGGCCGATCATCCATTTCTATTTTGTATAAAGCATATAGCCACCAATGCCGTCCTATT

TTTTGGACGGTGTGTCTCCCCA

Wildtype (wt) manA was amplified from genomic DNA of strain SL7207 using oligos oJT7 and oJT8, subcloned and subsequently sequenced. manA-expression plasmids pJT6-pJT9, pJT27-29 and pJT36-39 contain variants of manA (wt manA, manA 1-10) under control of its own promoter (69 bp upstream of the start ATG) in the background of plasmid pETcocol (Novagen).

These plasmids were generated by insertion of manA/promoter fragments into plasmid pETcoco-1 via HpaI and SwaI restriction sites. pETcocoΔ is a religation product of the empty vector fragment lacking lacI of the original plasmid. Ova-expression plasmids pJT20-23 contain variants of the hen egg ovalbumin encoding ova under control of the constitutive E. coli β-lacamase promoter in a low copy plasmid background maintained at approximately 15 copies per cell.

Wildtype ova was originally amplified with primers from plasmid pOV230 (30) then sequenced and subcloned into plasmid pHL49 (29) yielding plasmid pLK2. From this plasmid wt-ova was replaced by codon-adapted variant genes (oval-4, S16) via flanking NdeI and HindIII restriction sites. pETcoco-1 and pHL49 derived plasmids harbor cam encoding the chloramphenicol resistance gene.

3.4 Bacterial Growth

E. coli and S. Typhimurium were routinely grown in liquid LB medium or on LB agar plates. Derivatives of strain SL7207 ΔaraBADΔmanA (SL-361) were also grown in M9 minimal medium (MM) supplemented with so called aro-supplements (40 µg ml-1 mannose 40 µg ml-1 phenylalanine, 40 µg ml-1 tryptophane, 40 µg ml-1 tyrosine, 10 µg ml-1 4-aminobenzoic acid, 10 µg ml-1 2,3-dihydroxybenzoate), 200 mg ml-1 mannose and/or 200 mg ml-1 glucose. Other supplements were added to media when appropriate, such as 100 µg ml-1 ampicillin, 30 µg ml-1 streptomycin, 20 µg ml-1 chloramphenicol or 2 mg ml-1 L-arabinose. LB medium base and supplements were purchased from Carl Roth, MM base from Sigma-Aldrich. Bacterial growth was monitored in 200 µl cultures at 37° C. and agitation at 700 rpm in a Thermostar microplate incubator (BMG LabTech). 25 ml flask cultures were grown in at 37° C. and agitation at 200 rpm Innova 42R incubator (New Brunswick). Optical density was measured at 600 nm (OD600 nm) and the number of colony forming units (cfu) was determined by plating serial dilutions of bacterial cultures on LB-agar plates.

3.5 λ-Red Recombinase-Mediated Gene Deletion

λ-Red recombinase-mediated depletion of manA from strain SL7207ΔaraBAD was carried out as previously described (7, 35). Briefly, a PCR product harbouring≈40 bp end sequences homologous to manA and a kanamycin resistance marker was amplified with pKD4 as template and primers oJT1 and oJT2. This product was transformed into strain SL7207ΔaraBAD harbouring the λ-Red recombinase expression plasmid pKD46, and subsequently clones were selected on media plates containing kanamycin and streptomycin. A clone lacking manA (SL7207ΔaraBADΔmanA) was identified by colony PCR with primers oJT4 and oHL20.

3.6 Soluble protein extracts

Bacteria were cultured op to an $OD_{600}$≈1 in supplemented MM. $4 \times 10^9$ bacteria were harvested at $5 \times 10^3 \times g$ for 5 min. Pellets were washed once, centrifuged again and then resuspended in 460 ml ice-cold water. The suspension was transferred into glass bead containing tubes (VK01, Precellys) and those were then placed into a Precellys24 homogenizer for bacterial lysis at 6500 rpm for 20 s with three repetitions. Lysates were centrifuged at 12 000×g for 5 min in a cooled centrifuge and supernatants were stored at −70° C. until further analysis.

3.7 Immunoblot

Bacterial lysates were separated with NuPAGE 4% to 12% Bis-Tris gels in an XCell Sure-Lock electrophoresis chamber according to manufacturer's instructions (ThermoFisher). Samples were prepared using 4× NuPAGE LDS sample buffer and 10× NUPAGE reducing agent (ThermoFisher). Page Ruler Plus Marker (ThermoFisher) was used for molecular weight determination of proteins and Roti-Blue reagent (Carl Roth) for unspecific staining of protein bands in gels. Proteins were immobilized on a nitrocellulose membrane (Protan BA79, VWR) using a Semi-Dry-Blotter device (Preqlab). Specific bands were revealed with polyclonal rabbit sera raised against Ova (Acris, R1101) or ManA (MyBioSource, MBS1491170) and subsequent binding of an horseradish peroxidase conjugated antibody (GE, NA934). Roti-Lumin plus spray (Carl Roth) was applied to the membrane and chemoluminescent signals were detected with the Microchemi imager (Biostep).

Further analysis was performed with ImageJ. Generally, the gel-images offering the highest contrast below saturation were chosen from images with different exposure times. We used two methods giving identical results, first using a rectangular region of interest (ROI) and measuring median grey intensity for every band, then subtracting the background median grey intensity of every gel and second with the method outlined in (16).

3.8 Quantification of ManA Expression in S. Typhimurium Lysates

Mannose-6-phosphate isomerase (ManA) levels were determined by multiple reaction monitoring (MRM). A ManA specific peptide (YDIPELVANVK) was selected using UniProt P25081 as a template and ordered as stable isotope labelled calibration peptide (SpikeTide TQL, JPT, Berlin, Germany). This peptide carries a TAG for quantification that requires trypsin cleavage before MRM analysis. A 1 nmol aliquot of the peptide was reconstituted in 100 µl of 0.1 NH4HCO3 containing 50% ACN and stored at 80° C. before usage. Calibration values were obtained by spiking the calibration peptide into 13.53 µl of a ManA deficient S. Typhimurium lysate (sample 393). DTT (9.45 µl, c=1.83 µg ml-1) was added for reduction of disulfide bonds (15 min at 25° C.). Enzymatic digestion (16 h at 37° C.) was done by adding trypsin (5.05 µl, c=816 ng) and stopped by adding formic acid (5.86 µl, 5%) in water. Final concentrations of the calibration peptide can be found in Table S13.

TABLE S13

| MRM Transitions and collision energy. | | | | |
|---|---|---|---|---|
| Transition | MS1 | MS2 | F | CE |
| qualifier | 687.82 | 643.42 | y6 | 29 |
| quantifier | 687.82 | 869.50 | y8 | 20 |
| qualifier | 687.82 | 982.60 | y9 | 20 |

TABLE S13-continued

MRM Transitions and collision energy.

| Transition | MS1 | MS2 | F | CE |
|---|---|---|---|---|
| qualifier | 687.82 | 1097.60 | y10 | 20 |
| qualifier* | 691.39 | 651.43 | y6 | 29 |
| quantifier* | 691.39 | 877.52 | y8 | 20 |
| qualifier* | 691.39 | 990.61 | y9 | 20 |
| qualifier* | 691.39 | 1105.63 | y10 | 20 |

F: Fragment,
CE: Collision Energy,
*isotopically labelled.

Calibration samples were digested in triplicates, each replicate was injected once at a volume of 20 µl. A volume of 13.53 µl of ManA containing samples (see Table S14) were combined with 2.4 µl calibration peptide, 12.34 µl NH4HCO3 (50 mmol), 9.54 µl DTT, 11.27 µl iodoacetamide, 5.05 µl. Time and temperature values for reduction, alkylation and digestion were set as described above. All samples and calibration standards were frozen at −80° C. once before usage. Each sample was digested in triplicates and each triplicate was injected three times at a volume of 20 µl.

TABLE S14

Final concentrations of the calibration peptide.

| calibration peptide | peptide concentration [µl] | concentration of 50 mmolNH$_4$HCO$_3$ [µl] |
|---|---|---|
| 25 | 0.151 | 14.59 |
| 100 | 0.6 | 14.14 |
| 200 | 1.2 | 13.45 |
| 400 | 2.4 | 12.34 |
| 1000 | 6 | 8.74 |
| 2000 | 12 | 2.74 |

For MRM analysis 20 µl of each sample were injected in an ACQUITY-UPLC equipped with an ACQUITY UPLC Peptide BEH C18 column (130 Å, 1.7 µmol, 2.1 mm×100 mm) and an ACQUITY UPLC BEH C18 VanGuard Precolumn (130 Å, 1.7 µmol, 2.1 mm×5 mm) (Waters, Milford, US). A binary solvent system consisting of an aqueous mo-bile phase (solvent A: water with 0.1% (v/v) formic acid) and an organic mobile phase (solvent B: acetonitrile with 0.1% formic acid) was used for the chromatographics separation. All solvents for LC-MS analysis was purchased at Biosolve (Valkenswaard, NL) unless otherwise noted. The elution gradient was 0.5 min, 3% solvent B, 3% to 40% solvent B in 9.5 min, 1 min 40% solvent B, 40% to 90% solvent B in 0.5 min with a constant flow rate of 300 µl min$^{-1}$ and 1.2 min 90% solvent B, 90% to 3% solvent B in 2.3 min with a flow rate of 500 µl min$^{-1}$.

The triple quadrupole mass spectrometer (Xevo TQ-S, Waters) was operated using MRM in positive ionization mode and scanning for 4 specific transitions of the doubly charged natural peptide YIDIPELVANVK (MH$^{2+}$ m/z=687.82) and the isotopically labelled standard YIDIPELVANVK* (MH$^{2+}$ m/z=691.39) with the following optimal acquisition parameters: capillary voltage (2.5 kV), cone voltage (21 V), desolvation temperature (200° C.), desolvation gas (800 l h$^{-1}$), cone gas (150 l h$^{-1}$). The dwell time was set to auto and the optimized collision energy for each transition is shown in Table S13.

Data analysis was done using the TargetLynx software (V4.1 SCN810, Waters). The raw data was smoothed before integration with the mean method with width of 2 and 2 iterations. The automatic noise measurement was activated and the peak detection was done with the following values for baseline detection and peak separation: 10 (Balance), 10 (Splitting), 10 (Reduce Tailing), 0.2 (Reduce Height). The quantification was done using the peak area of the transition 687.82→869.50 or 691.39→877.52 respectively.

To calculate relative protein abundance, we calculated the peak area of the unlabeled peptide. For the different dilution-repetitions done on different days we used the ratio of unlabeled to labelled peptide as a correction factor and calculated the weighted average of all dilutions.

3.8 qPCR qPCR for quantification of manA transcripts was performed. First, mRNA was reverse transcribed to cDNA. Appropriate primers were designed for each manA variant and cam. The product sizes were in a range of 88 to 136 bp S15. Bacteria were cultured in supplemented MM up to an OD600≈1 and 2×10$^8$ bacteria were harvested at 5×10$^3$×g for 5 min. RNAprotect Bacteria Reagent and RNeasy Plus Mini Kit were used for purification of RNA (Qiagen). 380 ng RNA of each sample was used for cDNA synthesis employing SuperScript III Reverse Transcriptase (ThermoFisher). qPCR reactions were set up using the iTaq Universal SYBR Green Supermix (Bio-Rad) and were run on a CFX96 thermal cycler (Bio-Rad). Raw-data were analyzed using the CFX Manager Software (Bio-Rad) and Cq values calculated by thresholding.

For relative quantification of manA transcripts primer efficiencies were measured by using a dilution series of all manA transcripts and cam and additionally via sigmoidal curve fitting in R.

3.9 Software Implementation

Two versions of the simulation software were implemented: a Java GUI application OCTOPOS (Optimized Codon Translation fOr PrOtein Synthesis) for easy optimization of sequences and a C application for fast generation of phase diagrams. Both can be accessed online.

II. Results

Although the genetic code is redundant with up to six synonymous codons encoding one amino acid, codon choice affects both cellular protein levels as well the fitness of whole organisms as studied in bacteria (e.g. *Escherichia coli* or *Salmonella enterica* serovar Typhimurium, eukaryotic micro-organisms such as *Saccharomyces cerevisiae* as well as in human cell lines such as HepG2 or HEK293 (21, 23, 27, 32). There are marked differences in codon choice between organisms, which makes adequate codon adaptation to the target organism generally mandatory for artificially transferred genes. As differences in codon choice are particularly pronounced in highly expressed genes. It is therefore generally assumed that codon choice—or codon bias—in highly expressed genes is under selection pressure and in this way "optimal" (13). Therefore, optimal codon choice for an organism is largely determined through imitation of codon choice in the organism's highly expressed genes. The most prominent measure of codon optimality or adaptation to an organisms highly expressed genes is the codon adaptation index (CAI)(41) being accompanied by a plethora of related indices (32). These indices are valuable measures of "codon optimality" as adaptation of codon choice to that of highly expressed genes often correlates with increased levels of protein expression as well as an overall increase in an organisms fitness which may become evident through increased growth rates (10). This finding is key to many biotechnological applications and in particular to artificial gene transfer which will generally not result in sufficient protein yield if the codon usage of transferred genes were not adapted to that of the target organisms (highly expressed genes). Algorithmically, this is implemented in a variety of commonly used software tools (such as e.g. GeneDesigner (60), JCat (19), Optimizer (33), Synthetic Gene Designer (58), Codon Optimization OnLine (COOL) (5), UpGene (15), EuGene (15).

Although this is the current state of the art, there is a serious drawback of this method: As codon adaptation to highly expressed genes is a purely heuristic measure it does not provide a deeper understanding of the underlying processes and does not answer the question what determines optimality in a context dependent and mechanistic fashion. As a consequence this heuristic codon optimization repeatedly causes unexpected or suboptimal outcomes (56, 59). While some approach this dilemma through a search for further covariates such as length of genes (13, 17), GC3 content or mRNA secondary structure, (3, 21, 51, 57), we address the question how codon bias affects protein translation through a codon-specific elongation model (COSEM). As the model of the present invention makes use of the understanding of protein synthesis it naturally opens a new avenue to overcome these limitations of the heuristic approach.

There are several mechanistic models which study the translation dynamics of proteins by following the ribosome dynamics on the mRNA (6, 34, 49, 61, 62) being variants of a class of models referred to as Totally Asymmetric Exclusion Process (TASEP) (53)): after attachment of ribosomes to mRNA (initiation step), the ribosomes can only move forward to successively translate codons into amino acids (elongation step, totally asymmetric) while multiple ribosomes can not overtake one another (spatially exclusive). The codon-specific elongation model (COSEM) combines a deep understanding of dynamic features extensively studied in TASEPs with significant improvements in biological realism.

The present invention, inter alia, refines earlier parameter sets (14) to parameterize our model with biologically plausible translation-initiation rates, codon specific elongation rates and accuracies, as well as ribosome drop-off rates (1, 4, 10, 36, 37, 40). These parameters are based on concentrations of cognate and near-cognate tRNAs, elongation factors and ribosome sizes and are as such specific for the organism in which the protein is to be expressed.

This integration of well studied TASEPs models with biologically relevant parameter sets allows for a determination of the impact of codon choice on protein levels and translation accuracy in a mechanistic manner both at initiation and elongation steps.

The codon-specific elongation model (COSEM) further facilitates thought experiments which can frame translation dynamics within a more general dynamic picture for example to explain ribosome dynamics (2). This approach of the present invention is used for the first time to optimize genes in a context dependent manner for accuracy, protein output in addition to further sequence features. As shown in detail further below, the predictions of protein abundance are evaluated on large scale data sets for *E. coli, S. cerevisiae* and human cell lines HEK293 showing improved predictive power. In addition, two genes have been chosen, manA and ova, for a more detailed analysis and for which variants were designed for expression in S. Typhimurium and comparison of experimentally measured protein expression with theoretical predictions.

1. The Codon-Specific Elongation Model—Dynamic Regimes and Biological Implementation Before exploring the dynamics of the codon-specific elongation model (COSEM) and its applications in codon optimization its ingredients as sketched in FIG. 6 have to be introduced: The translation process is initiated through ribosome attachment at a rate $\alpha$. Attached ribosomes elongate at rates $\omega i,elo$ (or $\omega i$ for short) with accuracies $\alpha i$ (accuracy entails the insertion of a near-cognate as well as non-cognate regardless if the replacement is the intended amino acid or not) specific for the codon found at position i in the sequence. Codon specific rates and accuracies have been derived for each model organism on the basis of ternary complex formation. These take the concentrations of charged tRNA (aa-tRNA), elongation factors and GTP molecules into account (36, 37) and are summarized in Tables S1-S12. Ribosomes cannot overtake each other but can drop off the mRNA at a rate 7 and terminate translation at a rate $\beta$, typically the elongation rate of the last codon in the sequence $\omega_{final}$. In addition to classical TASEPs, the codon-specific elongation model further considers that ribosomes cover several codons at a time (ribosomal footprint d=10).

Figure 7:
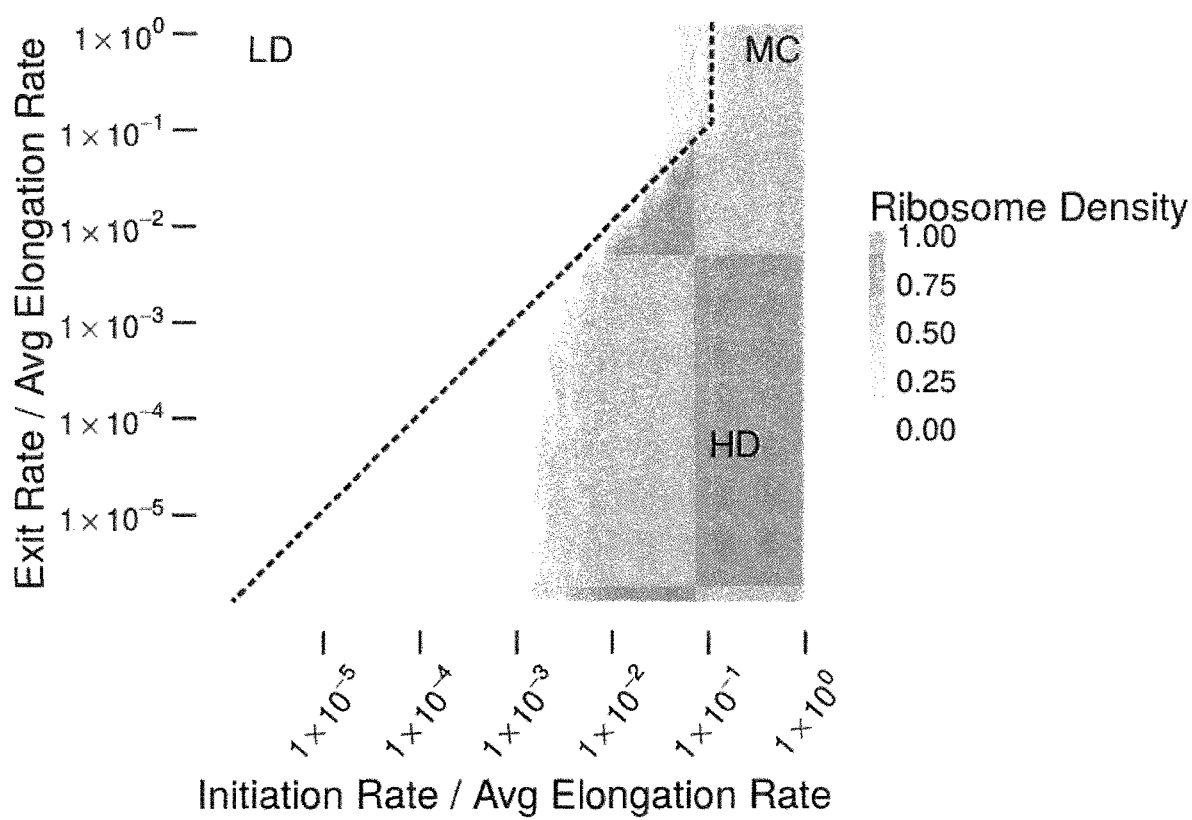
FIG. 7: Dynamic regimes of protein translation. Ribosome density as a function of the elongation rate of the last codon (translation termination rate $\beta$ and initiation rate $\alpha$ normalized by the average elongation rate 60 s$^{-1}$.

FIG. 7 shows the dynamic regimes of the codon-specific elongation model (COSEM) in analogy to the well studied TASEPs (8, 39). As a model sequence, a chain of 300 CTGs with an elongation rate $\omega \approx 60$ s$^{-1}$ was used. The exact values were chosen since the median length of *E. coli* genes is 300 and CTG is the most commonly occurring codon. After equilibration, the model shows distinct dynamic regimes depending on the translation initiation rate $\alpha$ as well as the termination rate $\beta$ relative to the elongation rate ($\omega$)=60 s$^{-1}$ seen in the model sequence. The low ribosome density phase (LD) corresponds to a system in which the rate of ribosome attachment (initiation at rate $\alpha$) is lower than the rate of translation termination (termination at rate $\beta=\omega_{final}$) or similarly in the presence of bottlenecks with slow codons. Low ribosome density goes along with little collective dynamics such as jamming but also low rates of protein translation per time to which we equally refer as COSEM current. The opposite situation arises when the dynamics is limited through low rates of translation termination or bottlenecks of slow codons. The high ribosome density phase (HD) is characterized by ribosome jamming and in consequence inefficient use of ribosomes. As soon as translation initiation and termination rates grow beyond a critical value, the dynamics reaches the maximal current phase (MC) which is characterized by most efficient protein translation (COSEM current). While the phase diagram in FIG. 7 is based on constant elongation rates, The influence of local inhomogeneity mostly causes a small shift of the transition lines (42). (The coefficients of variation among codon-specific elongation rates in the studied gene sets from *E. coli, S. cerevisiae*, HepG2, and HEK293 are 81%, 170%, 52% and 52% respectively. A more pronounced effect on the phase diagram was found when including drop-off kinetics in connection with local inhomogeneities which can cause bottleneck-induced mixed phases (31).

1.1 Predicting Protein Expression

The codon-specific elongation model is designed to make predictions on protein translation per time in terms of COSEM current which can be expected to be the most relevant predictor for protein expression (34, 43). For further improvement, this predictor was integrated within a protein expression score or full model that assesses the relative influence of factors that are known or expected to impact on protein expression. While mRNA transcript abundance is considered in the protein expression score as an obvious prerequisite for protein expression, further features are incorporated in the score as they are known to influence the structure and stability of the mRNA transcript and therefore may impact on protein expression. These include mRNA folding energy in the first 30 codons at the 5'-end (20, 47), overall GC content measured as the fraction of guanine and cytosine in the third codon positions (GC3 content) and the number of hairpins at the 5'-end, again for the first 30 codons (20). The protein expression score may further consider the prevalence of AGG codons among the first 30 codons, the number of out-of-frame stop-codons and other motifs to avoid within the whole sequence which may include CpG content and organism-specific binding sites for restriction enzymes. The average elongation rate in the first 30 to 50 codons (acknowledging the ramp hypothesis of (49)), a bottleneck index (the slowest elongation rate of a 10 codon sliding window) (11) as well as the accuracy of translation, i.e. the probability with which instead of cognate tRNA a near-cognate or non-cognate tRNA is incorporated, are further taken into account as measures influencing efficient translation and functional proteins including their folding.

For the calculation of the COSEM current, codon specific elongation rates were derived for prokaryotic $E.$ $coli$, eukaryotic $S.$ $cerevisiae$ and human cell lines HEK293 and HepG2 following the procedures in Rudorf et. al. (36, 37) (see Materials and Methods, section on Codon-specific elongation rates and accuracies).

Aside from the COSEM current, translation accuracy can be expected to be of similar relevance for protein expression. Incorrectly inserted amino acids can affect the folding and functionality of a protein and in consequence can effectively reduce protein production. Surprisingly, it can be shown that—aside from few exceptions as shown in FIGS. 15 to 17—faster codons are also more accurate codons. This is due to the fact that both translation errors and delays largely result from the competition between cognate, near- and non-cognate tRNAs, i.e. arise from similar sources (36, 37). Still, translation accuracy is considered as an additional factor in the scoring function which particularly allows us to study the translation of proteins for which accuracy is especially relevant.

To assess the relative importance of the above factors the protein expression score was fit and cross-validated to protein abundance seen in $E.$ $coli$, $S.$ $cerevisiae$ and HEK293 by using available data on protein and transcript abundance (55) with a boosted general additive model (25) (for details see FIGS. 11 to 13).

FIG. 8 shows protein abundances predicted by our protein expression score in comparison with measured protein abundances in $E.$ $coli$, $S.$ $cerevisiae$ and HEK293 by using protein and transcript abundance data from the PaxDb database (55). The coefficient of determination $R^2$ is evaluated to assess the proportion of variance in protein abundances that can be explained by the protein expression score. As demonstrated in FIG. 8 45% 51% and 38% of variation in protein expression in $E.$ $coli$, $S.$ $cerevisiae$ and HEK293, respectively, can be explained by our protein expression score. This corresponds to improved correlation coefficients R 0.67, 0.71 and 0.62 as compared to 0.29, 0.66 and 0.67 obtained by (45) on a similar but not identical data set.

1.2 Optimizing Protein Translation

FIG. 8 shows the predictive power of the codon expression score which allows to address the inverse problem, i.e., to optimize coding sequences. Different from earlier optimization procedures a gene was not expected to be optimal if its codons are similar to those used in a reference gene set but optimality is measured through the protein expression score which is based on a mechanistic model. This naturally allows for an optimization of protein expression but widens the scope for optimization of alternative features through different weighting of the base functions in the protein expression score. In this way a sequence can also be optimized for translation accuracy which might be more relevant for certain applications or deoptimized by minimizing the protein expression score.

While FIG. 8 shows an extensive validation of the model of the present invention with an in depth study of selected genes has been proceeded as outlined in the following. The first model gene ova encodes Ovalbumin (Ova), the main constituent of egg white which represents an important food allergen and is often used as model allergen in biomedical research. Sufficient expression of ova after artificial transfer of the gene into host organisms such as $E.$ $coli$ or S. Typhimurium is therefore relevant in biotechnological as well as medical applications. However, variants in which codon usage was adapted with standard procedures did not lead to an increased protein expression over the wild type variant.

The second model gene manA encodes for phosphomannose isomerase which is essential for the mannose metabolism in S. Typhimurium. It catalyses the conversion of fructose-6-phosphate and mannoso-6-phosphate and is necessary for growth if S. Typhimurium are to grown on medium with mannose as sole carbon source (46). Furthermore, when used to infect mice in vivo a ΔmanA mutant shows a significant reduction in infectivity (46). In spite of its key role for the S. Typhimurium metabolism and expression levels manA shows a comparably low codon adaptation index of 0.58 As such it is an interesting gene to study whether a large codon adaptation index is an indicator for optimal codon usage in this setting or whether other selection criteria might be more relevant (59).

For both genes, variants have been created that are optimized for COSEM current and accuracy, a variant that has been de-optimized on the basis of the present model with respect to protein expression as well as a variant for which we expected intermediate protein expression. For comparison sequence variants have been optimized by GeneOptimizer (GeneArt) with standard parameters. For manA also variants have been created with the original ramp of slow codons in the first 50 codons as this turned out to be one of the major determinants of expression strength for manA. Additionally a variant has been synthesized with slow codons between manA secondary structures. A complete overview of sequences can be found in the above Table S16.

FIG. 9A/B show the protein expression in S. Typhimurium of the synthetic ova and manA sequences relative to the wild type sequences in comparison to respective relative protein expression scores. FIG. 9A shows the wild type with four designed variants of ova: the de-optimized variant comes with the expected large decrease in expression, the optimized variant shows an 3-4-fold increase in expression compared to the wildtype. The synthetic version designed with the help of GeneOptimizer (GeneArt) shows a slightly lower level of protein expression than the wild type, whereas an additional, intermediate variant shows the same expression as the wild type.

As shown in FIG. 9B, the relative protein expression score for manA variants reflects measured protein levels well for the de-optimized, wild type and intermediate variants as well as those optimized by Geneart (including those with an additional ramp of slow codons and slow codons between protein secondary structures). Choosing fast and accurate codons throughout the whole sequence leads to no increase protein expression (synthetic sequences Accuracy and Speed). However, a marked increase in protein expression can be achieved by combining our optimization scheme while preserving the ramp of slow codons within the first 50 codons in the manA sequence. This highlights the relevance of a ramp of slow codons that is seen in the beginning of certain genes and the need to preserve this feature in optimized sequences of these genes. Remarkably, measurements of S. Typhimurium growth rates on minimal manose medium showed that manA protein expression (or optimality) correlates with bacterial growth rate (cf. FIG. 14).

Overall, the present approach is able to propose synthetic sequences with protein expression levels beyond those seen in sequences suggested by alternative state-of-the-art techniques. As a benefit over earlier approaches, the present optimization scheme does not only propose optimal sequences but is also informative about protein expression levels through the protein expression score as shown in FIGS. 8 and 9A/B.

1.3 Summary

The above data demonstrate that the integration of the COSEM with further covariates into a protein expression score leads to improved predictions on protein expression if adequately parameterized as exemplified for E. coli, S. cerevisiae and human cell lines HEK293. This paves the way for a new strategy of codon optimization for which it has been shown superiority in two exemplary genes, manA and ova, expressed in S. Typhimurium. A major advantage over heuristic approaches is that the present optimization scheme is based on a deeper understanding of protein translation and as such allows for an optimization of specific features such as translation accuracy or protein expression. Contrarily, a sequence can equally be deoptimized (for specific features) through a minimization of the (adequately weighted) protein expression score which is valuable for the engineering of attenuated pathogens. The modularity and parameterization of the protein expression score further allows for an adaptation to other target systems. The present approach can also be integrated into larger workflows that might include further aspects of sequence optimization such as ribosomal binding site optimization.

REFERENCES

[1] B. Aguirre, M. Costas, N. Cabrera, G. Mendoza-Hernndez, D. L. Helseth, P. Fern-ndez, M. T. de Gmez-Puyou, R. Prez-Montfort, A. Torres-Larios, and A. G. Puyou. A ribosomal misincorporation of lys for arg in human triosephosphate isomerase expressed in Escherichia coli gives rise to two protein populations. PLoS One, 6(6): e21035, 2011.

[2] Yoav Arava, Yulei Wang, John D. Storey, Chih Long Liu, Patrick O. Brown, and Daniel Herschlag. Genome-wide analysis of mrna translation profiles in Saccharomyces cerevisiae. Proc Natl Acad Sci USA, 100(7):3889-3894, April 2003. doi: 10.1073/pnas.0635171100.

[3] Grégory Boël, Reka Letso, Helen Neely, W Nicholson Price, Kam-Ho Wong, Min Su, Jon D. Luff, Mayank Valecha, John K. Everett, Thomas B. Acton, Rong Xiao, Gaetano T. Montelione, Daniel P. Aalberts, and John F. Hunt. Codon influence on protein expression in E. coli correlates with mrna levels. Nature, 529(7586):358-363, January 2016. doi: 10.1038/nature16509.

[4] T. L. Calderone, R. D. Stevens, and T. G. Oas. High-level misincorporation of lysine for arginine at aga codons in a fusion protein expressed in Escherichia coli. J. Mol. Biol., 262(4):407-412, 1996.

[5] Ju Xin Chin, Bevan Kai-Sheng Chung, and Dong-Yup Lee. Codon optimization online (cool): a web-based multi-objective optimization platform for synthetic gene design. Bioinformatics, 30(15):2210-2212, August 2014. doi: 10.1093/bioinformatics/btu192.

[6] Dominique Chu, James Thompson, and Tobias von der Haar. Charting the dynamics of translation. Biosystems, 119:1-9, May 2014. doi: 10.1016/j.biosystems.2014.02.005.

[7] Kirill A Datsenko and Barry L Wanner. One-step inactivation of chromosomal genes in Escherichia coli k-12 using per products. Proceedings of the National Academy of Sciences, 97(12):6640-6645, 2000.

[8] Bernard Derrida, M R Evans, Vincent Hakim, and Vincent Pasquier. Exact solution of a 1d asymmetric exclusion model using a matrix formulation. Journal of Physics A: Mathematical and General, 26(7): 1493, 1993.

[9] H. Dong, L. Nilsson, and C. G. Kurland. Gratuitous overexpression of genes in Escherichia coli leads to growth inhibition and ribosome destruction. J. Bacteriol., 177(6):1497-1504, 1995.

[10] H. Dong, L. Nilsson, and C. G. Kurland. Co-variation of trna abundance and codon usage in Escherichia coli at different growth rates. J. Mol. Biol., 260(5):649-663, 1996.

[11] JiaJia Dong, Beate Schmittmann, and Royce K P Zia. Inhomogeneous exclusion processes with extended objects: The effect of defect locations. Physical Review E, 76(5):051113, 2007.

[12] D. A. Drummond and C. O. Wilke. Mistranslation-induced protein misfolding as a dominant constraint on coding-sequence evolution. Cell, 134(2):341-352, 2008.

[13] Laurent Duret and Dominique Mouchiroud. Expression pattern and, surprisingly, gene length shape codon usage in Caenorhabditis, Drosophila, and Arabidopsis. Proceedings of the National Academy of Sciences, 96(8): 4482-4487, 1999.

[14] A. Fluitt, E. Pienaar, and H. Viljoen. Ribosome kinetics and aa-trna competition determine rate and fidelity of peptide synthesis. Comput. Biol. Chem., 31(5):335-346, 2007.

[15] Paulo Gaspar, José Luís Oliveira, Jörg Frommlet, Manuel A S. Santos, and Gabriela Moura. Eugene: maximizing synthetic gene design for heterologous expression. Bioinformatics, 28(20):2683-2684, October 2012. doi: 10.1093/bioinformatics/bts465.

[16] Max Gassmann, Beat Grenacher, Bianca Rohde, and Johannes Vogel. Quantifying western blots: pitfalls of densitometry. Electrophoresis, 30(11): 1845-1855, 2009.

[17] Manolo Gouy and Christian Gautier. Codon usage in bacteria: correlation with gene expressivity. Nucleic Acids Res., 10(22):7055-7074, 1982.

[18] Kirill B Gromadski and Marina V Rodnina. Kinetic determinants of high-fidelity trna discrimination on the ribosome. Mol. Cell, 13(2):191-200, 2004.

[19] Andreas Grote, Karsten Hiller, Maurice Scheer, Richard Mnch, Bernd Nrtemann, Dietmar C Hempel, and Dieter Jahn. Jcat: a novel tool to adapt codon usage of a target gene to its potential expression host. Nucleic acids research, 33(suppl 2): W526-W531, 2005.

[20] Wanjun Gu, Tong Zhou, and Claus O. Wilke. A universal trend of reduced mrna stability near the translation-initiation site in prokaryotes and eukaryotes. PLoS Comput Biol, 6(2):e1000664, February 2010.

[21] Claes Gustafsson, Sridhar Govindarajan, and Jeremy Minshull. Codon bias and heterologous protein expression. Trends Biotechnol., 22(7):346-353, 2004.

[22] Graeme Henkelman and Hannes Jnsson. Long time scale kinetic monte carlo simulations without lattice approximation and predefined event table. The Journal of Chemical Physics, 115(21):9657-9666, 2001.

[23] Ruth Hershberg and Dmitri A Petrov. Selection on codon bias. *Annu. Rev. Genet.*, 42:287-299, 2008. doi: 10.1 146/annurev.genet.42.110807.091442.

[24] Susan K Hoiseth and BAD Stocker. Aromatic-dependent *Salmonella* Typhimurium are non-virulent and effective as live vaccines. 1981.

[25] T Hothorn, P Bhlmann, T Kneib, M Schmid, B Hofner, F Sobotka, and F Scheipl. mboost: Model-based boosting. r package version 2.1-2.

[26] David Kennell and Howard Riezman. Transcription and translation initiation frequencies of the *Escherichia coli* lac operon. *Journal of molecular biology*, 114(1): 1-21, 1977.

[27] G. Kudla, A. W. Murray, D. Tollervey, and J. B. Plotkin. Coding-sequence determinants of gene expression in *Escherichia coli*. *Science*, 324(5924):255-258, 2009.

[28] Greg Lakatos and Tom Chou. Totally asymmetric exclusion processes with particles of arbitrary size. *Journal of Physics A: Mathematical and General*, 36(8):2027, 2003.

[29] Holger Loessner, Anne Endmann, Manfred Rohde, Roy Curtiss, and Siegfried Weiss. Differential effect of auxotrophies on the release of macromolecules by *Salmonella enterica* vaccine strains. *FEMS microbiology letters*, 265 (1):81-88, 2006.

[30] L A McReynolds, J J Monahan, D W Bendure, S L Woo, G V Paddock, W Salser, J Dorson, R E Moses, and B W O'Malley. The ovalbumin gene. insertion of ovalbumin gene sequences in chimeric bacterial plasmids. *Journal of Biological Chemistry*, 252 (6):1840-1843, 1977.

[31] Paolo Pierobon, Mauro Mobilia, Roger Kouyos, and Erwin Frey. Bottleneck-induced 50 transitions in a minimal model for intracellular transport. *Physical Review E*, 74 (3):031906, 2006.

[32] Joshua B Plotkin and Grzegorz Kudla. Synonymous but not the same: the causes and consequences of codon bias. *Nat. Rev. Genet.*, 12(1):32-42, 2010.

[33] Pere Puigb, Eduard Guzmn, Antoni Romeu, and Santiago Garcia-Vallv. Optimizer: a web server for optimizing the codon usage of DNA sequences. *Nucleic Acids Res.*, 35(suppl 2):W126-W131, 2007.

[34] S. Reuveni, I. Meilijson, M. Kupiec, E. Ruppin, and T. Tuller. Genome-scale analysis of translation elongation with a ribosome flow model. *PLoS Comput. Biol.*, 7 (9):e1002127, 2011.

[35] Karen Roos, Esther Werner, and Holger Loessner. Multicopy integration of mini-tn7 transposons into selected chromosomal sites of a *Salmonella* vaccine strain. *Microbial biotechnology*, 8(1):177-187, 2015.

[36] Sophia Rudorf and Reinhard Lipowsky. Protein Synthesis in *E. coli*: Dependence of Codon-Specific Elongation on tRNA Concentration and Codon Usage. *PLoS ONE*, 10(8):1-22, 08 2015.

[37] Sophia Rudorf, Michael Thommen, Marina V. Rodnina, and Reinhard Lipowsky. Deducing the kinetics of protein synthesis in vivo from the transition rates measured in vitro. *PLoS Comput Biol*, 10(10):e1003909, October 2014.

[38] R. Saunders and C. M. Deane. Synonymous codon usage influences the local protein structure observed. *Nucleic Acids Res.*, 38(19):6719-6728, 2010.

[39] G Schtz and E Domany. Phase transitions in an exactly soluble one-dimensional exclusion process. *Journal of statistical physics*, 72(1-2):277-296, 1993.

[40] P. Shah and M. A. Gilchrist. Effect of correlated trna abundances on translation errors and evolution of codon usage bias. *PLoS Genet.*, 6(9):e1001128, 2010.

[41] Paul M Sharp and Wen-Hsiung Li. The codon adaptation index—a measure of directional synonymous codon usage bias, and its potential applications. *Nucleic Acids Res.*, 15(3):1281-1295, 1987.

[42] Leah B Shaw, Anatoly B Kolomeisky, and Kelvin H Lee. Local inhomogeneity in asymmetric simple exclusion processes with extended objects. *Journal of Physics A: Mathematicaland General*, 37(6):2105, 2004.

[43] M. Siwiak and P. Zielenkiewicz. A comprehensive, quantitative, and genome-wide model of translation. *PLoS Comput. Biol.*, 6(7):e1000865, 2010.

[44] Marlena Siwiak and Piotr Zielenkiewicz. A comprehensive, quantitative, and genome-wide model of translation. *PLoS Computational Biology*, 6(7):e1000865, 07 2010.

[45] Marlena Siwiak and Piotr Zielenkiewicz. Transimulation-protein biosynthesis web service. *PloS one*, 8(9): e73943, 2013.

[46] Benjamin Steeb, Beatrice Claudi, Neil A Burton, Petra Tienz, Alexander Schmidt, Hesso Farhan, Alain Maz, and Dirk Bumann. Parallel exploitation of diverse host nutrients enhances *salmonella* virulence. *PLoS Pathog.*, 9(4): e11003301, 2013.

[47] Fran Supek and Tomislav S˜muc. On relevance of codon usage to expression of synthetic and natural genes in *Escherichia coli*. *Genetics*, 185(3):1129-1134, July 2010. doi: 10.1534/genetics.110.115477.

[48] Chung-Jung Tsai, Zuben E Sauna, Chava Kimchi-Sarfaty, Suresh V Ambudkar, Michael M Gottesman, and Ruth Nussinov. Synonymous mutations and ribosome stalling can lead to altered folding pathways and distinct minima. *J Mol. Biol.*, 383(2):281-291, 2008.

[49] T. Tuller, A. Carmi, K. Vestsigian, S. Navon, Y. Dorfan, J. Zaborske, T. Pan, Dahan, I. Furman, and Y. Pilpel. An evolutionarily conserved mechanism for controlling the efficiency of protein translation. *Cell*, 141(2):344-354, 2010.

[50] T. Tuller, Y. Y. Waldman, M. Kupiec, and E. Ruppin. Translation efficiency is 50 determined by both codon bias and folding energy. *Proceedings of the National Academy of Sciences*, 107(8):3645-3650, 2010.

[51] Tamir Tuller, Martin Kupiec, and Eytan Ruppin. Determinants of protein abundance and translation efficiency in *S. cerevisiae*. *PLoS Comput. Biol.*, 3(12):e248, 2007.

[52] Jesper Vind, Michael A Srensen, Michael D Rasmussen, and Steen Pedersen. Synthesis of proteins in *Escherichia coli* is limited by the concentration of free ribosomes: expression from reporter genes does not always reflect functional mrna levels. *Jour-nal of molecular biology*, 231(3):678-688, 1993.

[53] Tobias von der Haar. Mathematical and computational modelling of ribosomal movement and protein synthesis: an overview. *Computational and structural biotechnology journal*, 1(1):1-7, 2012.

[54] Arthur F Voter. Introduction to the kinetic monte carlo method. In *Radiation Effects in Solids*, pages 1-23. Springer, 2007.

[55] Mingcong Wang, Manuel Weiss, Milan Simonovic, Gabriele Haertinger, Sabine P Schrimpf, Michael O Hengartner, and Christian von Mering. Paxdb, a database of protein abundance averages across all three domains of life. *Molecular & Cellular Proteomics*, 11(8):492-500, 2012.

[56] M. Welch, S. Govindarajan, J. E. Ness, A. Villalobos, A. Gurney, J. Minshull, and Gustafsson. Design parameters to control synthetic gene expression in *Escherichia coli*. *PloS one*, 4(9):e7002, 2009.

[57] Mark Welch, Alan Villalobos, Claes Gustafsson, and Jeremy Minshull. You're one in a googol: optimizing genes for protein expression. Journal of the Royal Society Interface, 6(Suppl 4):S467-S476, 2009.

[58] Gang Wu, Nabila Bashir-bello, and Stephen Freel. The synthetic gene designer: a flexible web platform to explore sequence manipulation for heterologous expression, 2006.

[59] Yao Xu, Peijun Ma, Premal Shah, Antonis Rokas, Yi Liu, and Carl Hirschie John-son. Non-optimal codon usage is a mechanism to achieve circadian clock conditionality. Nature, 495(7439):116-120, 2013.

[60] Jian-Rong Yang, Xiaoshu Chen, and Jianzhi Zhang. Codon-by-codon modulation of translational speed and accuracy via mrna folding. 2014.

[61] Hadas Zur and Tamir Tuller. Strong association between mrna folding strength and protein abundance in *S. cerevisiae*. EMBO Rep., 13(3):272-277, 2012.

[62] Hadas Zur and Tamir Tuller. Rfmapp: ribosome flow model application. Bioinformatics, 28(12): 1663-1664, June 2012. doi: 10.1093/bioinformatics/bts185.

[63] Nakamura Y, Gojobori T, Ikemura T (2000) Codon usage tabulated from international DNA sequence databases: status for the year 2000. Nucleic Acids Res 28: 292-292.

[64] Lakatos G, Chou T (2003) Totally asymmetric exclusion processes with particles of arbitrary size. Journal of Physics A: Mathematical and General 36: 2027.

[65] Rudorf S, Lipowsky R (2015) Protein Synthesis in *E. coli*: Dependence of Codon-Specific Elongation on tRNA Concentration and Codon Usage. PLoS ONE 10: 1-22.

[66] Siwiak M, Zielenkiewicz P (2010) A comprehensive, quantitative, and genome-wide model of trans-lation. PLoS Computational Biology 6: e1000865.

[67] (2001) Initial sequencing and analysis of the human genome. Nature 409: 860-921.

[68] Kramer E B, Farabaugh P J (2007) The frequency of translational misreading errors in *E. coli* is largely determined by trna competition. RNA 13: 87-96.

[69] Rudorf S, Thommen M, Rodnina M V, Lipowsky R (2014) Deducing the kinetics of protein synthesis in vivo from the transition rates measured in vitro. PLoS Comput Biol 10: e1003909.

[70] von der Haar T (2008) A quantitative estimation of the global translational activity in logarithmi-cally growing yeast cells. BMC systems biology 2: 87.

[71] Kishore S, Jaskiewicz L, Burger L, Hausser J, Khorshid M, et al. (2011) A quantitative analysis of CLIP methods for identifying binding sites of RNA-binding proteins. Nat Meth 8: 559-564.

[72] Zheng G, Qin Y, Clark W C, Dai Q, Yi C, et al. (2015) Efficient and quantitative high-throughput tRNA sequencing. Nature Methods 12: 835-837.

[73] Geiger T, Wehner A, Schaab C, Cox J, Mann M (2012) Comparative proteomic analysis of eleven common cell lines reveals ubiquitous but varying expression of most proteins. Molecular & Cellular Proteomics 11.

[74] Nagaraj N, Kulak N A, Cox J, Neuhauser N, Mayr K, et al. (2012) System-wide perturbation analysis with nearly complete coverage of the yeast proteome by single-shot ultra hplc runs on a bench top orbitrap. Molecular & Cellular Proteomics 11: M111-013722.

[75] Tyson C B, Lord P G, Wheals A E (1979) Dependency of size of *Saccharomyces cerevisiae* cells on growth rate. Journal of bacteriology 138: 92-98.

[76] Billiard J, Dennison J B, Briand J, Annan R S, Chai D, et al. (2013) Quinoline 3-sulfonamides inhibit lactate dehydrogenase A and reverse aerobic glycolysis in cancer cells. Cancer & Metabolism 1: 1-17.

[77] Bostrm K, Wettesten M, Born J, Bondjers G, Wiklund O, et al. (1986) Pulse-chase studies of the synthesis and intracellular transport of apolipoprotein B-100 in HepG2 cells. Journal of Biological Chemistry 261: 13800-13806.

The invention claimed is:

1. A method for determining an optimized nucleotide sequence encoding a predetermined amino acid sequence of a protein of interest and expressing the optimized nucleotide sequence in a host cell, wherein the method comprises the steps of:
 (a) generating a plurality of candidate nucleotide sequences encoding the predetermined amino acid sequence;
 (b) quantifying the protein per time for each of the plurality of candidate nucleotide sequences;
 (c) obtaining a sequence score based on a continuous scoring function based on a plurality of sequence features that influence protein expression in the host cell using a boosted generalized additive model, wherein the plurality of sequence features comprises protein per time for each of the plurality of candidate nucleotide sequences of step (a);
 (d) determining, on the basis of the sequence score, the candidate nucleotide sequence with optimized protein expression in the host cell as the optimized nucleotide sequence;
 (e) introducing an expression vector comprising the optimized nucleotide sequence encoding the protein of interest into the host cell; and
 (f) incubating said host cell under conditions for expression of said optimized nucleotide sequence and expressing the protein of interest.

2. The method of claim 1, wherein the plurality of sequence features further comprises average elongation rate and/or accuracy.

3. The method of claim 1, wherein the candidate nucleotide sequences with the highest sequence score is attributed to the highest predicted protein expression in the host cell, and the nucleotide sequence with the lowest sequence score is attributed to the lowest predicted protein expression in the host cell.

4. The method of claim 1, wherein the plurality of sequence features are based on a mechanistic model of protein translation.

5. The method of claim 1, wherein the plurality of sequence features further comprises one or more sequence features selected from the group consisting of GC3, rate of slowest stretch of 12 codons, 5' folding energy of the first 30 codons, and 5' number of mRNA hairpins of the first 30 codons.

6. The method of claim 1, wherein generating a plurality of candidate nucleotide sequences comprises:
 (a1) obtaining a local score for each codon encoding a first amino acid of the amino acid sequence, wherein the local score is based on organism and codon specific elongation rates and accuracies in the form of a local scoring function;

(b1) picking a random codon encoding the amino acid weighted according to the calculated local score of step (a1);

(c1) generating a candidate nucleotide sequence by repeating steps (a1) and (b1) for all remaining amino acids of the amino acid sequence; and (d1) repeating steps (a1) to (c1) to obtain a plurality of scored candidate nucleotide sequences.

7. The method of claim 6, wherein repeating steps (a1) to (c1) is stopped when the obtained sequence score of candidate sequences according to step (b) reaches a predetermined equilibrium value.

8. The method of claim 7, wherein the predetermined equilibrium value in step (d1) is defined by the coefficient of variation of the maximum score of the last 100 sequences falling below 10%.

9. The method of claim 6, wherein before step (a1) the method performs step (a1i): determining if the wildtype-nucleotide-sequence contains a ramp of slow codons for the source organism, wherein if it contains a ramp of slow codons, a predetermined number of the first codons are not considered in the subsequent steps (a1)-(d1) and the codon optimization is performed from the predetermined number of first codons on.

10. The method of claim 9, wherein the predetermined number of first codons is within the range of the first 10-100 codons.

11. The method of claim 9, wherein the method further comprises the following steps which are executed before step (a1i):

(a1ii) translating the wildtype-nucleotide-sequence into an encoded amino acid sequence; and (a1iii) splitting the wildtype nucleotide sequence into codons according to the encoded amino acid sequence.

12. The method of claim 9, wherein the determination if the wildtype-nucleotide-sequence contains a ramp of slow codons comprises comparing an average codon adaption index, CAI, of the predetermined number of the first codons and an average codon adaption index, CAI, of the subsequent codons of the wildtype-nucleotide-sequence, wherein the CAI is determined with respect to the wildtype-nucleotide-sequence and can be substituted by an average codon-specific elongation rate if codon specific elongation rates are available for the wildtype-nucleotide-sequence.

13. The method of claim 1, wherein the amino acid sequence is encoded by a wildtype-sequence from a source organism.

14. The method of claim 1, further comprising adapting a relative weighting of sequence features to allow for an optimization with respect to translation accuracy or slow translation for increased time of co-translational folding.

15. A method for producing a protein of interest comprising the steps of:

generating a plurality of candidate codon optimized nucleotide sequences encoding the predetermined amino acid sequence of the protein of interest;

quantifying the protein per time for each of the plurality of candidate codon optimized nucleotide sequences;

obtaining a sequence score based on a continuous scoring function based on a plurality of sequence features that influence protein expression in the host cell using a boosted generalized additive model, wherein the plurality of sequence features comprises protein per time for each of the plurality of candidate codon optimized nucleotide sequences of step (a); and determining the candidate codon optimized nucleotide sequence that exhibits optimized protein expression in the host cell ands identifying that nucleotide sequence as the optimized nucleotide sequence;

introducing an expression cassette comprising a promoter operatively linked to the optimized nucleic acid sequence encoding the protein of interest into a host cell; and incubating said host cell under conditions allowing for expression of said nucleic acid to obtain said protein of interest;

wherein said codon optimized nucleic acid encodes a predetermined amino acid sequence of the protein of interest and said codon optimized nucleic acid comprises a nucleotide sequence that is codon optimized for expression of said protein of interest in said host cell.

16. The method of claim 1, wherein step (b) further comprises quantifying the average elongation rate and/or accuracy and wherein the plurality of sequence features of step (c) further comprises average elongation rate and/or accuracy.

* * * * *

UNITED STATES PATENT AND TRADEMARK OFFICE
CERTIFICATE OF CORRECTION

PATENT NO. : 11,848,074 B2
APPLICATION NO. : 16/467528
DATED : December 19, 2023
INVENTOR(S) : Reinhard Lipowsky et al.

It is certified that error appears in the above-identified patent and that said Letters Patent is hereby corrected as shown below:

In the Specification

Column 19,
Line 56, "frame St" should read --frame $\delta t$--.

Column 60,
Line 12, "at a rate 7" should read --at a rate $\gamma$--.

Signed and Sealed this
Second Day of July, 2024

Katherine Kelly Vidal
*Director of the United States Patent and Trademark Office*